United States Patent
Jung et al.

(10) Patent No.: US 8,586,200 B2
(45) Date of Patent: Nov. 19, 2013

(54) ORGANIC COMPOUND, AND ORGANIC PHOTOELECTRIC DEVICE INCLUDING THE SAME

(75) Inventors: Sung-Hyun Jung, Gunpo-si (KR); Hyung-Sun Kim, Uiwang-si (KR); Ho-Jae Lee, Yongin-si (KR); Eun-Sun Yu, Anyang-si (KR); Mi-Young Chae, Yongin-si (KR)

(73) Assignee: Cheil Industries, Inc., Gumi-si, Gyeongsangbuk-do (KR)

( * ) Notice: Subject to any disclaimer, the term of this patent is extended or adjusted under 35 U.S.C. 154(b) by 434 days.

(21) Appl. No.: 12/659,581

(22) Filed: Mar. 12, 2010

(65) Prior Publication Data
US 2011/0042654 A1 Feb. 24, 2011

Related U.S. Application Data

(63) Continuation-in-part of application No. PCT/KR2008/005413, filed on Sep. 12, 2008.

(30) Foreign Application Priority Data

Sep. 14, 2007 (KR) .................. 10-2007-0093879

(51) Int. Cl.
*H01L 51/54* (2006.01)

(52) U.S. Cl.
USPC ........... 428/690; 428/917; 313/504; 313/505; 313/506; 257/40; 257/E51.05; 257/E51.026; 257/E51.032; 546/19; 546/79; 546/81; 546/101; 544/234

(58) Field of Classification Search
USPC ........ 546/18, 79, 81, 101; 313/504, 505, 506; 257/40, E51.05, E51.026, E51.032; 248/690, 917; 548/440; 428/690, 917; 544/440, 234
See application file for complete search history.

(56) References Cited

U.S. PATENT DOCUMENTS

| 6,670,054 B1 | 12/2003 | Hu et al. |
| 7,737,248 B2 | 6/2010 | Yamada et al. |

(Continued)

FOREIGN PATENT DOCUMENTS

| CN | 1 769 269 A | 5/2006 |
| JP | 2004-281296 A | 10/2004 |

(Continued)

OTHER PUBLICATIONS

Chiang et al., Novel Carbazole/Fluorene Hybrids: Host Materials for Blue Phosphorescent OLEDs, 2006, Organic Letters, vol. 8, No. 12, pp. 2799-2802.*

(Continued)

*Primary Examiner* — Gregory Clark
(74) *Attorney, Agent, or Firm* — Lee & Morse, P.C.

(57) ABSTRACT

Disclosed is an organic compound represented by the following Chemical Formula 1 that easily dissolves in an organic solvent, and that is applicable as a host material of an emission layer of an organic photoelectric device since it emits fluorescence and phosphorescence at a red wavelength through a blue wavelength.

[Chemical Formula 1]

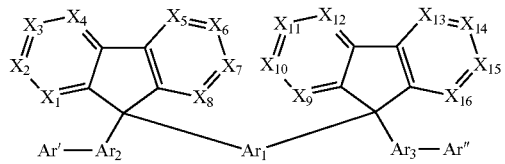

16 Claims, 14 Drawing Sheets

(56) References Cited

U.S. PATENT DOCUMENTS

2005/0127826 A1* 6/2005 Qiu et al. .................. 313/504
2005/0176909 A1  8/2005 Nishiguchi et al.

FOREIGN PATENT DOCUMENTS

| JP | 2005-183345 A | 7/2005 |
| JP | 2007-224193 A | 9/2007 |
| WO | WO 2005/042621 A1 | 5/2005 |

OTHER PUBLICATIONS

Wu et. al., Fluorene: A novel host material for Highly Efficient Green and Red Phosdphorescent OLEDS, 2005, Organic Letters, vol. 7, No. 24, pp. 5361-5364.*

Xie et. al., Fluorene: Facile Synthesis of Complicated 9,9-Diarylfluorenes Based on BF3-Et2O-Mediated Friedel-Crafts Reaction, 2006, Organic Letters, vol. 8, No. 17, pp. 3701-3704.*

* cited by examiner

ORGANIC COMPOUND, AND ORGANIC PHOTOELECTRIC DEVICE INCLUDING THE SAME

CROSS-REFERENCE TO RELATED APPLICATION

This application claims priority to and the benefit of Korean Patent Application No. 10-2007-0093879 filed in the Korean Intellectual Property Office on Sep. 14, 2007, the entire contents of which are incorporated herein by reference.

BACKGROUND OF THE INVENTION (a) Field of the Invention

The present invention relates to an organic compound and an organic photoelectric device including the same. More particularly, the present invention relates to an organic compound that easily dissolves in an organic solvent, and is applicable as a host material of an emission layer of an organic photoelectric device since it emits fluorescence and phosphorescence at a red wavelength through a blue wavelength, and an organic photoelectric device including the same.

(b) Description of the Related Art

An organic photoelectric device includes an organic light emitting material between a rear plate including ITO transparent electrode patterns as an anode on a transparent glass substrate and an upper plate including a metal electrode as a cathode on a substrate. When a predetermined voltage is applied between the transparent electrode and metal electrode, current flows through the organic light emitting material to emit light.

Such an organic light emitting material for an organic photoelectric device was firstly developed by Eastman Kodak, Inc., in 1987. The material is a low molecular aromatic diamine and aluminum complex as an emission-layer-forming material (Applied Physics Letters. 51, 913, 1987). C. W Tang et al. firstly disclosed a practicable device as an organic photoelectric device in 1987 (Applied Physics Letters, 51 12, 913-915, 1987).

According to the reference, the organic layer has a structure in which a thin film (hole transport layer (HTL)) of a diamine derivative and a thin film of tris(8-hydroxy-quinolate)aluminum ($Alq_3$) are laminated. The $Alq_3$ thin film functions as an emission layer for transporting electrons. The $Alq_3$ thin film functions as an emission layer for transporting electrons.

Generally, the organic photoelectric device is composed of an anode of a transparent electrode, an organic thin layer of a light emitting region, and a metal electrode (cathode) formed on a glass substrate, in that order. The organic thin layer may includes an emission layer, a hole injection layer (HIL), a hole transport layer (HTL), an electron transport layer (ETL), or an electron injection layer (EIL). It may further include an electron blocking layer or a hole blocking layer due to the emission characteristics of the emission layer.

When the organic photoelectric device is applied with an electric field, holes and electrons are injected from the anode and the cathode, respectively. The injected holes and electrons are recombined on the emission layer though the hole transport layer (HTL) and the electron transport layer (ETL) to provide light emitting excitons.

The provided light emitting excitons emit light by transiting to the ground state.

The light emitting may be classified as a fluorescent material including singlet excitons and a phosphorescent material including triplet excitons.

Recently, it has become known that the phosphorescent light emitting material can be used for a light emitting material in addition to the fluorescent light emitting material (D. F. O'Brien et al., Applied Physics Letters, 74 3, 442-444, 1999; M. A. Baldo et al., Applied Physics letters, 75 1, 4-6, 1999). Such phosphorescent emission occurs by transiting electrons from the ground state to the exited state, non-radiative transiting of a singlet exciton to a triplet exciton through intersystem crossing, and transiting the triplet exciton to the ground state to emit light.

When the triplet exciton is transited, it cannot directly transit to the ground state. Therefore, the electron spin is flipped, and then it is transited to the ground state so that it provides a characteristic of extending the lifetime (emission duration) to more than that of fluorescent.

In other words, the duration of fluorescent emission is extremely short at several nanoseconds, but the duration of phosphorescent emission is relatively long such as at several microseconds, so that it provides a characteristic of extending the lifetime (emission duration) to more than that of the fluorescent emission.

In addition, evaluating quantum mechanically, when holes injected from the anode are recombined with electrons injected from the cathode to provide light emitting excitons, the singlet and the triplet are produced in a ratio of 1:3, in which the triplet light emitting excitons are produced at three times the amount of the singlet light emitting excitons in the organic photoelectric device.

Accordingly, the percentage of the singlet exited state is 25% (the triplet is 75%) in the case of a fluorescent material, so it has limits in luminous efficiency. On the other hand, in the case of a phosphorescent material, it can utilize 75% of the triplet exited state and 25% of the singlet exited state, so theoretically the internal quantum efficiency can reach up to 100%. When a phosphorescent light emitting material is used, it has advantages in an increase in luminous efficiency of around four times that of the fluorescent light emitting material.

In the above-mentioned organic light emitting diode, a light emitting colorant (dopant) may be added in an emission layer (host) in order to increase the efficiency and stability in the emission state.

In this structure, the efficiency and properties of the light emission diodes are dependent on the host material in the emission layer. According to studies regarding the emission layer (host), the organic host material can be exemplified by a material including naphthalene, anthracene, phenanthrene, tetracene, pyrene, benzopyrene, chrysene, pycene, carbazole, fluorene, biphenyl, terphenyl, triphenylene oxide, dihalobiphenyl, trans-stilbene, and 1,4-diphenylbutadiene.

Generally, the host material includes 4,4-N,N-dicarbazolebiphenyl (CBP) having a glass transition temperature of 110° C. or less and a thermal decomposition temperature of 400° C. or less, in which the thermal stability is low and the symmetry is excessively high. Thereby, it tends to crystallize and cause problems such as a short and a pixel defect according to results of thermal resistance tests of the devices.

In addition, most host materials including CBP are materials in which the hole transporting property is greater than the electron transporting property. In other words, as the injected hole transportation is faster than the injected electron transportation, the excitons are ineffectively formed in the emission layer. Therefore, the resultant device has deteriorated luminous efficiency.

Accordingly, in order to realize a highly efficient and long lifetime organic light emitting device, it is required to develop a phosphorescent host material having high electrical and thermal stability and that is capable of transporting both holes and electrons.

SUMMARY OF THE INVENTION

One aspect of the present invention provides an organic compound that easily dissolves in an organic solvent, and is applicable as a host material of an emission layer of an organic photoelectric device since it emits fluorescence and phosphorescence at a red wavelength through a blue wavelength.

Another aspect of the present invention provides an organic photoelectric device including the organic compound.

The aspects of the present invention are not limited to the above technical purposes, and a person of ordinary skill in the art can understand other technical purposes.

According to one aspect of the present invention, provided is an organic compound represented by the following Chemical Formula 1:

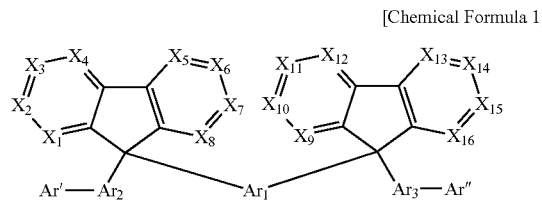

[Chemical Formula 1]

In the above Chemical Formula 1, $X_1$ to $X_{16}$ are the same or different and independently selected from CR' or N, $Ar_1$ to $Ar_3$ are the same or different and independently selected from a single bond, a substituted or unsubstituted C6 to C30 arylene group, or a substituted or unsubstituted C2 to C30 heteroarylene group, and Ar' and Ar" are the same or different and independently are selected from a substituted or unsubstituted C6 to C30 aryl group, or a substituted or unsubstituted C2 to C30 heteroaryl group, wherein R' is independently selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, or a substituted or unsubstituted C3 to C40 silyl group.

$Ar_1$ to $Ar_3$ are the same or different, and may be independently selected from a substituted or unsubstituted carbazole, a substituted or unsubstituted arylamine, a substituted or unsubstituted phenyl, a substituted or unsubstituted tolyl, a substituted or unsubstituted naphthyl, a substituted or unsubstituted stilbene, a substituted or unsubstituted fluorenyl, a substituted or unsubstituted anthracenyl, a substituted or unsubstituted terphenyl, a substituted or unsubstituted pyrenyl, a substituted or unsubstituted diphenyl anthracenyl, a substituted or unsubstituted dinaphthylanthracenyl, a substituted or unsubstituted pentacenyl, a substituted or unsubstituted bromophenyl, a substituted or unsubstituted hydroxyphenyl, a substituted or unsubstituted thienyl, a substituted or unsubstituted pyridyl, a substituted or unsubstituted azobenzenyl, or a substituted or unsubstituted ferrocenyl. Ar' and Ar" are the same or different, and are independently selected from a substituted or unsubstituted carbazole, a substituted or unsubstituted arylamine, a substituted or unsubstituted phenyl, a substituted or unsubstituted naphthyl, a substituted or unsubstituted anthracenyl, a substituted or unsubstituted fluorene, a substituted or unsubstituted thiophene, a substituted or unsubstituted pyrrole, a substituted or unsubstituted pyridine, a substituted or unsubstituted aryloxadiazole, a substituted or unsubstituted triazole, or a substituted or unsubstituted arylsilane.

Ar' and Ar" are the same or different, and are independently selected from substituents represented by the following Chemical Formulae 2 to 31.

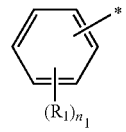

[Chemical Formula 2]

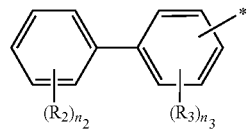

[Chemical Formula 3]

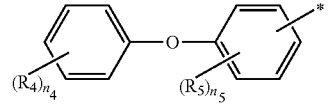

[Chemical Formula 4]

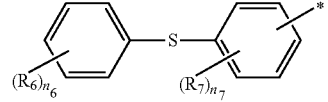

[Chemical Formula 5]

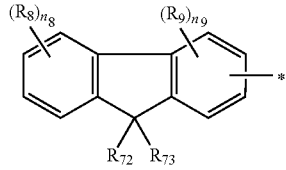

[Chemical Formula 6]

[Chemical Formula 7]
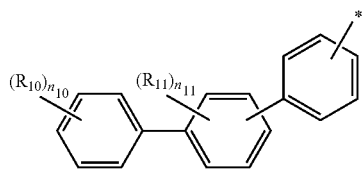
[Chemical Formula 8]
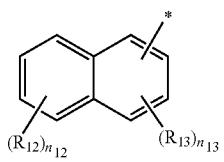
[Chemical Formula 9]
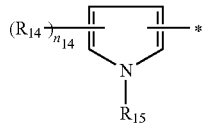
[Chemical Formula 10]
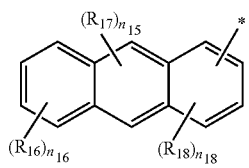
[Chemical Formula 11]
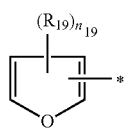
[Chemical Formula 12]
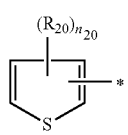
[Chemical Formula 13]
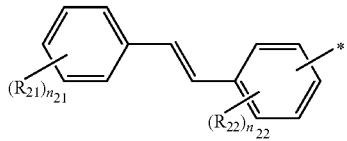
[Chemical Formula 14]
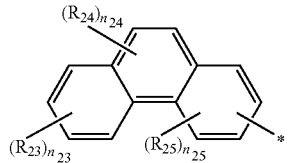
[Chemical Formula 15]
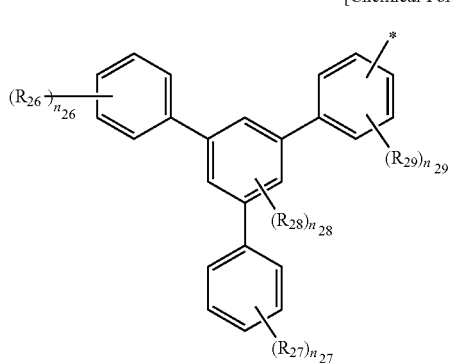
[Chemical Formula 16]
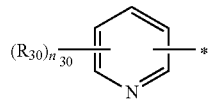
[Chemical Formula 17]
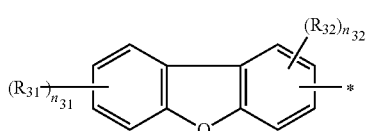
[Chemical Formula 18]
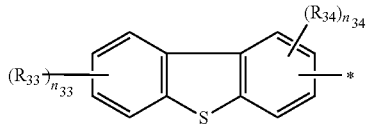
[Chemical Formula 19]
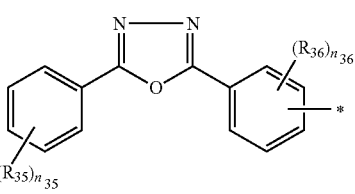
[Chemical Formula 20]
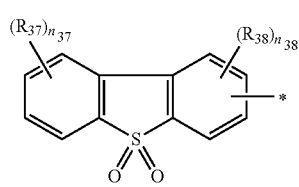
[Chemical Formula 21]
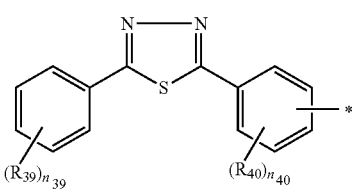

[Chemical Formula 22]

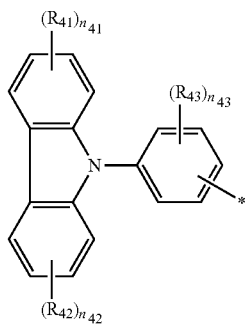

[Chemical Formula 23]

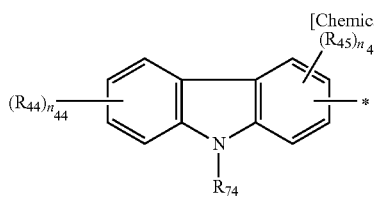

[Chemical Formula 24]

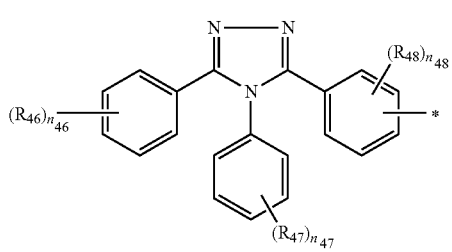

[Chemical Formula 25]

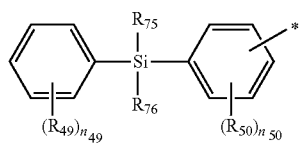

[Chemical Formula 26]

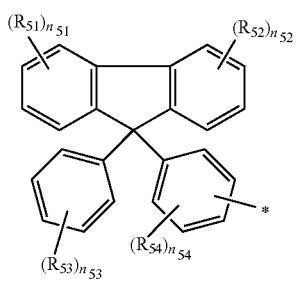

[Chemical Formula 27]

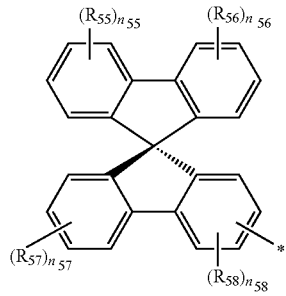

[Chemical Formula 28]

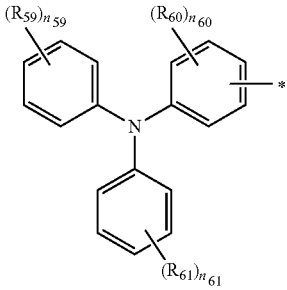

[Chemical Formula 29]

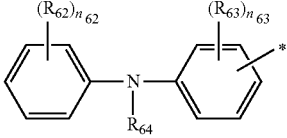

[Chemical Formula 30]

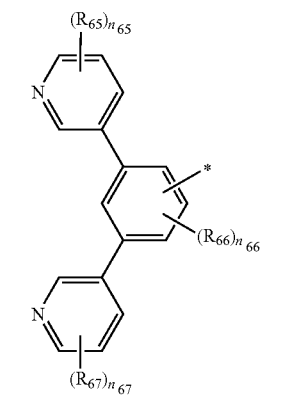

[Chemical Formula 31]

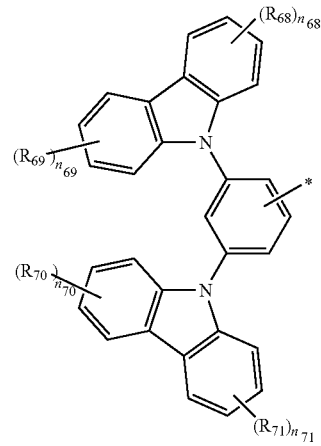

In the above Chemical Formulae 2 to 31, $R_1$ to $R_{76}$ are the same or different, and are independently selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, or a substituted or unsubstituted C3 to C40 silyl, $n_1, n_2, n_4, n_6, n_{10}, n_{21}, n_{26}, n_{27}, n_{35}, n_{39}, n_{46}, n_{47}, n_{49}, n_{53}, n_{59}, n_{61}$, and $n_{62}$ are the same or different, and are independently integers ranging from 0 to 5, $n_3, n_5, n_7, n_8, n_{11}, n_{12}, n_{16}, n_{22}, n_{23}, n_{29}, n_{30}, n_{31}, n_{33}, n_{36}, n_{37}, n_{40}, n_{41}$ to $n_{44}, n_{48}, n_{50}$ to $n_{52}, n_{54}, n_{55}, n_{57}, n_{56}, n_{60}, n_{63}, n_{65}, n_{67}, n_{68}, n_{69}, n_{70}$, and $n_{71}$ are the same or different, and are independently integers ranging from 0 to 4, $n_9, n_{13}, n_{14}, n_{18}, n_{19}, n_{20}, n_{25}, n_{28}, n_{32}, n_{34}, n_{38}, n_{45}, n_{58}$, and $n_{66}$ are the same or different, and are independently integers ranging from 0 to 3, and $n_{15}$ and $n_{24}$ are the same or different, and are independently integers ranging from 0 to 2.

According to another aspect of the present invention, an organic compound represented by the following Chemical Formula 32 is provided.

[Chemical Formula 32]

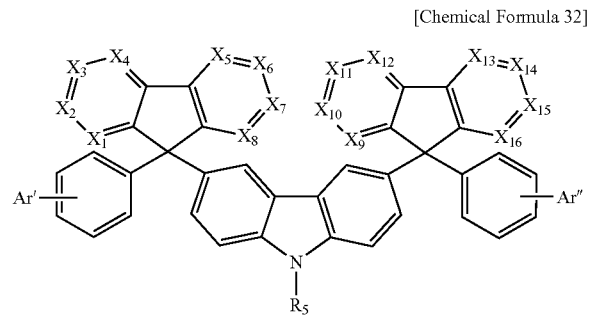

In the above Chemical Formula 32, $X_1$ to $X_{16}$ are the same or different, and are independently selected from CR' and N, Ar' and Ar" are the same or different, and are independently selected from a substituted or unsubstituted C6 to C30 aryl group or a substituted or unsubstituted C2 to C30 heteroaryl group, and R5 and R' are the same or different, and are independently selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, or a substituted or unsubstituted C3 to C40 silyl group, Ar' and Ar" are the same or different, and are independently selected from substituents represented by the following Chemical Formulae B-1 to B-9.

[Chemical Formula B-1]
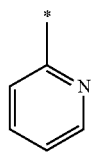

[Chemical Formula B-2]
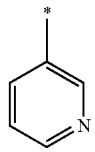

[Chemical Formula B-3]
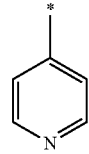

[Chemical Formula B-4]
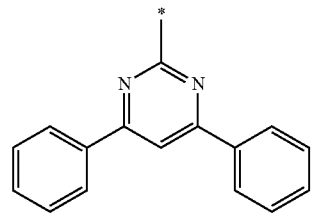

[Chemical Formula B-5]
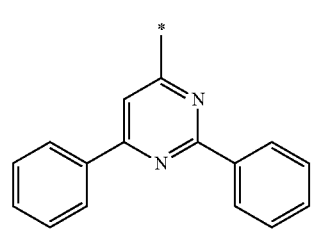

[Chemical Formula B-6]
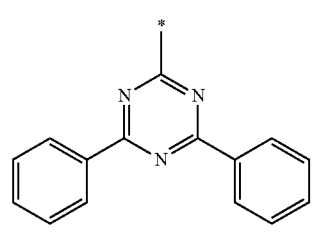

[Chemical Formula B-7]
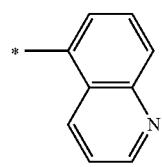

[Chemical Formula B-8]
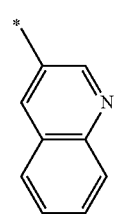

[Chemical Formula B-9]
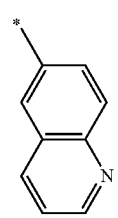

Ar' and Ar" are the same or different, and are independently selected from a substituted or unsubstituted carbazolyl, a substituted or unsubstituted arylamine, a substituted or unsubstituted phenyl, a substituted or unsubstituted naphthyl, a substituted or unsubstituted anthracenyl, a substituted or unsubstituted fluorenyl, a substituted or unsubstituted thiophene, a substituted or unsubstituted pyrrole, a substituted or unsubstituted pyridine, a substituted or unsubstituted aryloxadiazole, a substituted or unsubstituted triazole, or a substituted or unsubstituted arylsilane.

Ar' and Ar" are the same or different, and are independently selected from substituents represented by the following Chemical Formulae 2 to 31.

[Chemical Formula 2]
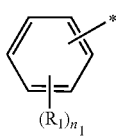

[Chemical Formula 3]
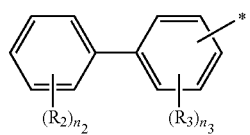

[Chemical Formula 4]
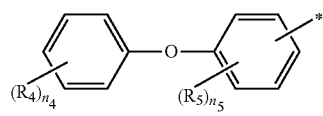

[Chemical Formula 5]
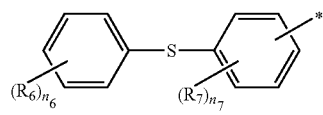

[Chemical Formula 6]
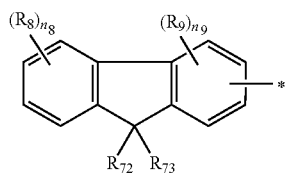

[Chemical Formula 7]
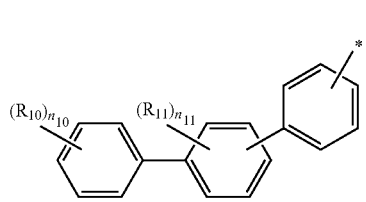

[Chemical Formula 8]
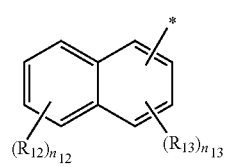

[Chemical Formula 9]
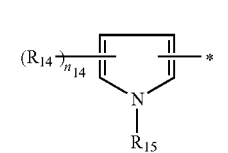

[Chemical Formula 10]
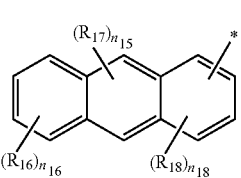

[Chemical Formula 11]
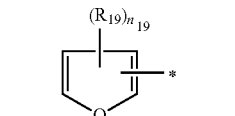

[Chemical Formula 12]
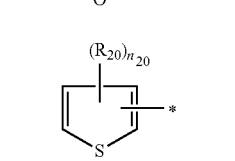

[Chemical Formula 13]
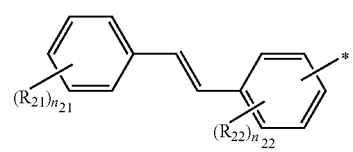

[Chemical Formula 14]
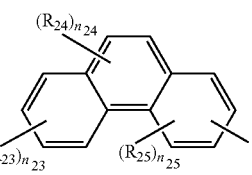

[Chemical Formula 15]
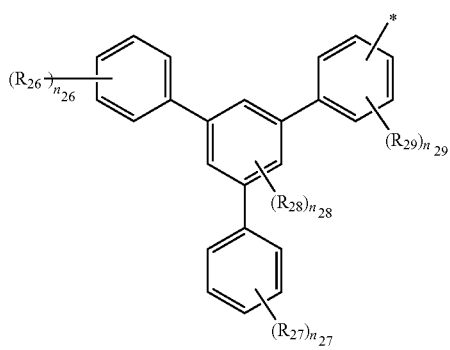
[Chemical Formula 16]
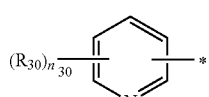
[Chemical Formula 17]
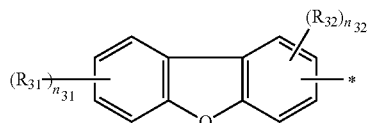
[Chemical Formula 18]
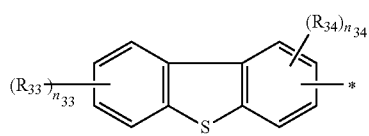
[Chemical Formula 19]
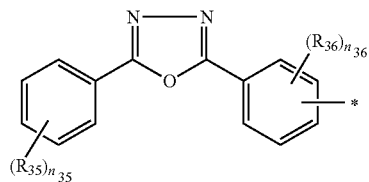
[Chemical Formula 20]
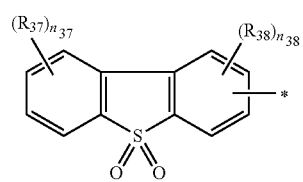
[Chemical Formula 21]
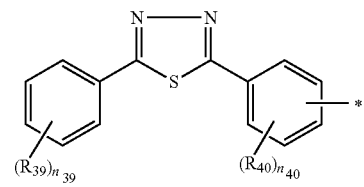
[Chemical Formula 22]
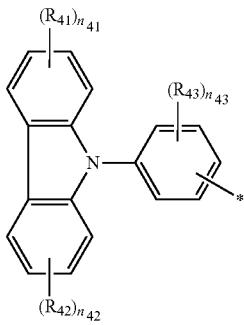
[Chemical Formula 23]
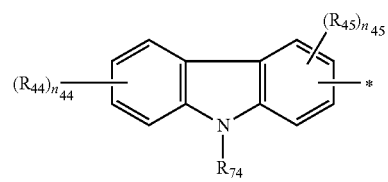
[Chemical Formula 24]
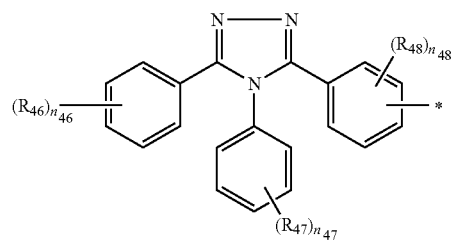
[Chemical Formula 25]
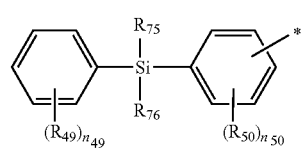
[Chemical Formula 26]
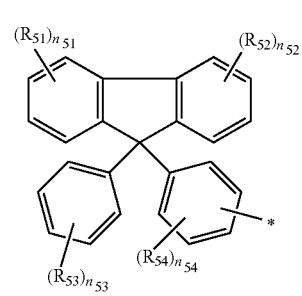
[Chemical Formula 27]
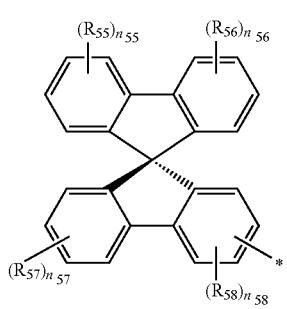

[Chemical Formula 28]

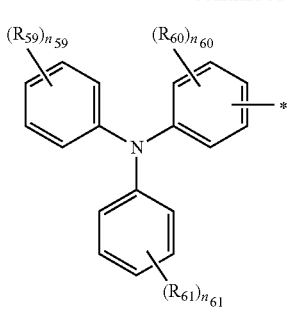

[Chemical Formula 29]

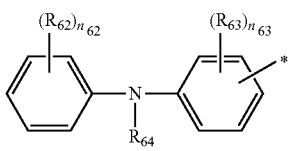

[Chemical Formula 30]

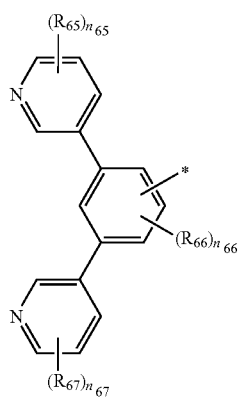

[Chemical Formula 31]

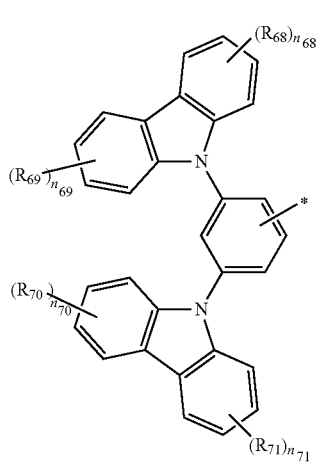

In the above Chemical Formulae 2 to 31, $R_1$ to $R_{76}$ are the same or different, and are independently a halogen, a cyano group, a hydroxyl group, an amino group, a nitro group, a carboxyl group, a substituted or unsubstituted C1 to 20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to 20 acyloxy group, a substituted or unsubstituted C2 to 20 acylamino group, a substituted or unsubstituted C2 to 20 alkoxy carbonyl amino group, a substituted or unsubstituted C7 to 20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, or a substituted or unsubstituted C3 to C40 silyl group, $n_1$, $n_2$, $n_4$, $n_6$, $n_{10}$, $n_{21}$, $n_{26}$, $n_{27}$, $n_{35}$, $n_{39}$, $n_{46}$, $n_{47}$, $n_{49}$, $n_{53}$, $n_{59}$, $n_{61}$, and $n_{62}$ are the same or different, and are independently integers ranging from 0 to 5, $n_3$, $n_5$, $n_7$, $n_8$, $n_{11}$, $n_{12}$, $n_{16}$, $n_{22}$, $n_{23}$, $n_{29}$, $n_{30}$, $n_{31}$, $n_{33}$, $n_{36}$, $n_{37}$, $n_{40}$, $n_{41}$ to $n_{44}$, $n_{48}$, $n_{50}$ to $n_{52}$, $n_{54}$, $n_{55}$, $n_{57}$, $n_{56}$, $n_{60}$, $n_{63}$, $n_{65}$, $n_{67}$, $n_{68}$, $n_{69}$, $n_{70}$, and $n_{71}$ are the same or different, and are independently integers ranging from 0 to 4, $n_9$, $n_{13}$, $n_{14}$, $n_{18}$, $n_{19}$, $n_{20}$, $n_{25}$, $n_{28}$, $n_{32}$, $n_{34}$, $n_{38}$, $n_{45}$, $n_{58}$, and $n_{66}$ are the same or different, and are independently integers ranging from 0 to 3, and $n_{15}$ and $n_{24}$ are the same or different, and are independently integers ranging from 0 to 2.

According to another aspect of the present invention, provided is an organic compound represented by one of the Chemical Formulae selected from the following Chemical Formulae 33 to 37.

[Chemical Formula 33]
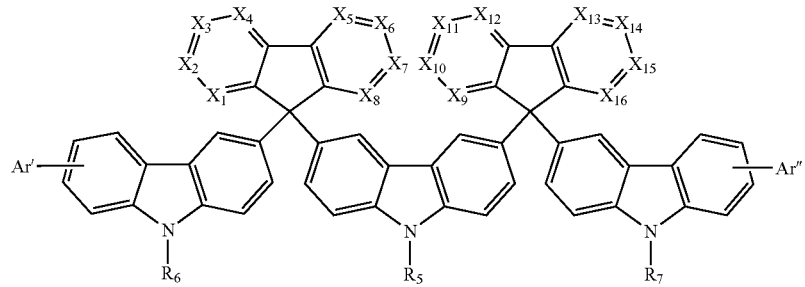
[Chemical Formula 34]
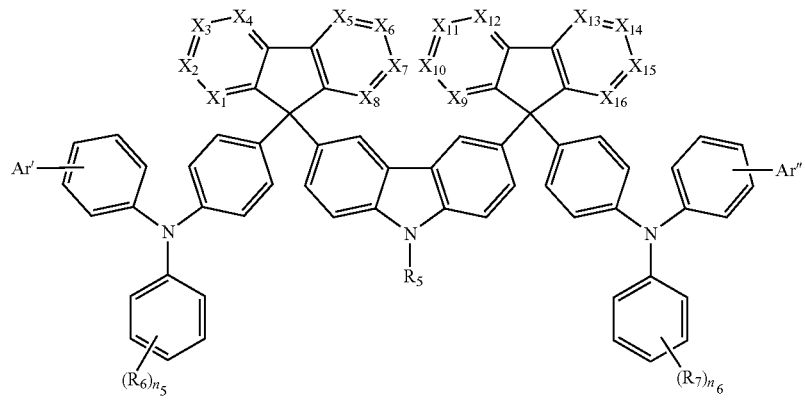
[Chemical Formula 35]
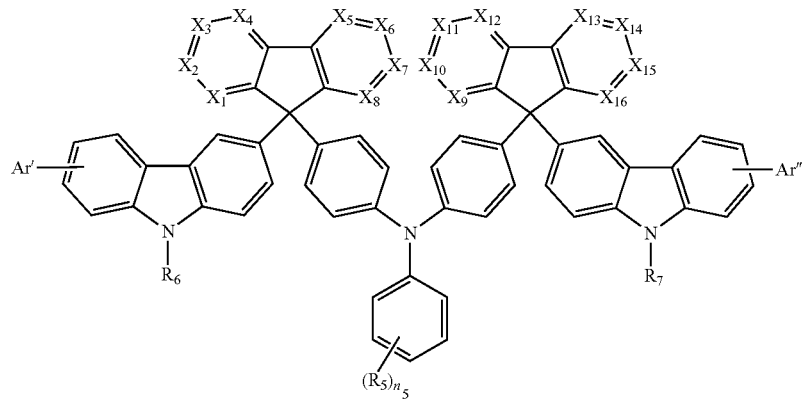
[Chemical Formula 36]
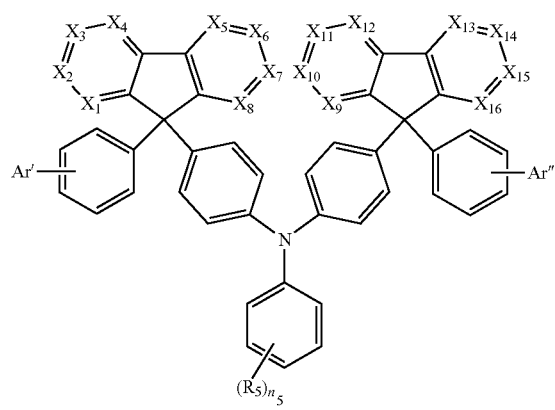

[Chemical Formula 37]

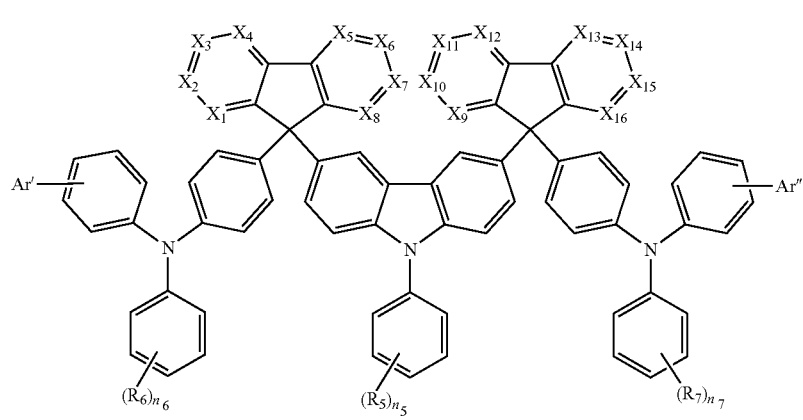

In the above Chemical Formulae 33 to 37, $X_1$ to $X_{16}$ are the same or different, and are independently selected from CR' or N, Ar' and Ar'' are the same or different, and are independently selected from a substituted or unsubstituted C6 to C30 aryl group or a substituted or unsubstituted C2 to C30 heteroaryl group, $R_5$ to $R_7$ and R' are the same or different, and are independently hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, or a substituted or unsubstituted C3 to C40 silyl group, and $n_5$ to $n_7$ are the same or different, and are independently integers ranging from 0 to 5.

Ar' and Ar'' are the same or different, and are independently selected from substituents represented by the following Chemical Formulae B-1 to B-9.

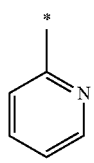

[Chemical Formula B-1]

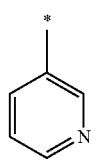

[Chemical Formula B-2]

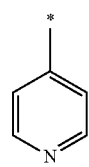

[Chemical Formula B-3]

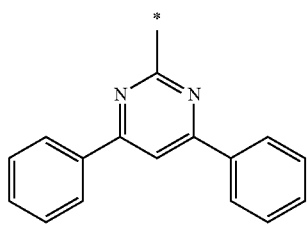

[Chemical Formula B-4]

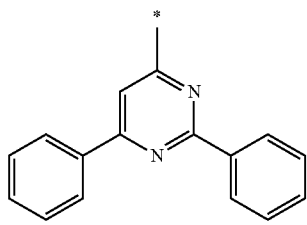

[Chemical Formula B-5]

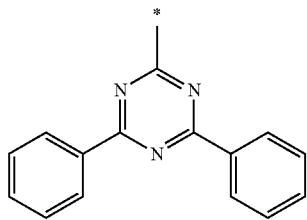

[Chemical Formula B-6]

[Chemical Formula B-7]

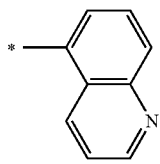

[Chemical Formula B-8]

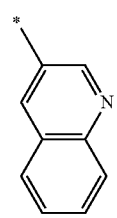

[Chemical Formula B-9]

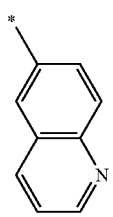

Ar' and Ar" are the same or different, and are independently selected from a substituted or unsubstituted carbazole, a substituted or unsubstituted arylamine, a substituted or unsubstituted phenyl, a substituted or unsubstituted naphthyl, a substituted or unsubstituted anthracenyl, a substituted or unsubstituted fluorene, a substituted or unsubstituted thiophene, a substituted or unsubstituted pyrrole, a substituted or unsubstituted pyridine, a substituted or unsubstituted aryloxadiazole, a substituted or unsubstituted triazole, or a substituted or unsubstituted arylsilane.

Ar' and Ar" are the same or different, and are independently selected from substituents represented by the following Chemical Formulae 2 to 31.

[Chemical Formula 2]

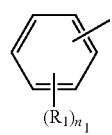

[Chemical Formula 3]

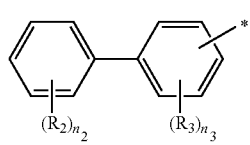

[Chemical Formula 4]

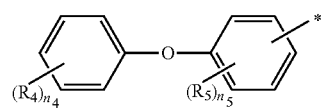

[Chemical Formula 5]

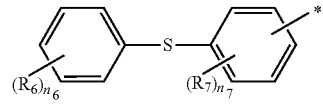

[Chemical Formula 6]

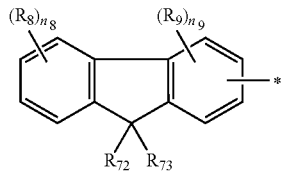

[Chemical Formula 7]

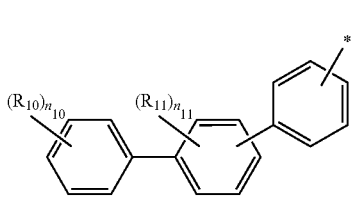

[Chemical Formula 8]

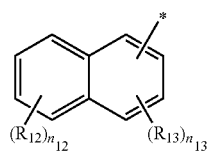

[Chemical Formula 9]

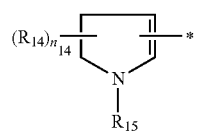

[Chemical Formula 10]

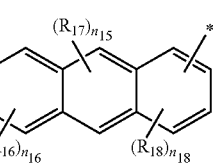

[Chemical Formula 11]

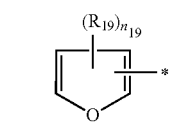

[Chemical Formula 12]

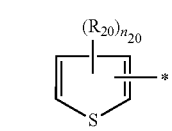

[Chemical Formula 13]

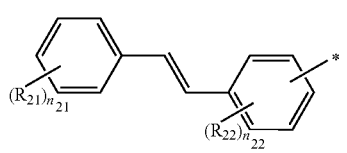

[Chemical Formula 14]

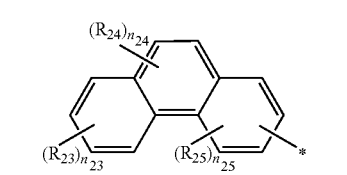

[Chemical Formula 15]
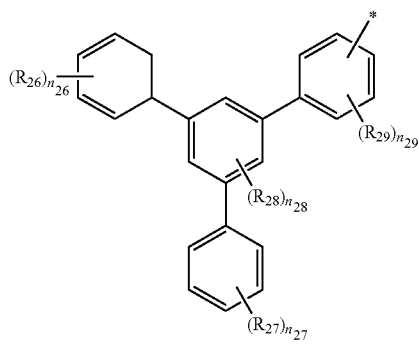
[Chemical Formula 16]
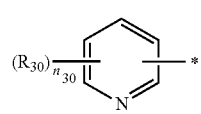
[Chemical Formula 17]
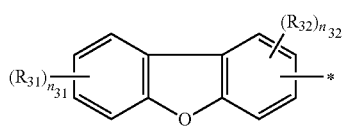
[Chemical Formula 18]
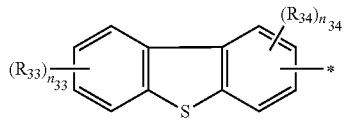
[Chemical Formula 19]
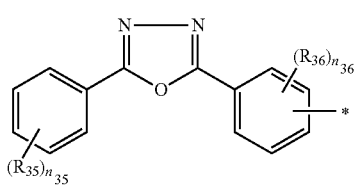
[Chemical Formula 20]
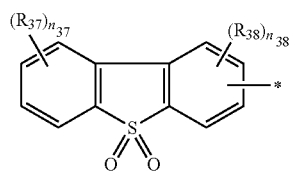
[Chemical Formula 21]
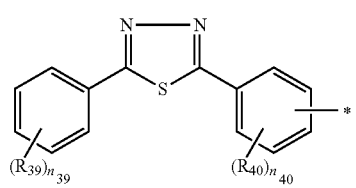
[Chemical Formula 22]
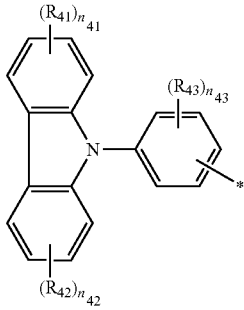
[Chemical Formula 23]
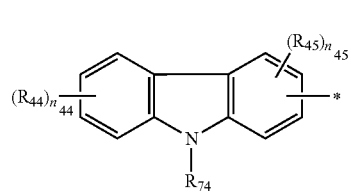
[Chemical Formula 24]
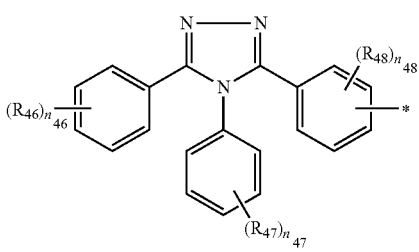
[Chemical Formula 25]
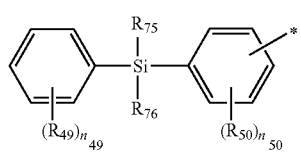
[Chemical Formula 26]
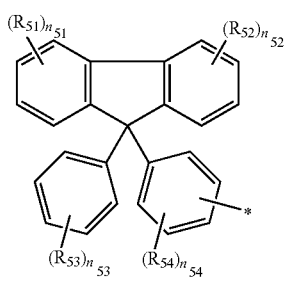
[Chemical Formula 27]
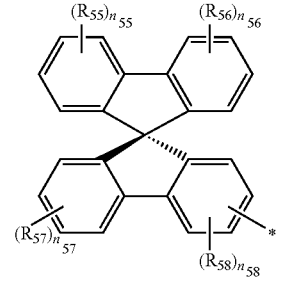

-continued

[Chemical Formula 28]

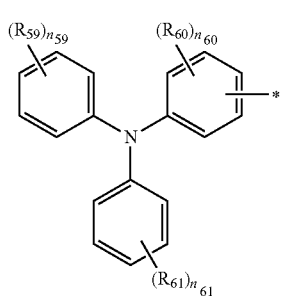

[Chemical Formula 29]

[Chemical Formula 30]

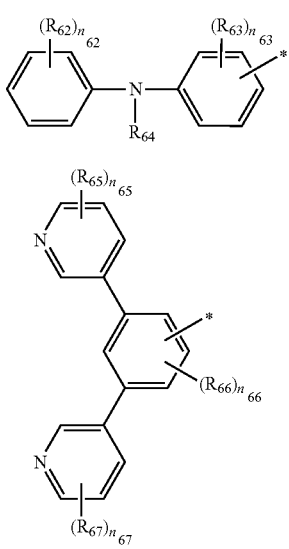

[Chemical Formula 31]

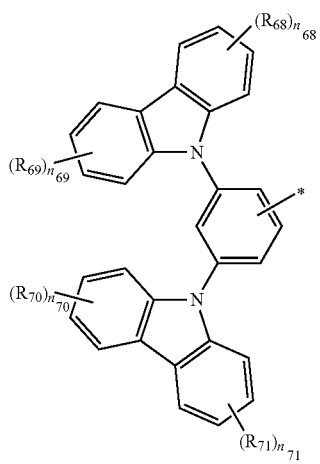

In the above Chemical Formulae 2 to 31, $R_1$ to $R_{76}$ are the same or different, and are independently selected from a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, or a substituted or unsubstituted C3 to C40 silyl group, $n_1$, $n_2$, $n_4$, $n_6$, $n_{10}$, $n_{21}$, $n_{26}$, $n_{27}$, $n_{35}$, $n_{39}$, $n_{46}$, $n_{47}$, $n_{49}$, $n_{53}$, $n_{59}$, $n_{61}$, and $n_{62}$ are the same or different, and are independently integers ranging from 0 to 5, $n_3$, $n_5$, $n_7$, $n_8$, $n_{11}$, $n_{12}$, $n_{16}$, $n_{22}$, $n_{23}$, $n_{29}$, $n_{30}$, $n_{31}$, $n_{33}$, $n_{36}$, $n_{37}$, $n_{40}$, $n_{41}$ to $n_{44}$,
$n_{48}$, $n_{50}$ to $n_{52}$, $n_{54}$, $n_{55}$, $n_{57}$, $n_{56}$, $n_{60}$, $n_{63}$, $n_{65}$, $n_{67}$, $n_{68}$, $n_{69}$, $n_{70}$, and $n_{71}$ are the same or different, and are independently integers ranging from 0 to 4, $n_9$, $n_{13}$, $n_{14}$, $n_{18}$, $n_{19}$, $n_{20}$, $n_{25}$, $n_{28}$, $n_{32}$, $n_{34}$, $n_{38}$, $n_{45}$, $n_{58}$, and $n_{66}$ are the same or different, and are independently integers ranging from 0 to 3, and $n_{15}$ and $n_{24}$ are the same or different, and are independently integers ranging from 0 to 2.

According to still another aspect of the present invention, provided is an organic photoelectric device that includes an organic thin layer disposed between a pair of electrodes. The organic thin layer includes the above organic compound.

The organic layer may be an emission layer.

The organic layer may be selected from a hole injection layer (HIL), a hole transport layer (HTL), a hole blocking film, and a combination thereof.

The organic layer may be selected from an electron injection layer (EIL), an electron transport layer (ETL), an electron blocking film, and a combination thereof.

Hereinafter, further embodiments of the present invention will be described in detail.

The organic compound easily dissolves in an organic solvent, and is applicable as a host material of an emission layer of an organic photoelectric device since it emits fluorescence and phosphorescence at a red wavelength through a blue wavelength.

DESCRIPTION OF REFERENCE NUMERALS INDICATING PRIMARY ELEMENTS IN THE DRAWINGS

Figure 1:
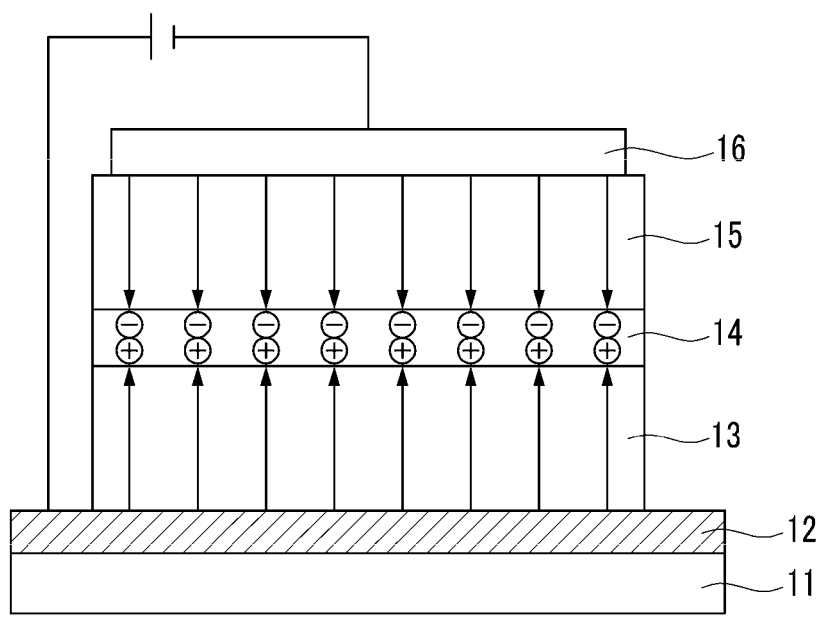
FIG. 1 is a cross-sectional view showing an organic photoelectric device according to one embodiment of the present invention.

11: substrate 12: anode
13: hole transport layer (HTL) 14: organic emission layer
15: electron transport layer (ETL) 16: cathode

DETAILED DESCRIPTION OF THE EMBODIMENTS

Exemplary embodiments of the present invention will hereinafter be described in detail. However, these embodiments are only exemplary, and the present invention is not limited thereto but rather is defined by scope of the appended claims.

According to one embodiment of the present invention, provided is the organic compound represented by the following Chemical Formula 1:

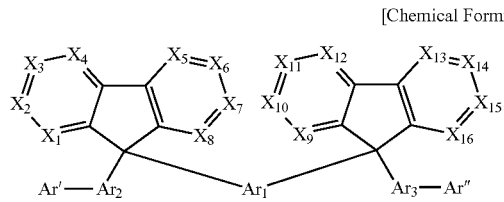

[Chemical Formula 1]

In the above Chemical Formula 1, $X_1$ to $X_{16}$ are the same or different, and are independently selected from CR' or N, $Ar_1$ to $Ar_3$ are the same or different, and are independently selected from a single bond, a substituted or unsubstituted C6 to C30 arylene group, or a substituted or unsubstituted C2 to C30 heteroarylene group, Ar' and Ar" are the same or different, and are independently selected from a substituted or unsubstituted C6 to C30 aryl group, or a substituted or unsubstituted C2 to C30 heteroaryl group, R' is independently selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, or a substituted or unsubstituted C3 to C40 silyl group.

In one embodiment, $Ar_1$ to $Ar_3$ are the same or different, and are independently selected from a substituted or unsubstituted carbazole, a substituted or unsubstituted arylamine, a substituted or unsubstituted phenyl, a substituted or unsubstituted tolyl, a substituted or unsubstituted naphthyl, a substituted or unsubstituted stilbene, a substituted or unsubstituted fluorenyl, a substituted or unsubstituted anthracenyl, a substituted or unsubstituted terphenyl, a substituted or unsubstituted pyrenyl, a substituted or unsubstituted diphenyl anthracenyl, a substituted or unsubstituted dinaphthylanthracenyl, a substituted or unsubstituted pentacenyl, a substituted or unsubstituted bromophenyl, a substituted or unsubstituted hydroxyphenyl, a substituted or unsubstituted thienyl, a substituted or unsubstituted pyridyl, a substituted or unsubstituted azobenzenyl, or a substituted or unsubstituted ferrocenyl.

In one embodiment, Ar' and Ar" are the same or different, and are independently selected from a substituted or unsubstituted carbazolyl, a substituted or unsubstituted arylamine, a substituted or unsubstituted phenyl, a substituted or unsubstituted naphthyl, a substituted or unsubstituted anthracenyl, a substituted or unsubstituted fluorene, a substituted or unsubstituted thiophene, a substituted or unsubstituted pyrrole, a substituted or unsubstituted pyridine, a substituted or unsubstituted aryloxadiazole, a substituted or unsubstituted triazole, or a substituted or unsubstituted arylsilane.

As used herein, the substituted arylene and substituted heteroarylene respectively refer to an arylene and a heteroarylene substituted with a C1 to C30 alkyl, a halogen, a C1 to C30 haloalkyl, a C6 to C30 aryl, or C2 to C30 heteroaryl.

As used herein, the substituted alkyl, substituted alkenyl, substituted aryl, substituted heteroaryl, substituted alkoxy, substituted aryl oxy, substituted hetero oxy, substituted silyl oxy, substituted acyl, substituted alkoxy carbonyl, substituted acyl oxy, substituted acyl amino, substituted alkoxy carbonyl amino, substituted aryloxycarbonylamino, substituted sulfamoyl amino, substituted sulfonyl, substituted alkylthiol, substituted aryl thiol, substituted hetero cycloalkyl thiol, substituted ureide, substituted phosphoric acid amide, and substituted silyl respectively refer to an alkyl, alkenyl, an aryl, a heteroaryl, an alkoxy, an aryl oxy, a heterooxy, a silyl oxy, an acyl, an alkoxy carbonyl, an acyl oxy, an acyl amino, an alkoxy carbonyl amino, an aryloxycarbonylamino, a sulfamoyl amino, a sulfonyl, an alkylthiol, an aryl thiol, a hetero cycloalkyl thiol, a ureide, a phosphoric acid amide, and silyl substituted with C1 to C30 alkyl, a halogen, a C1 to C30 haloalkyl, a C6 to C30 aryl, or a C2 to C30 heteroaryl.

As used herein, the substituted carbazole, substituted arylamine, substituted phenyl, substituted tolyl, substituted naphthyl, substituted stilbene, substituted fluorenyl, substituted anthracenyl, substituted terphenyl, substituted pyrenyl, substituted diphenylanthracenyl, substituted dinaphthylanthracenyl, substituted pentacenyl, substituted bromophenyl, substituted hydroxyphenyl, substituted thienyl, substituted pyridyl, substituted azobenzenyl, and substituted ferrocenyl refers to a carbazole, an arylamine, a phenyl, a tolyl, a naphthyl, a stilbene, a fluorenyl, an anthracenyl, a terphenyl, a pyrenyl, a diphenylanthracenyl, a dinaphthylanthracenyl, a pentacenyl, a bromophenyl, a hydroxyphenyl, a thienyl, a pyridyl, an azobenzenyl, and a ferrocenyl substituted with a C1 to C30 alkyl, a halogen, a C1 to C30 haloalkyl, a C6 to C30 aryl, or C2 to C30 heteroaryl.

As used herein, the substituted thiophene, substituted pyrrole, substituted pyridine, substituted aryloxadiazole, substituted triazole, and substituted arylsilane refer to a thiophene, a pyrrole, a pyridine, an aryloxadiazole, a triazole and an arylsilane substituted with a C1 to C30 alkyl, a halogen, a C1 to C30 haloalkyl, a C6 to C30 aryl, or C2 to C30 heteroaryl.

In the present specification, the term "hetero" refers to one including 1 to 3 heteroatoms selected from nitrogen (N), oxygen (O), sulfur (S), or phosphorus (P), and the remainder being carbon.

Ar' and Ar" are the same or different, and are independently selected from the substituents of the following Chemical Formulae 2 to 31:

[Chemical Formula 2]

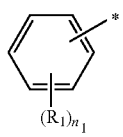

[Chemical Formula 3]

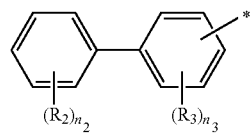

[Chemical Formula 4]

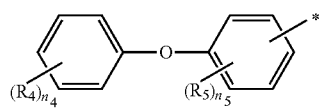

[Chemical Formula 5]

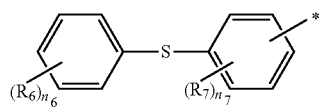

[Chemical Formula 6]

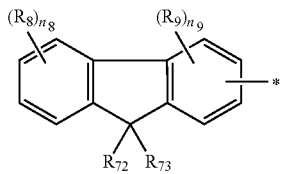

[Chemical Formula 7]

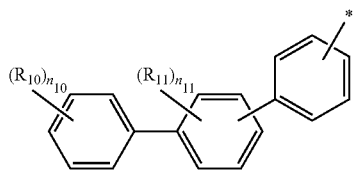

[Chemical Formula 8]

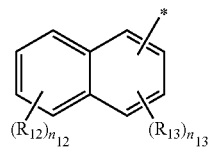

[Chemical Formula 9]

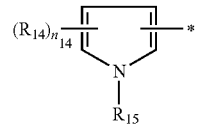

[Chemical Formula 10]

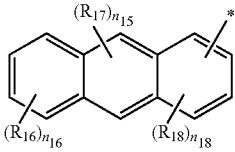

[Chemical Formula 11]

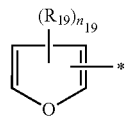

[Chemical Formula 12]

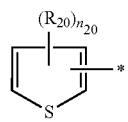

[Chemical Formula 13]

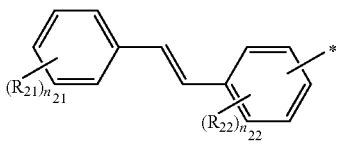

[Chemical Formula 14]

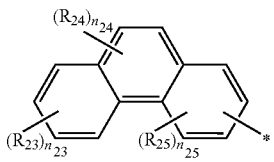

[Chemical Formula 15]

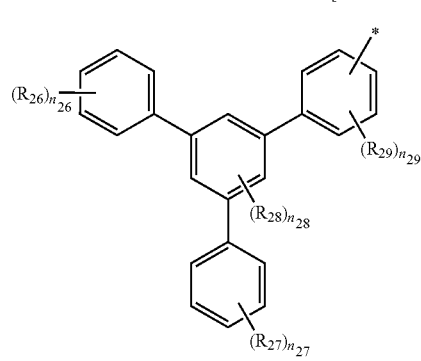

[Chemical Formula 16]

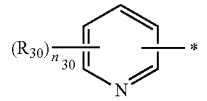

[Chemical Formula 17]
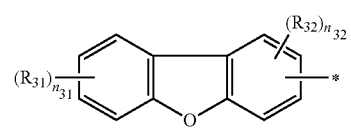
[Chemical Formula 18]
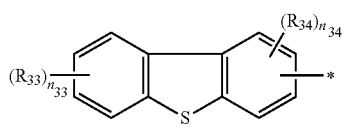
[Chemical Formula 19]
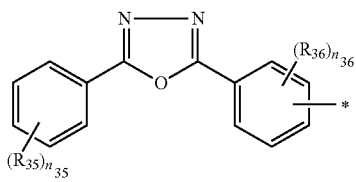
[Chemical Formula 20]
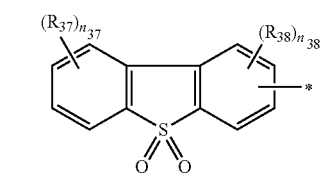
[Chemical Formula 21]
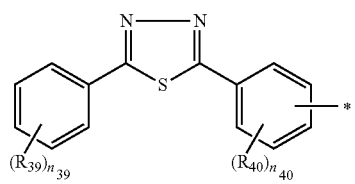
[Chemical Formula 22]
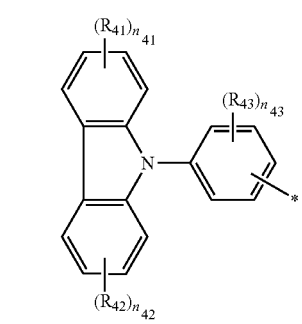
[Chemical Formula 23]
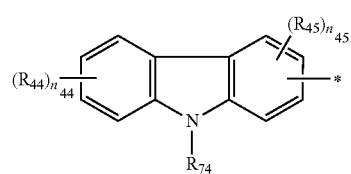
[Chemical Formula 24]
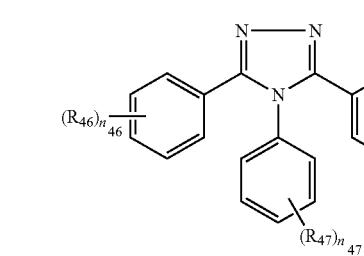
[Chemical Formula 25]
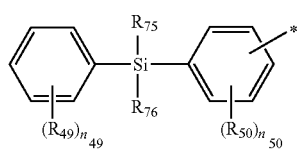
[Chemical Formula 26]
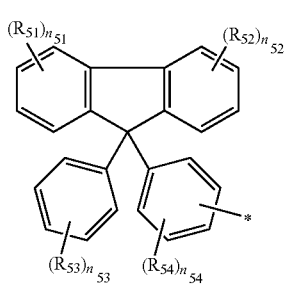
[Chemical Formula 27]
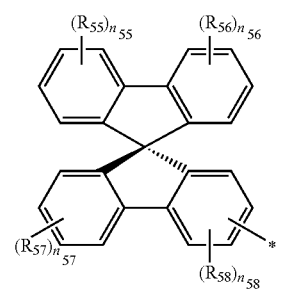
[Chemical Formula 28]
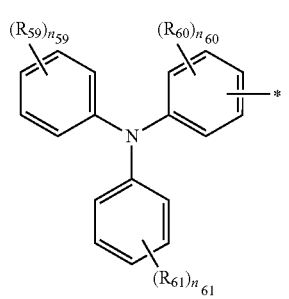
[Chemical Formula 29]
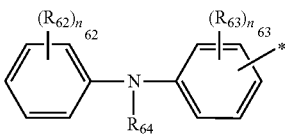
[Chemical Formula 30]
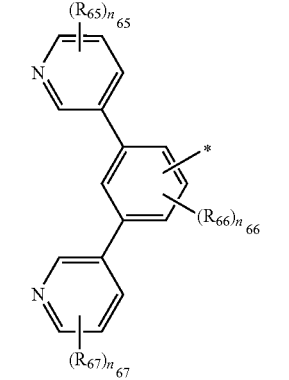

[Chemical Formula 31]

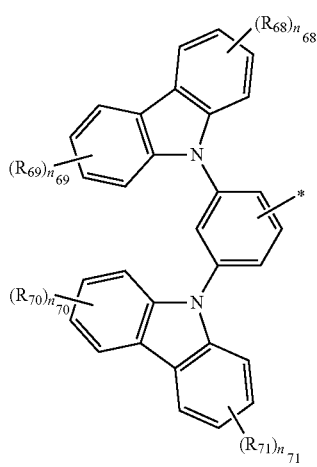

[Chemical Formula B-1]

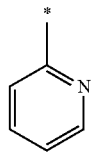

[Chemical Formula B-2]

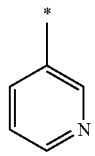

[Chemical Formula B-3]

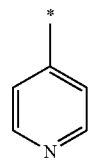

[Chemical Formula B-4]

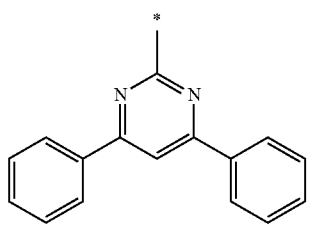

[Chemical Formula B-5]

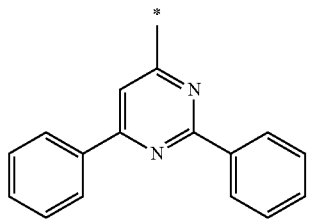

[Chemical Formula B-6]

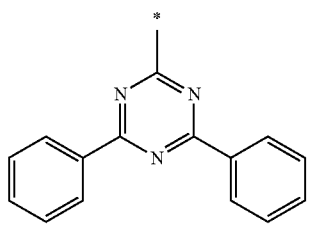

In the above Chemical Formulae 2 to 31, $R_1$ to $R_{76}$ are the same or different, and are independently selected from a halogen, a cyano group, a hydroxyl group, an amino group, a nitro group, a carboxyl group, a substituted or unsubstituted C1 to C20 alkyl group, a substituted or unsubstituted C2 to C20 alkenyl, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyl oxy group, a substituted or unsubstituted C1 to C20 acyl group, a substituted or unsubstituted C2 to C20 alkoxy carbonyl group, a substituted or unsubstituted C2 to C20 acyl oxy group, a substituted or unsubstituted C2 to C20 acyl amino group, a substituted or unsubstituted C2 to C20 alkoxy carbonyl amino group, a substituted or unsubstituted C7 to C20 aryloxycarbonylamino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 aryl thiol group, a substituted or unsubstituted C1 to C20 hetero cycloalkyl thiol group, a substituted or unsubstituted C1 to C20 ureide group, a substituted or unsubstituted C1 to C20 phosphoric acid amide group, or a substituted or unsubstituted C3 to C40 silyl group, $n_1$, $n_2$, $n_4$, $n_6$, $n_{10}$, $n_{21}$, $n_{26}$, $n_{27}$, $n_{35}$, $n_{39}$, $n_{46}$, $n_{47}$, $n_{49}$, $n_{53}$, $n_{59}$, $n_{61}$, and $n_{62}$ are the same or different, and are independently integers ranging from 0 to 5, $n_3$, $n_5$, $n_7$, $n_8$, $n_{11}$, $n_{12}$, $n_{16}$, $n_{22}$, $n_{23}$, $n_{29}$, $n_{30}$, $n_{31}$, $n_{33}$, $n_{36}$, $n_{37}$, $n_{40}$, $n_{41}$ to $n_{44}$, $n_{48}$, $n_{50}$ to $n_{52}$, $n_{54}$, $n_{55}$, $n_{57}$, $n_{56}$, $n_{60}$, $n_{63}$, $n_{65}$, $n_{67}$, $n_{68}$, $n_{69}$, $n_{70}$, and $n_{71}$ are the same or different, and are independently integers ranging from 0 to 4, $n_9$, $n_{13}$, $n_{14}$, $n_{18}$, $n_{19}$, $n_{20}$, $n_{25}$, $n_{28}$, $n_{32}$, $n_{34}$, $n_{38}$, $n_{45}$, $n_{58}$, and $n_{66}$ are the same or different, and are independently integers ranging from 0 to 3, and $n_{15}$ and $n_{24}$ are the same or different, and are independently integers ranging from 0 to 2.

Ar' and Ar'' are the same or different and independently a substituent selected from the following Chemical Formulae B-1 to B-9.

[Chemical Formula B-7]
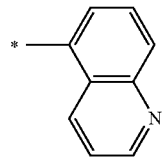
[Chemical Formula B-8]
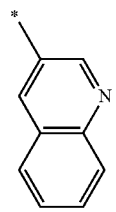
[Chemical Formula B-9]
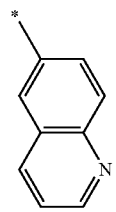
The compound represented by the above Chemical Formula 1 may be one of the compounds represented by the following Chemical Formulae 32 to 37.
[Chemical Formula 32]
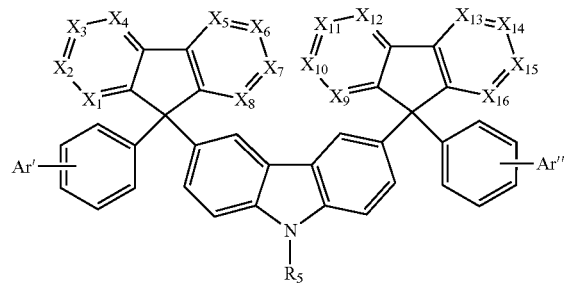
[Chemical Formula 33]
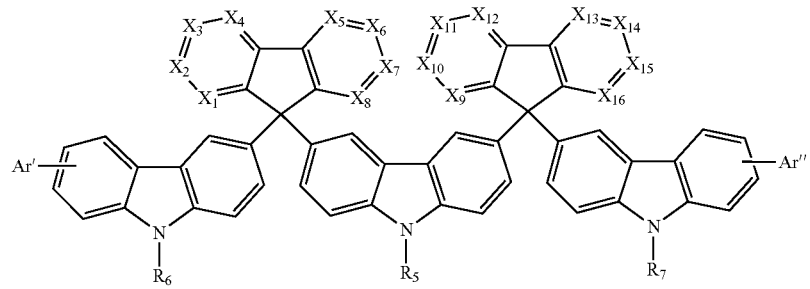
[Chemical Formula 34]
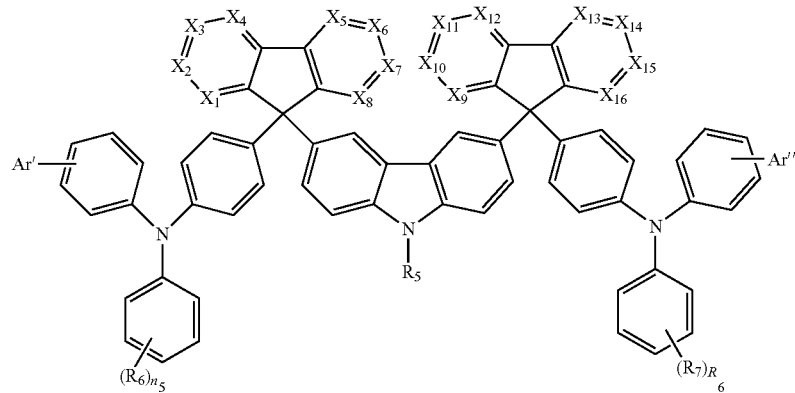

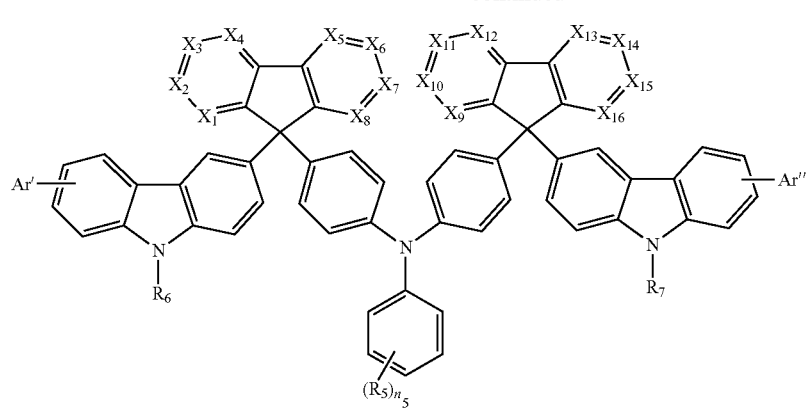

[Chemical Formula 35]

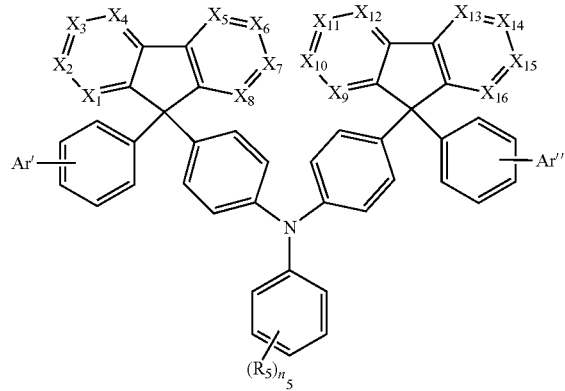

[Chemical Formula 36]

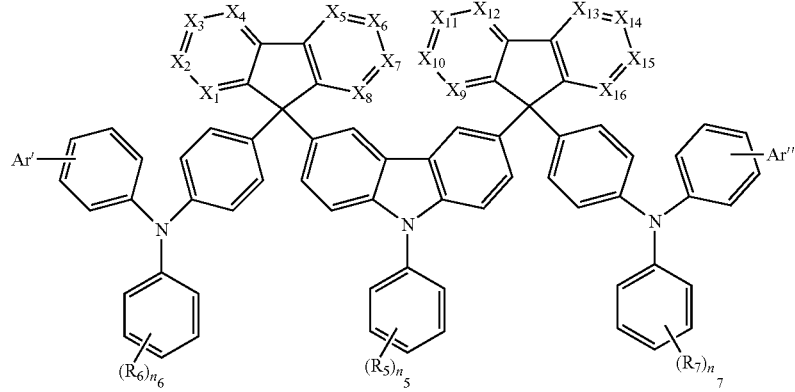

[Chemical Formula 37]

In the above Chemical Formulae 32 to 37, $X_1$ to $X_{16}$ are the same or different, and are independently selected from CR' or N, Ar' and Ar" are the same or different, and are independently selected from a substituted or unsubstituted C6 to C30 aryl group, or a substituted or unsubstituted C2 to C30 heteroaryl group, $R_5$ to $R_7$ and R' are the same or different, and are independently selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, or a substituted or unsubstituted C3 to C40 silyl group, and $n_5$ to $n_7$ are independently integers ranging from 0 to 5.

The compound represented by the above Chemical Formulae 31 to 36 may be the compound represented by the following Chemical Formulae 38 to 126.

[Chemical Formula 38]

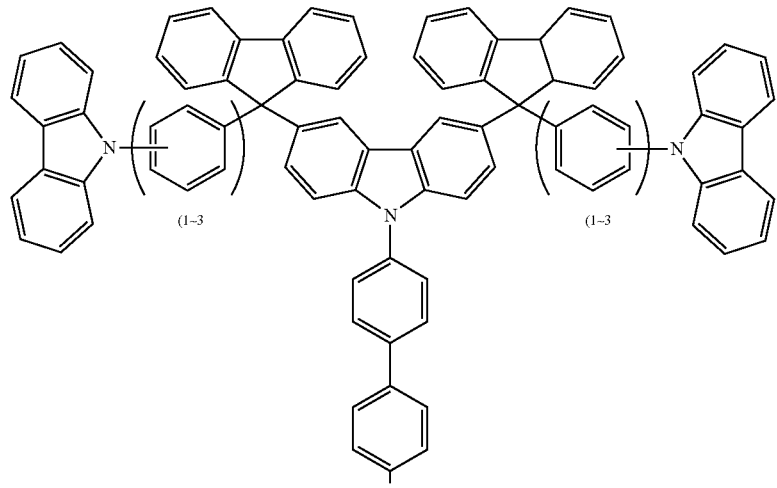

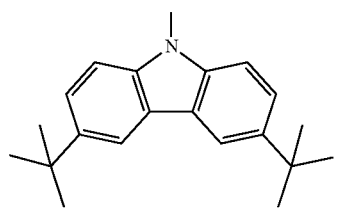

[Chemical Formula 39]

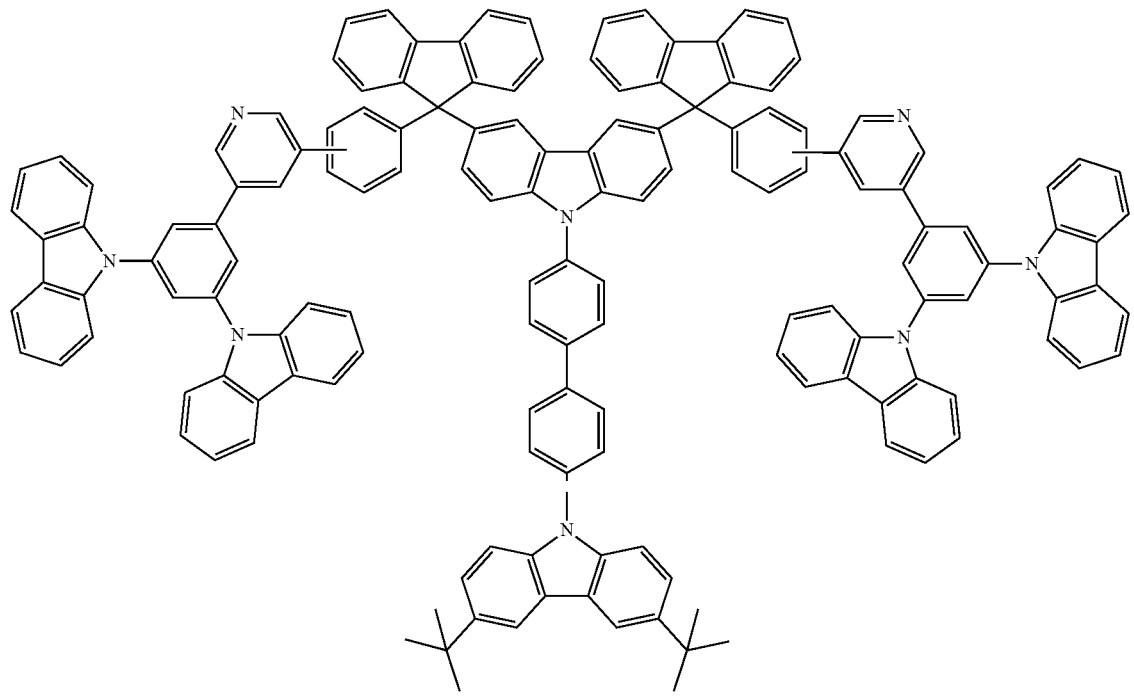

[Chemical Formula 40]
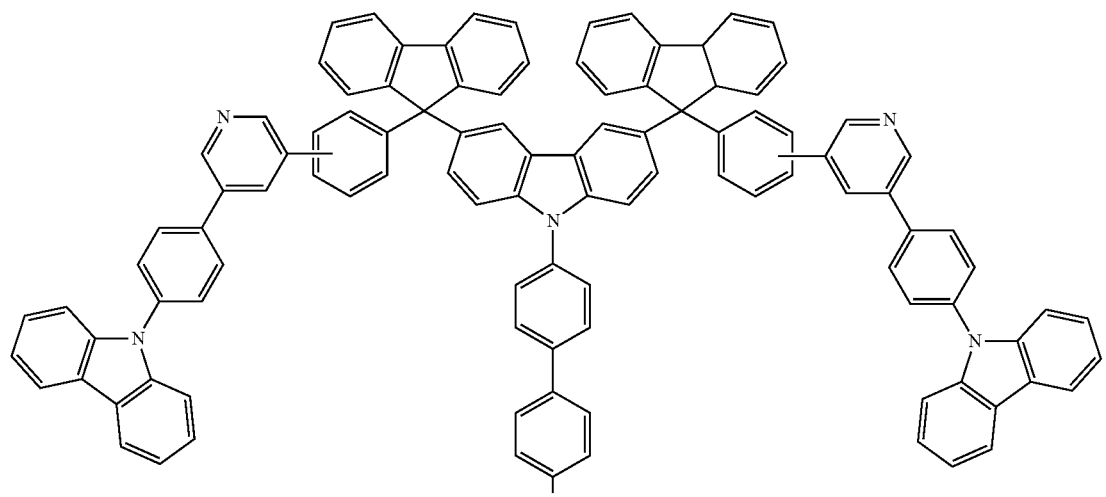
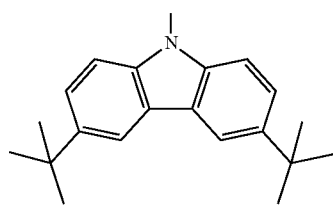
[Chmeical Formula 41]
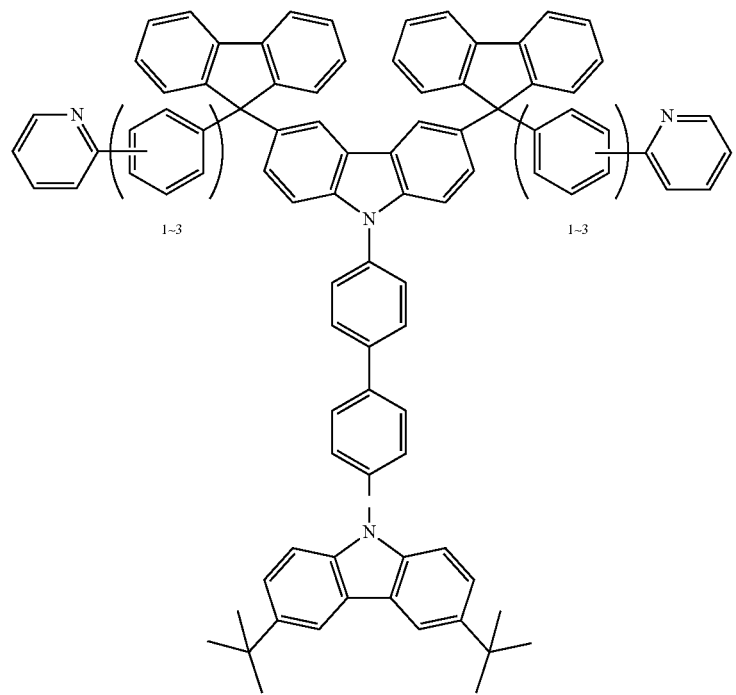

[Chemical Formula 42]
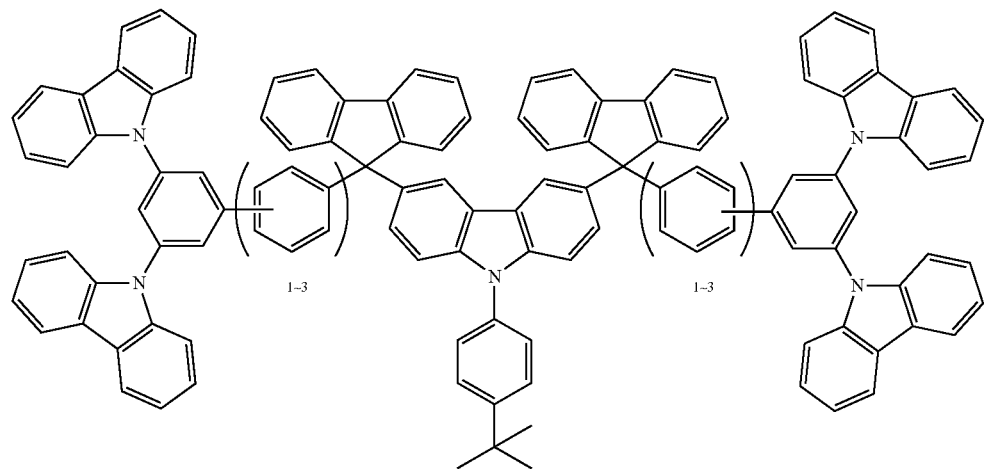
[Chemical Formula 43]
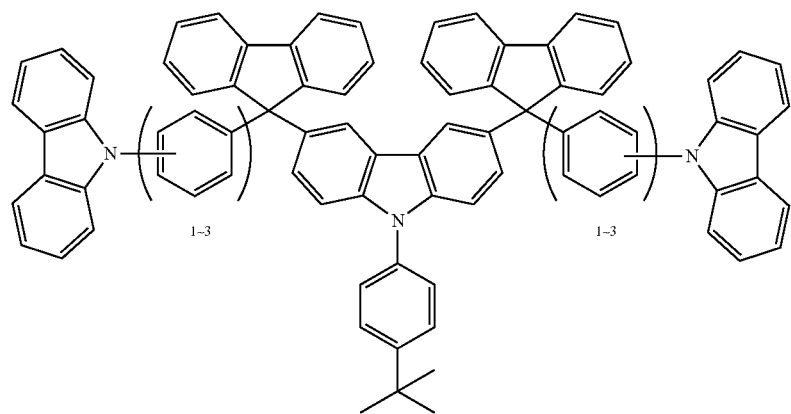
[Chemical Formula 44]
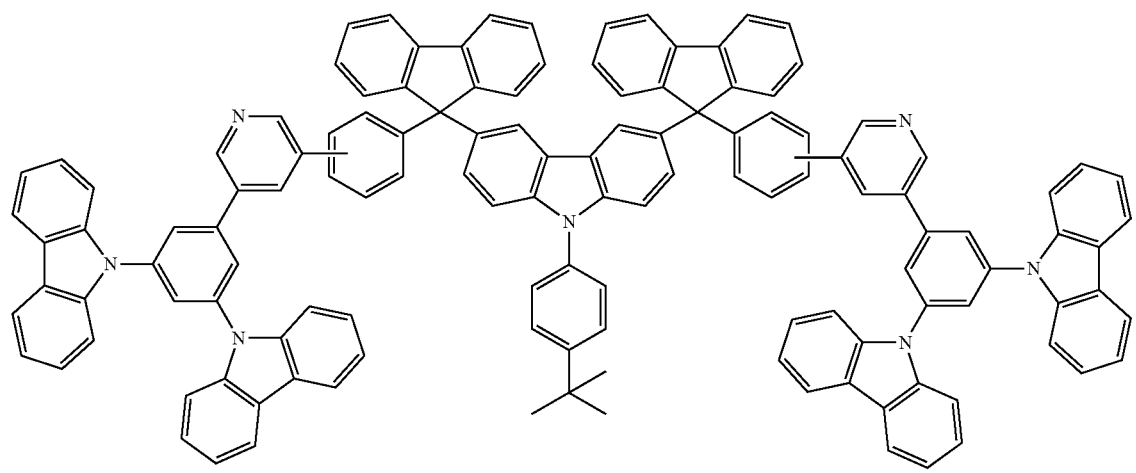

[Chemical Formula 45]
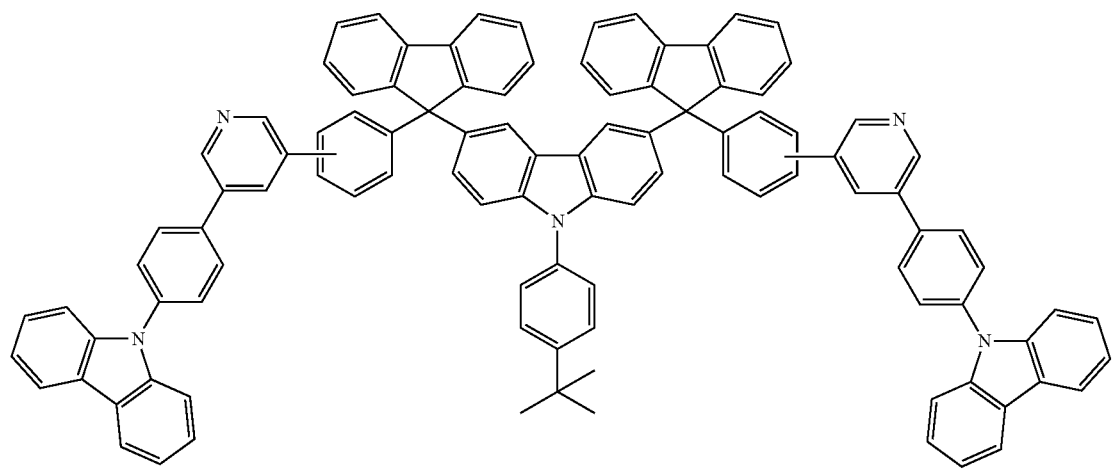
[Chemical Formula 46]
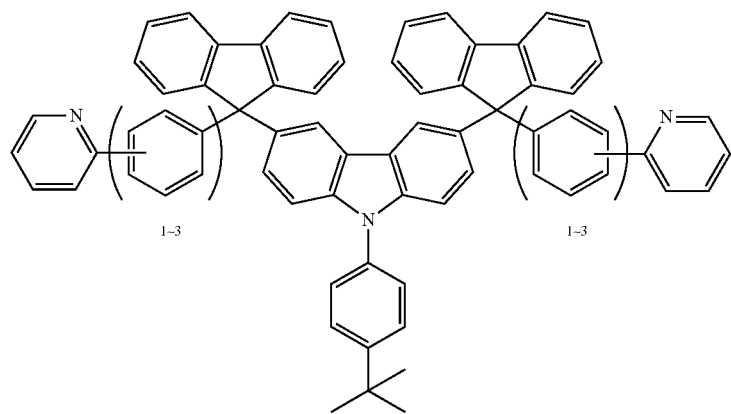
[Chemical Formula 47]
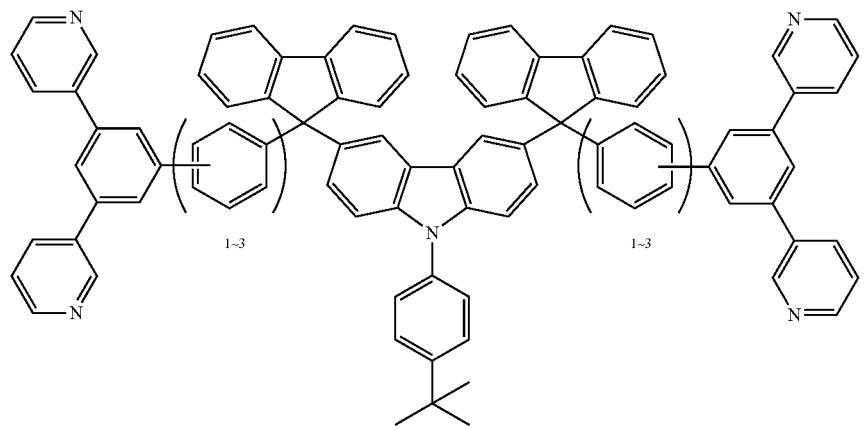

[Chemical Formula 48]
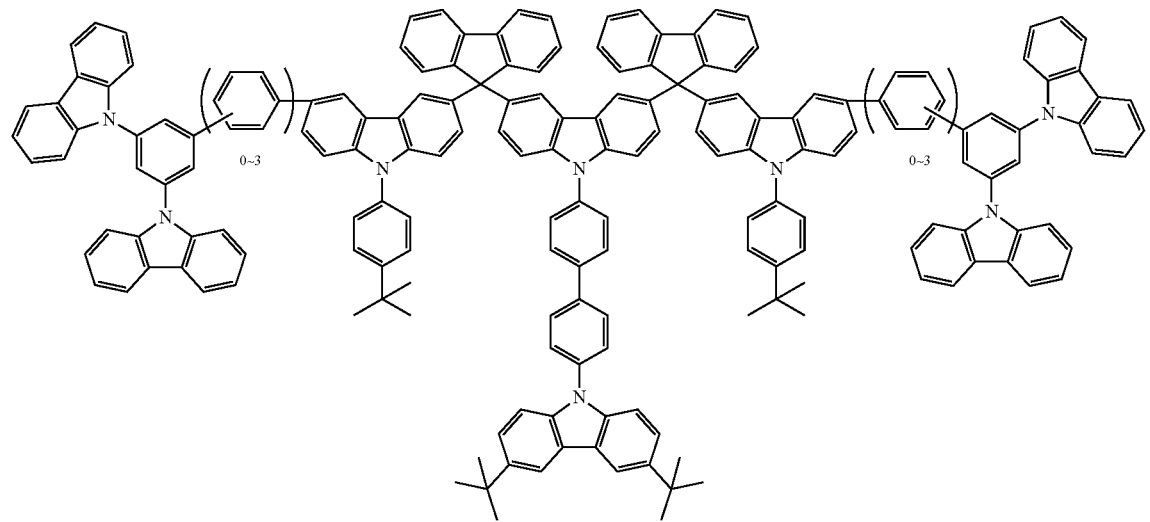
[Chemical Formula 49]
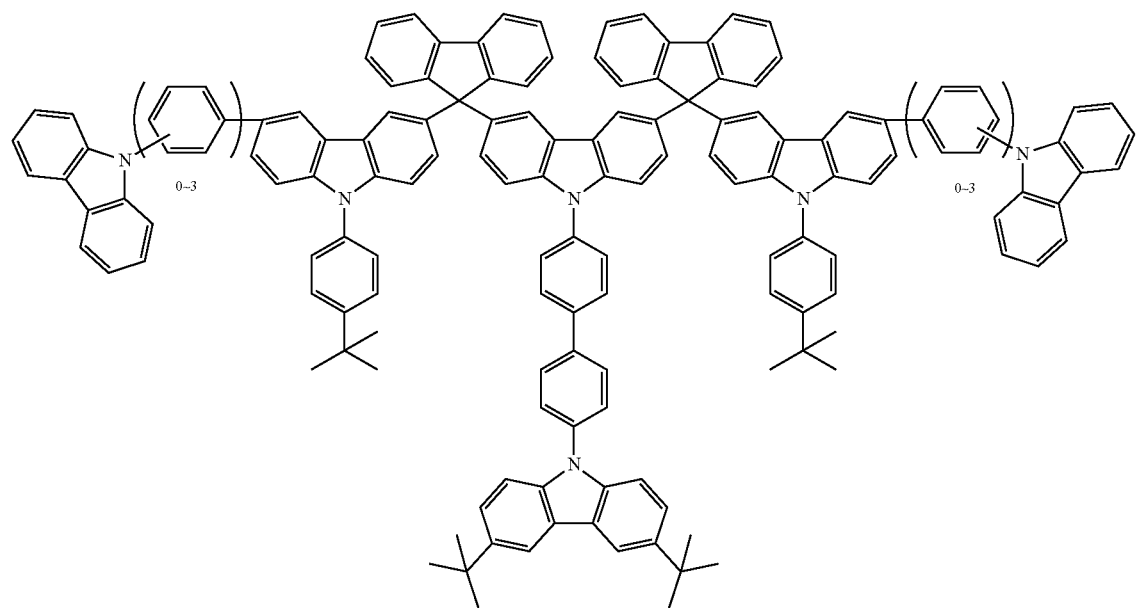

[Chemical Formula 50]
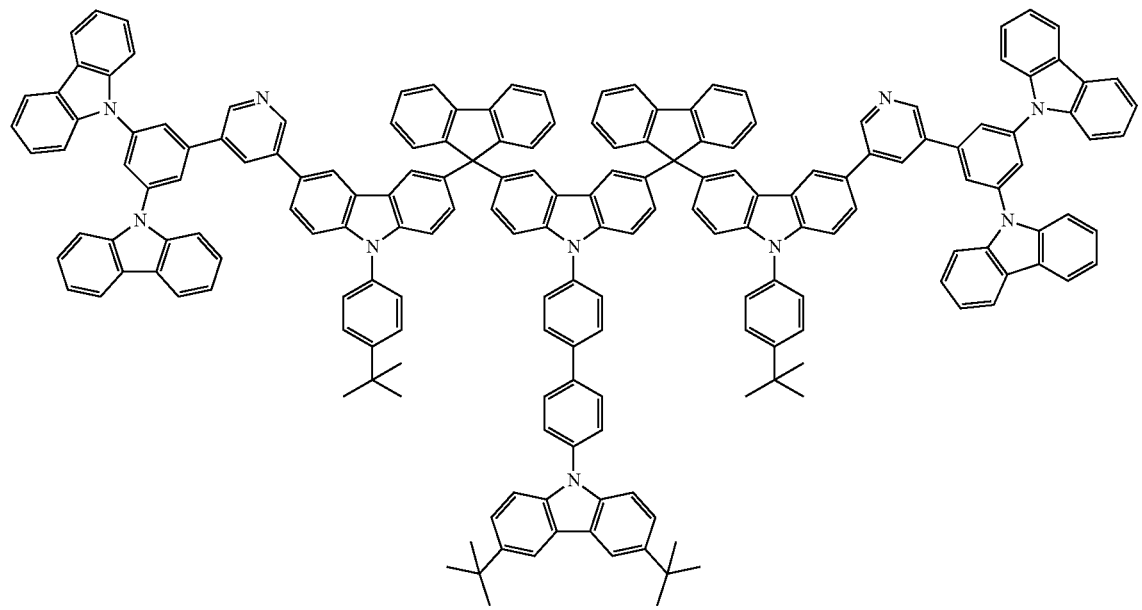
[Chemical Formula 51]
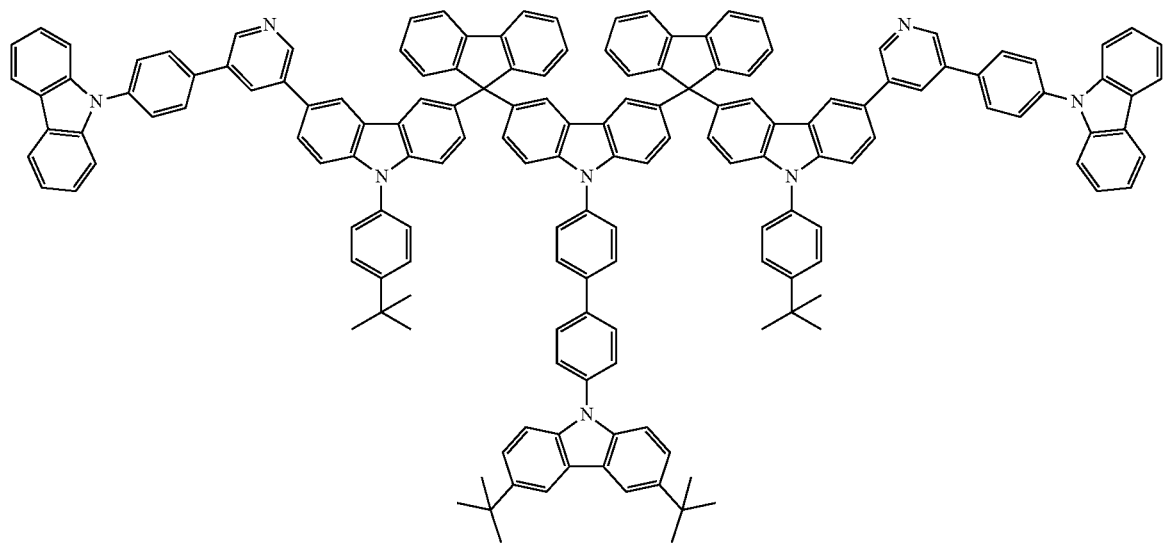

[Chemical Formula 52]
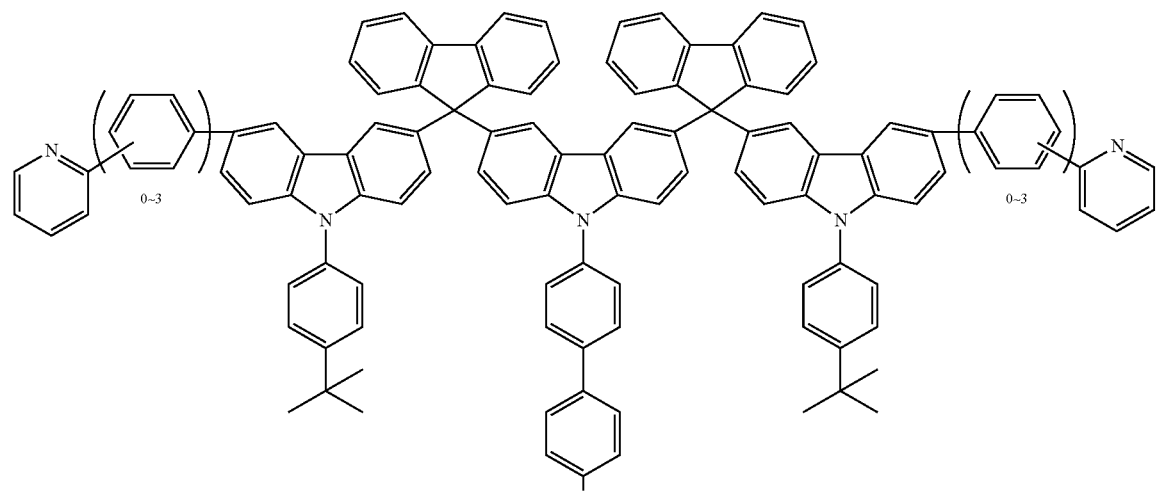
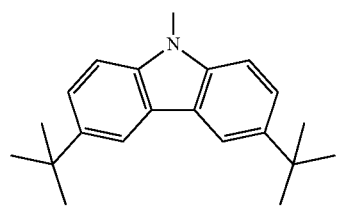
[Chemical Formula 53]
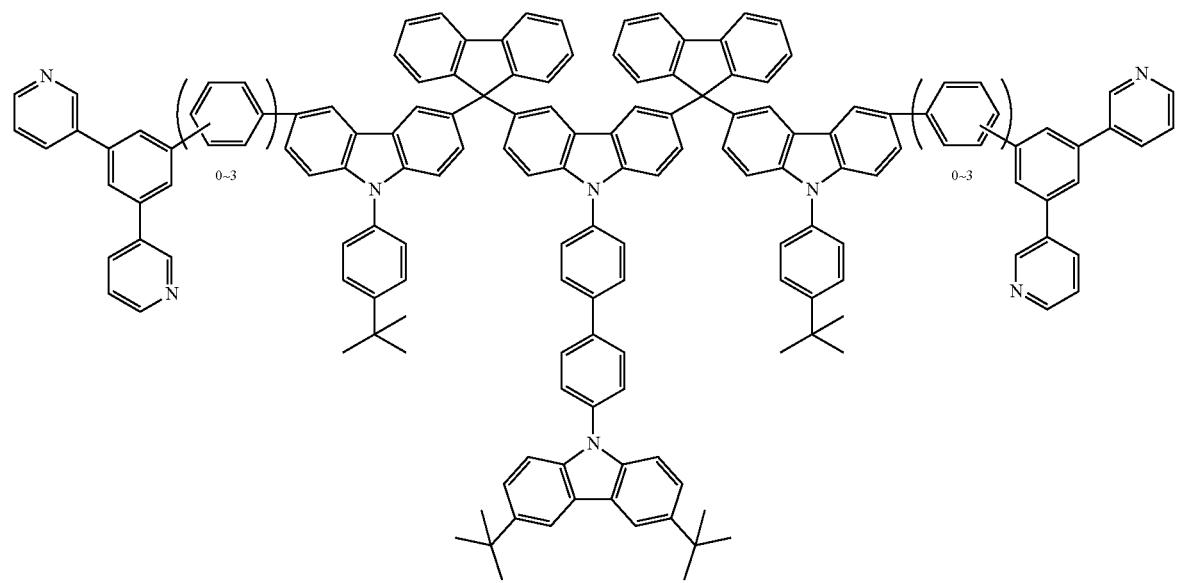

[Chemical Formula 54]
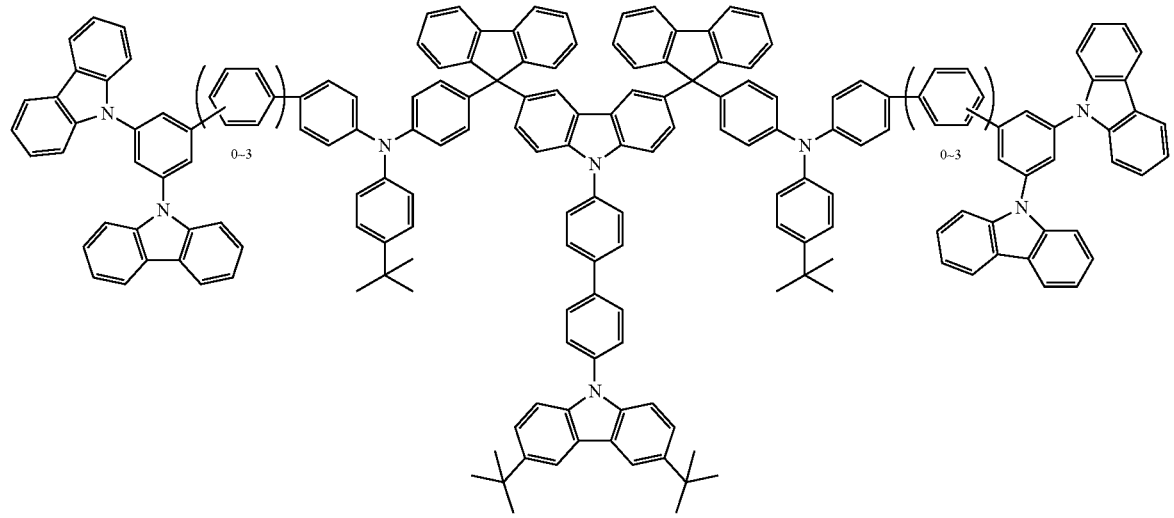
[Chemical Formula 55]
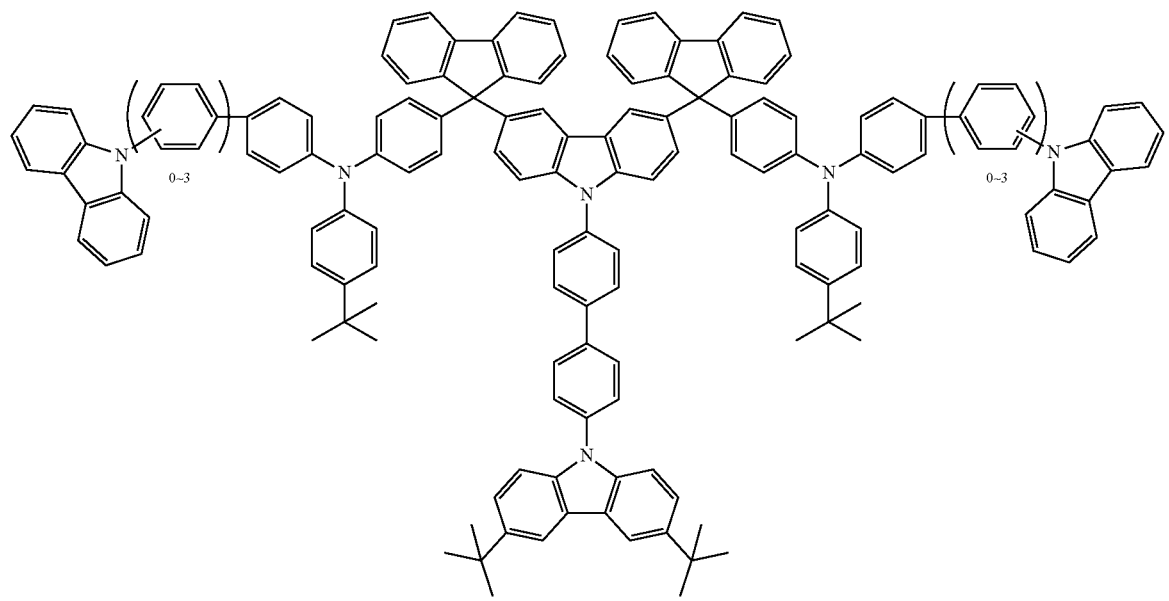
[Chemical Formula 56]
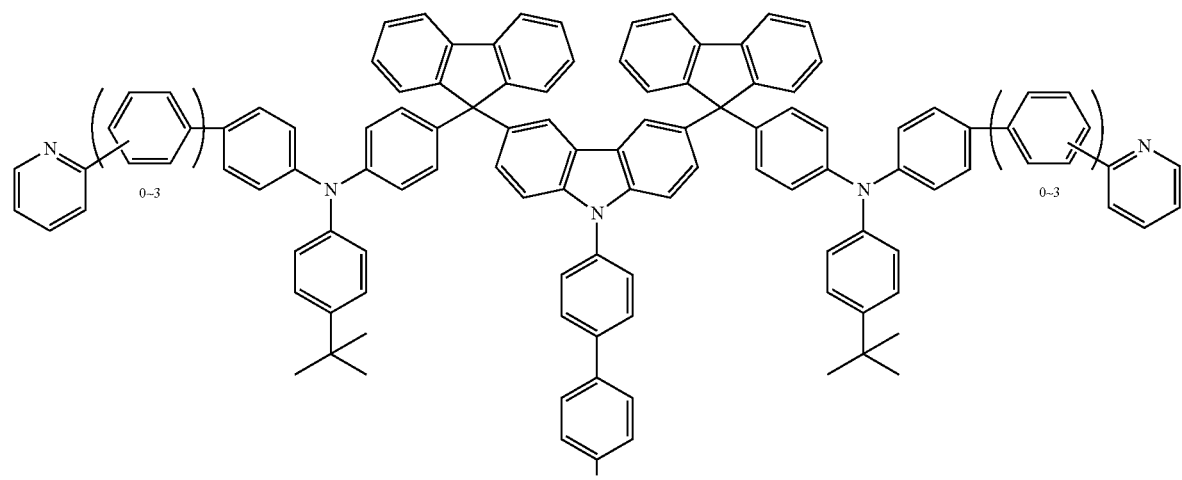

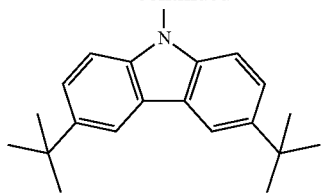
[Chemical Formula 57]
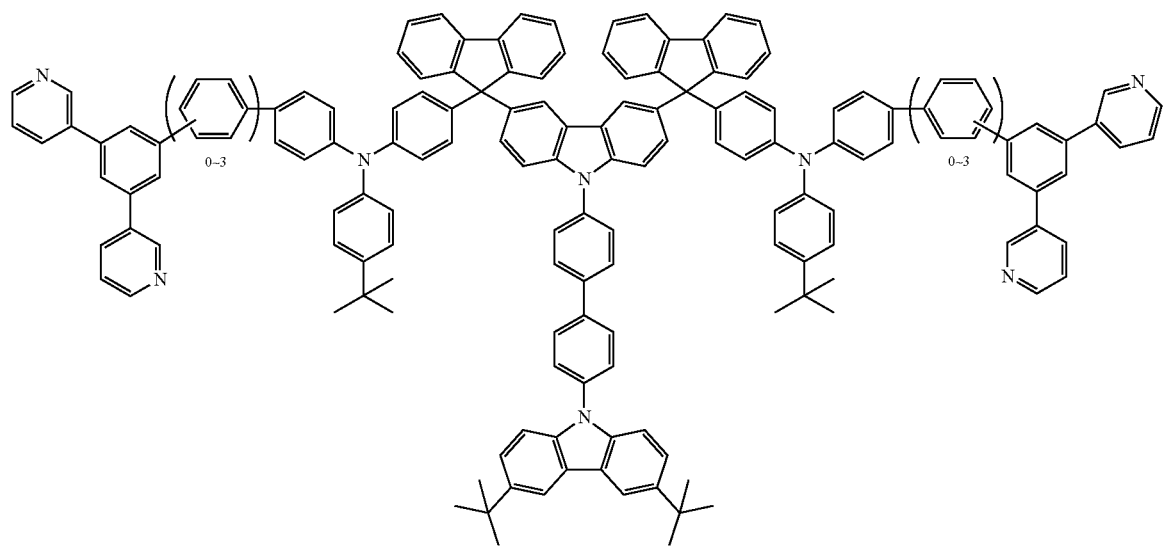
[Chemical Formula 58]
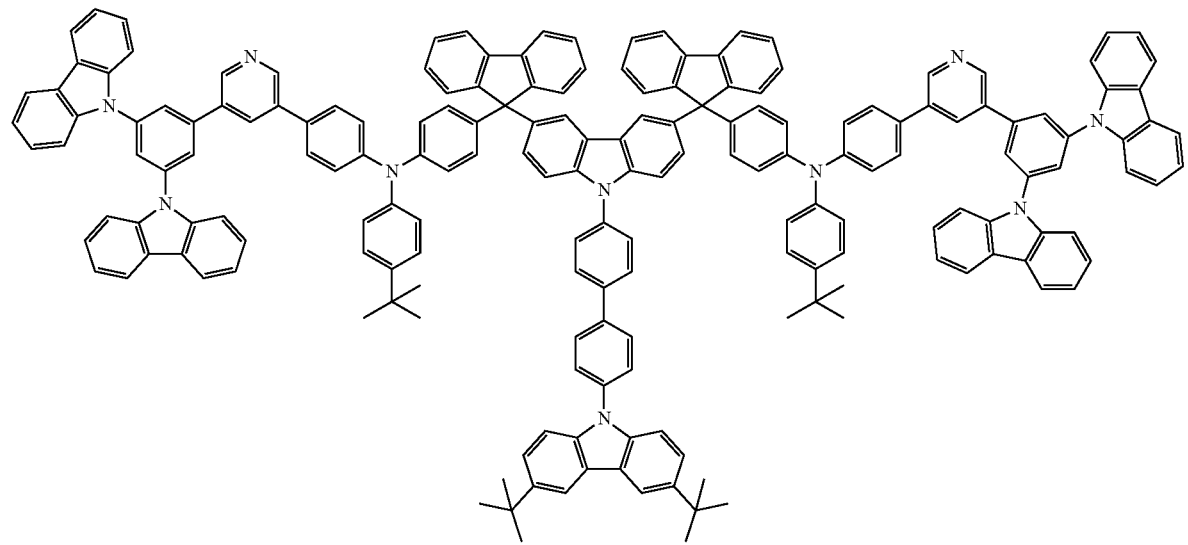

[Chemical Formula 59]
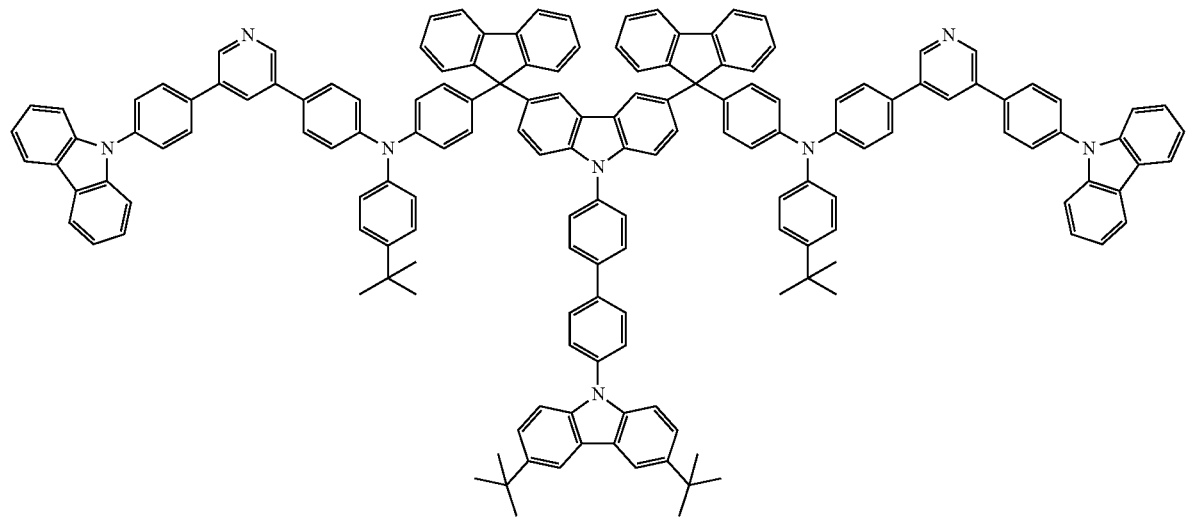
[Chemical Formula 60]
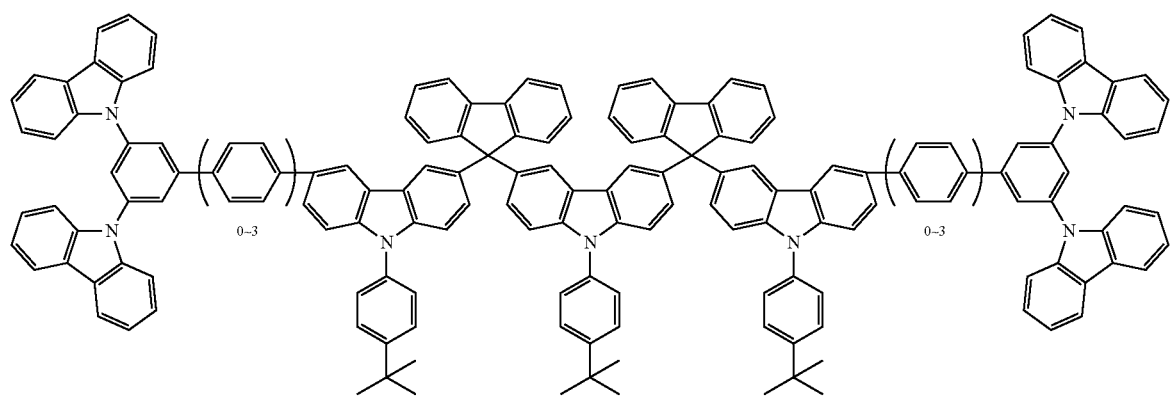
[Chemical Formula 61]
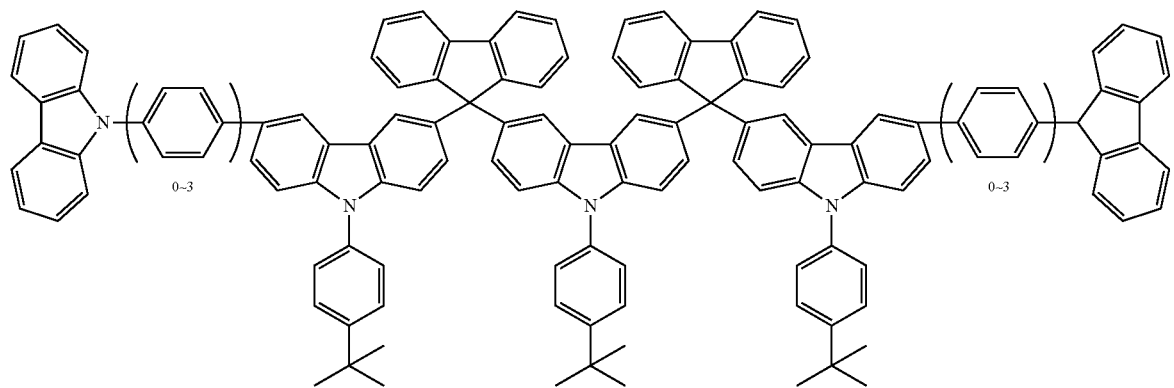

[Chemical Formula 62]
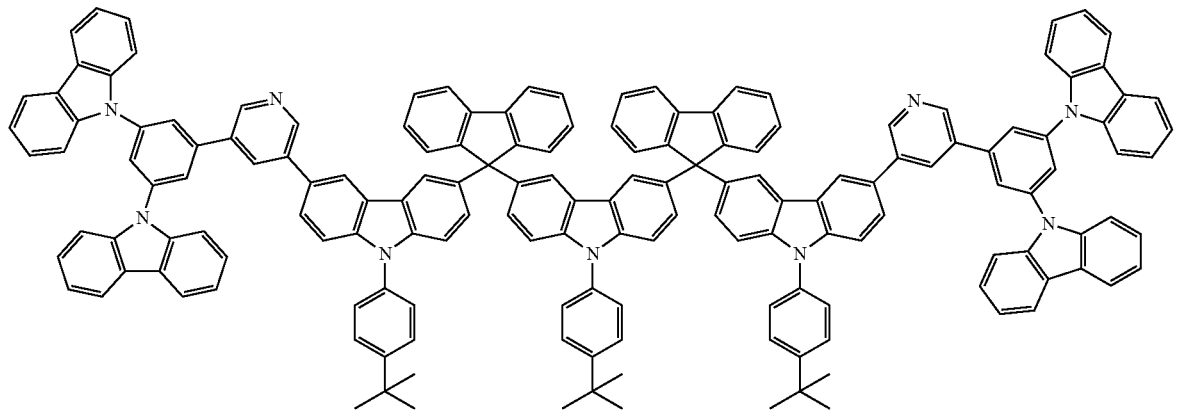
[Chemical Formula 63]
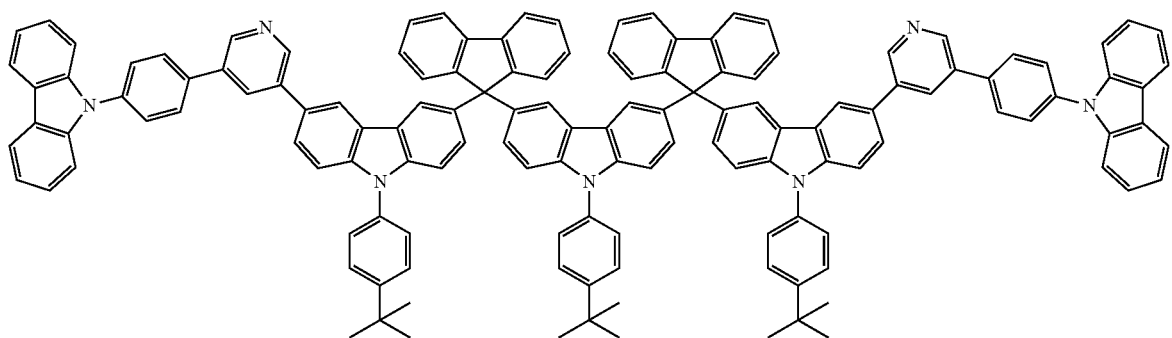
[Chemical Formula 64]
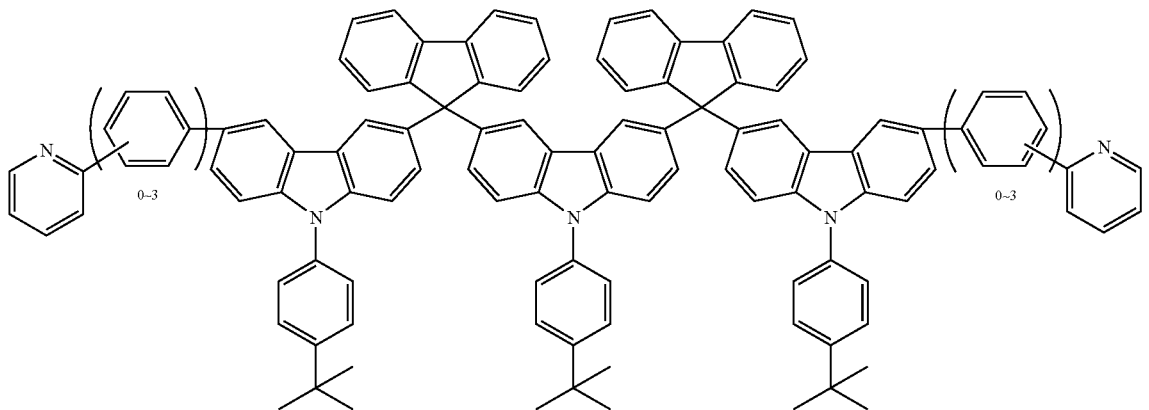
[Chemical Formula 65]
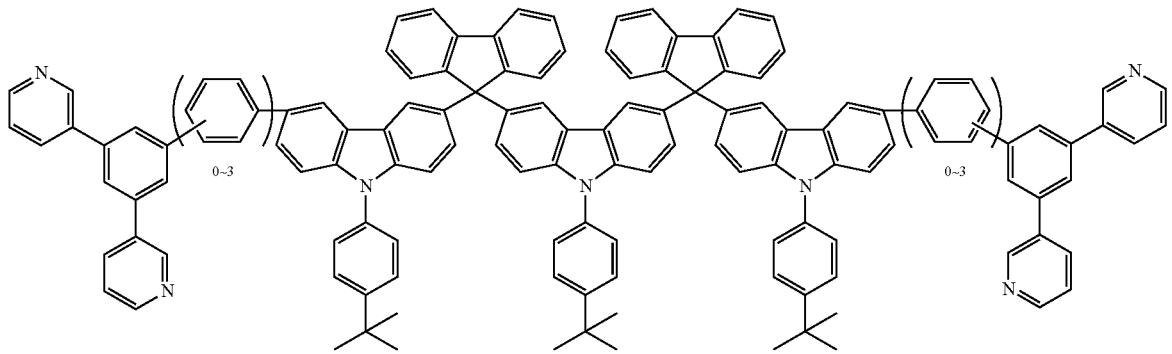

[Chemical Formula 66]
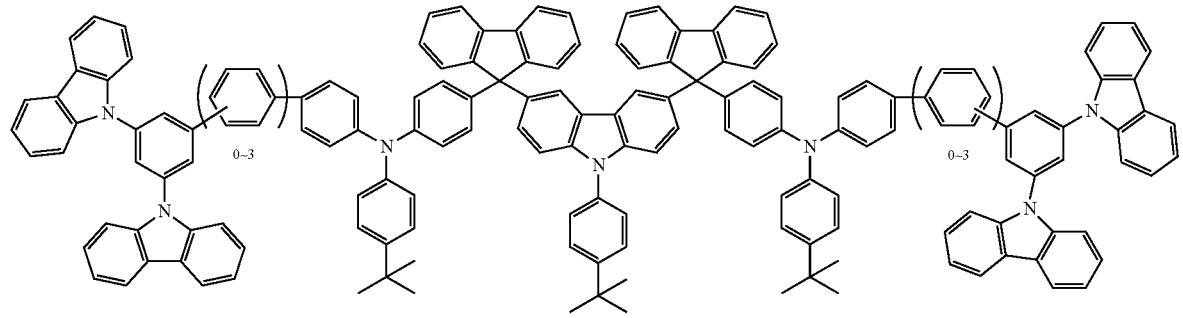
[Chemical Formula 67]
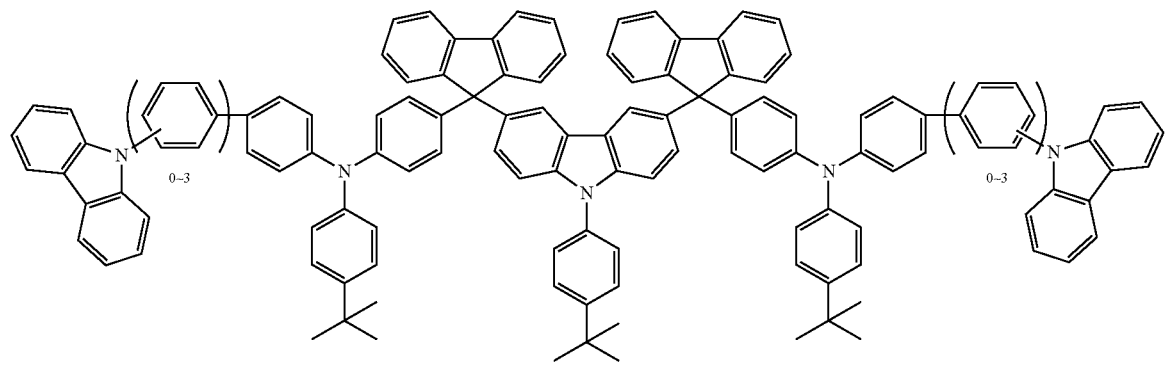
[Chemical Formula 68]
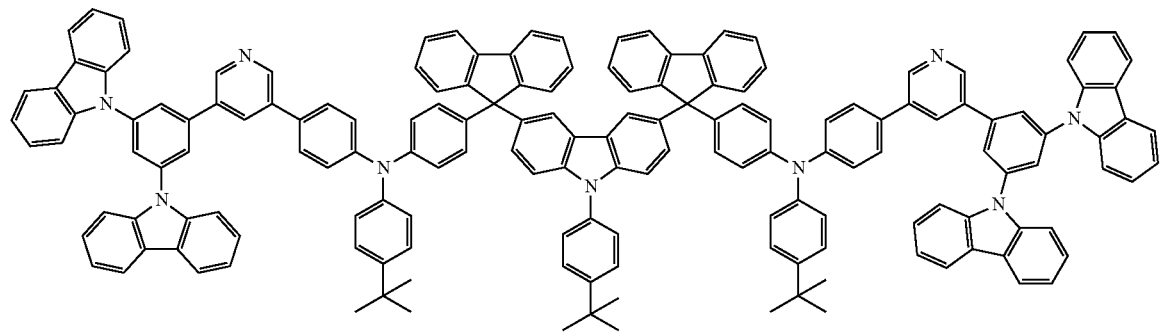
[Chemical Formula 69]
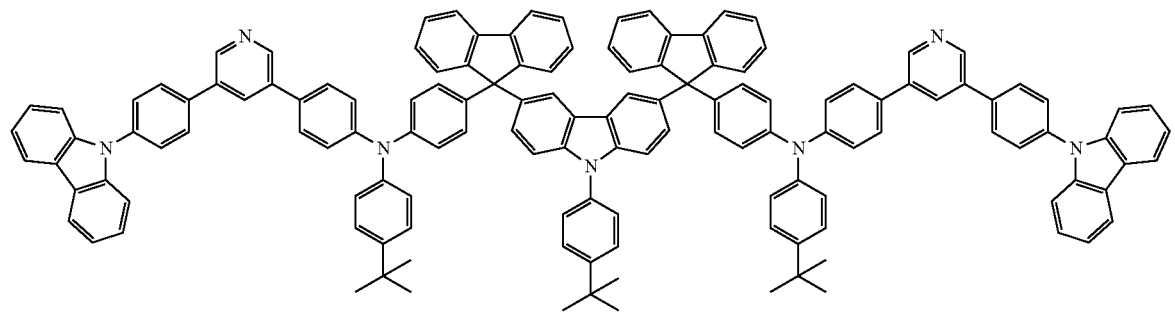

[Chemical Formula 70]
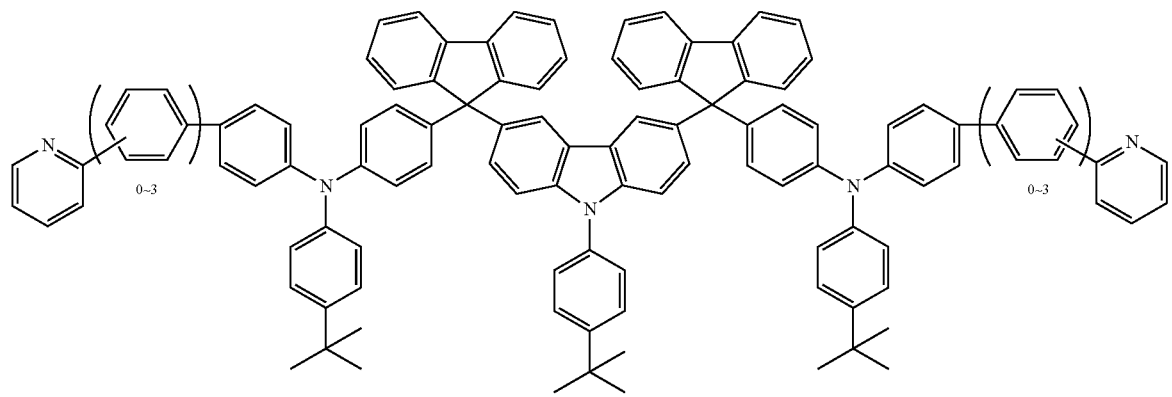
[Chemical Formula 71]
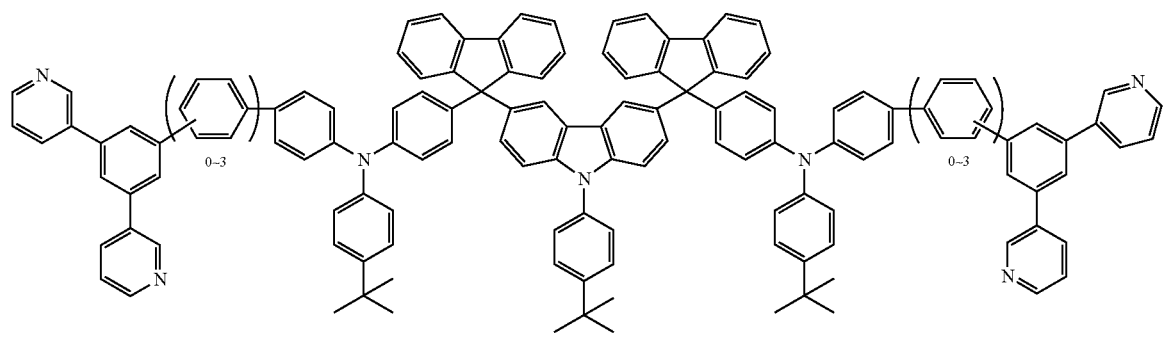
[Chemical Formula 72]
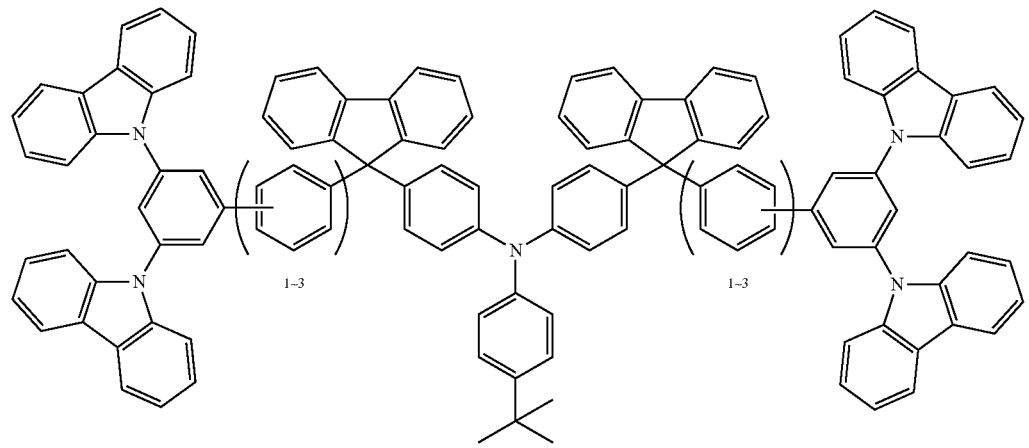
[Chemical Formula 73]
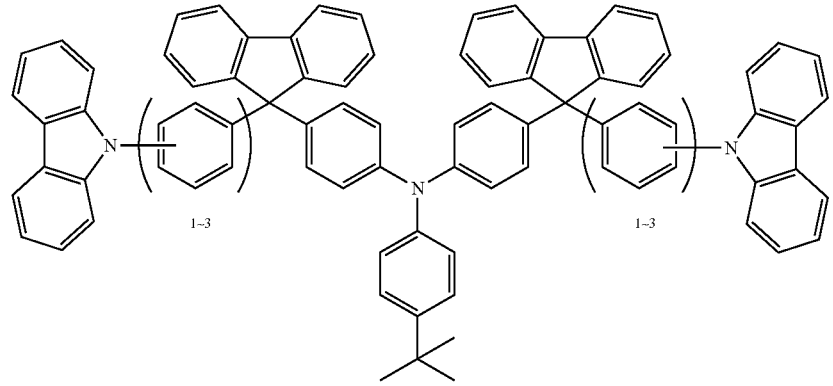

[Chemical Formula 74]
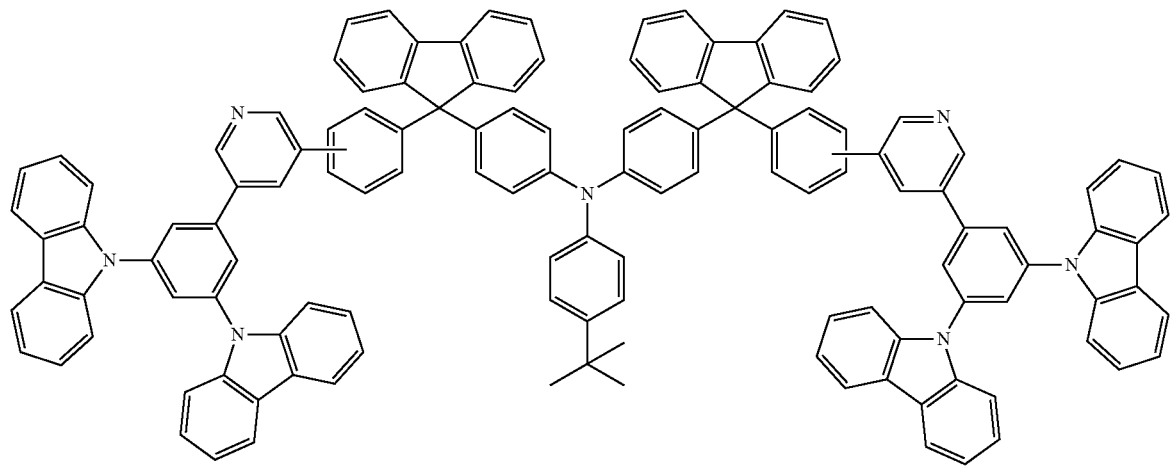
[Chemical Formula 75]
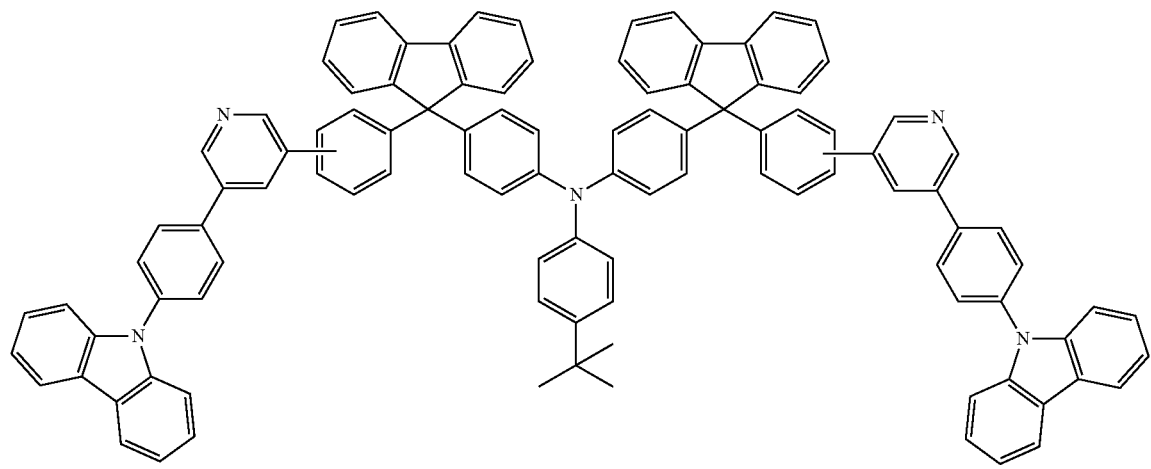
[Chemical Formula 76]
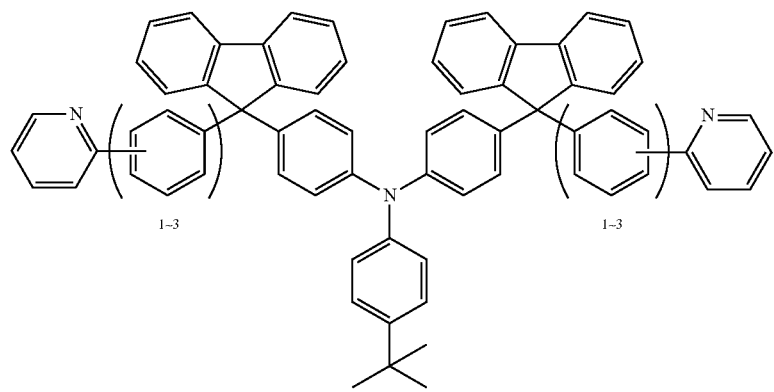

[Chemical Formula 77]
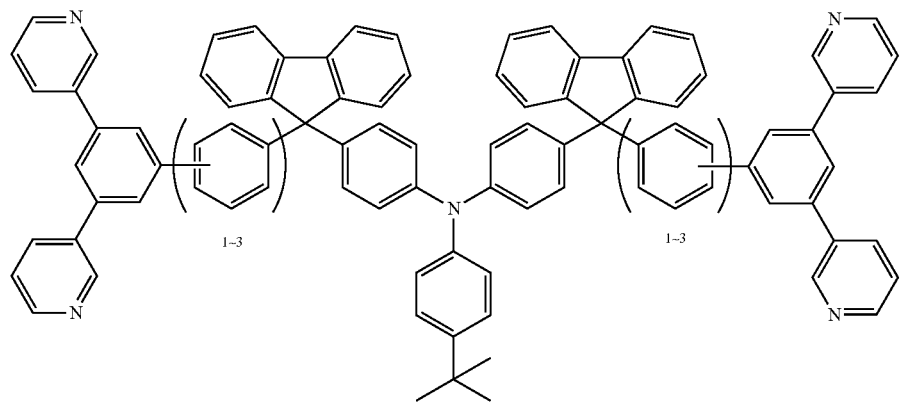
[Chemical Formula 78]
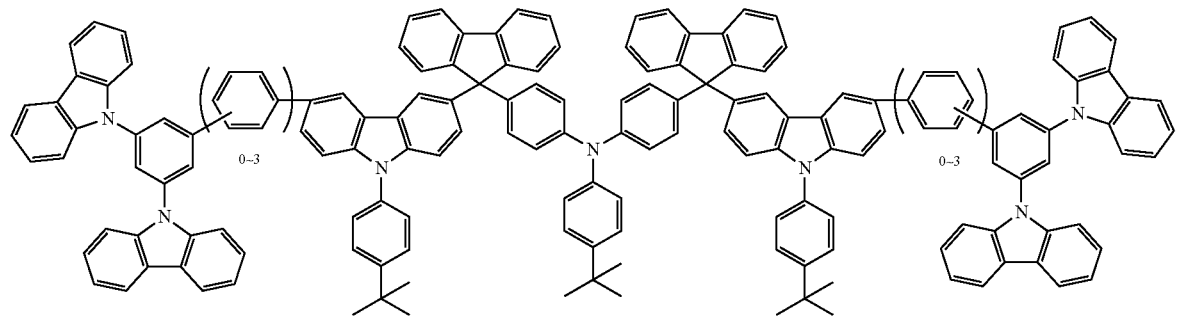
[Chemical Formula 79]
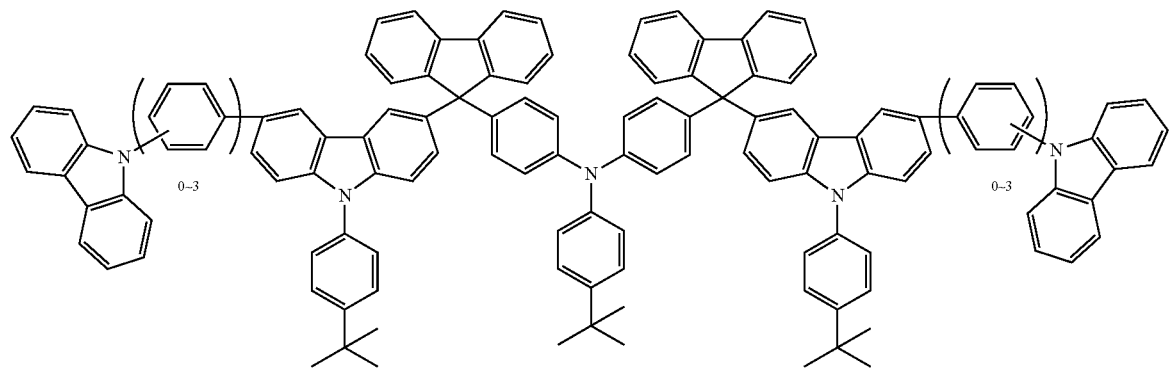
[Chemical Formula 80]
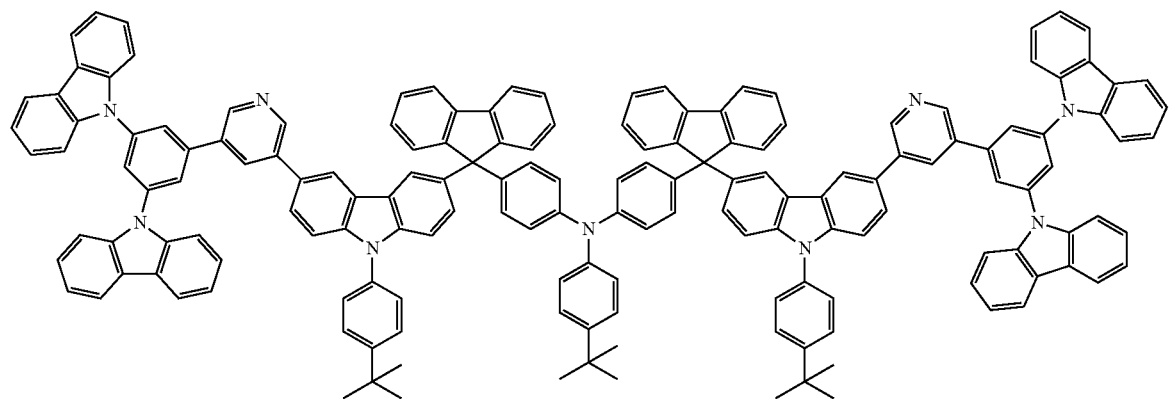

[Chemical Formula 81]
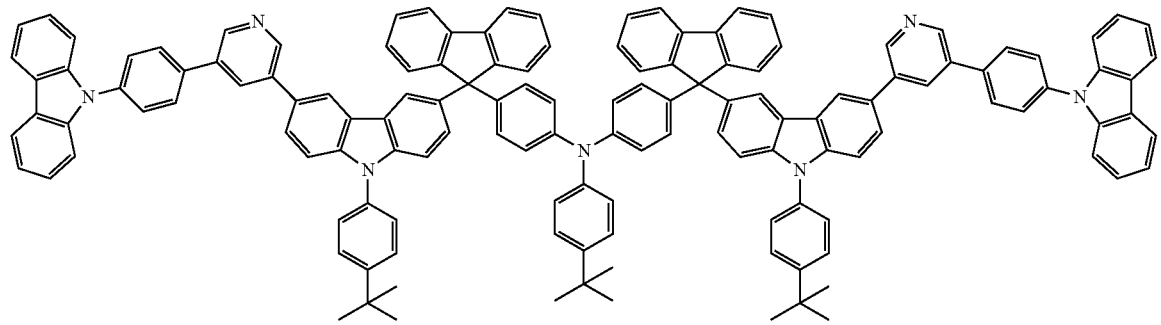
[Chemical Formula 82]
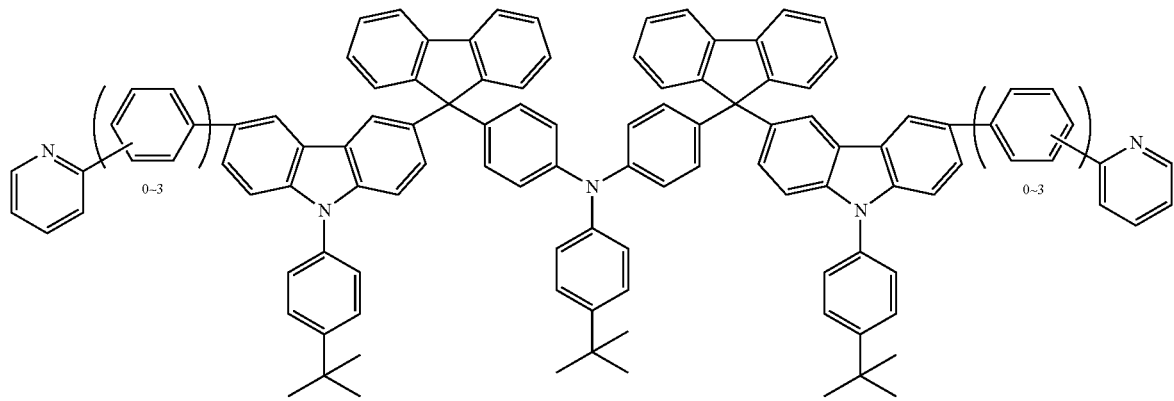
[Chemical Formula 83]
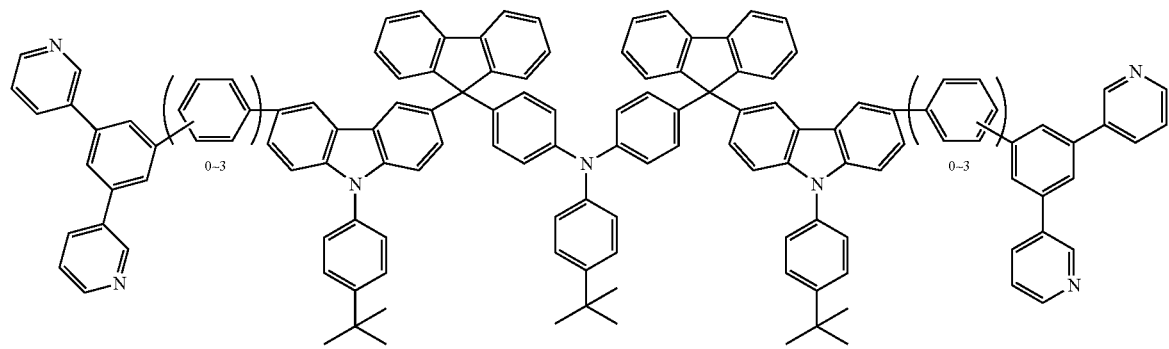
[Chemical Formula 84]
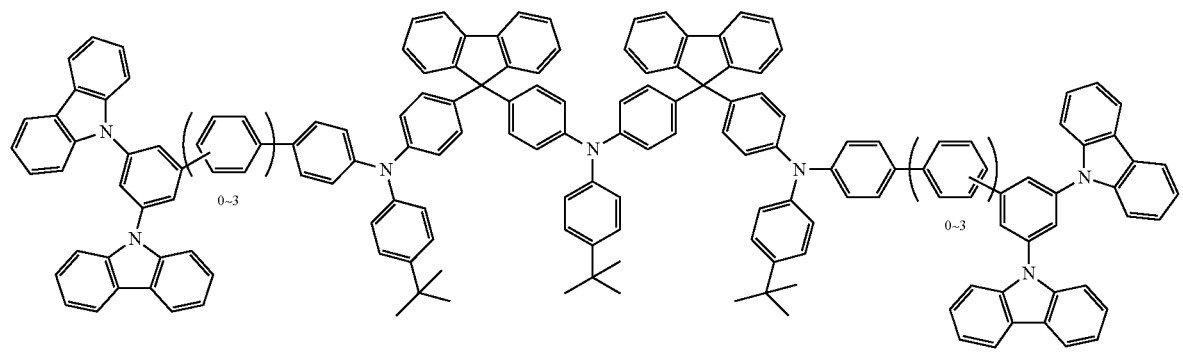

[Chemical Formula 85]
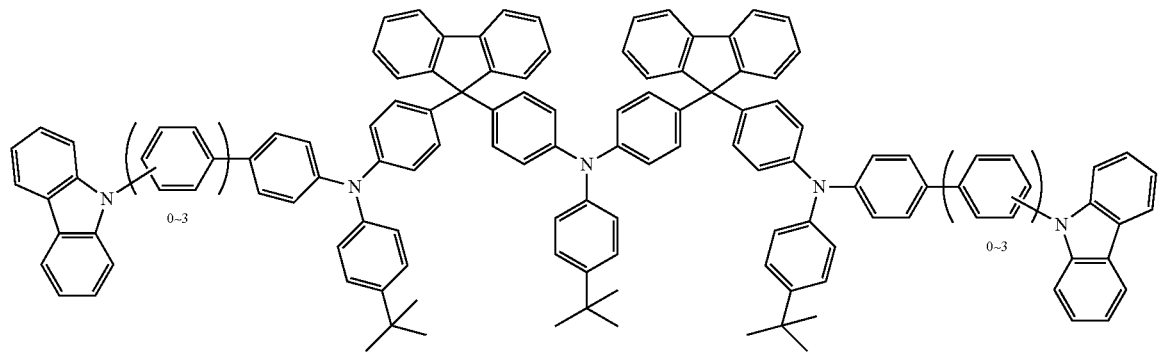
[Chemical Formula 86]
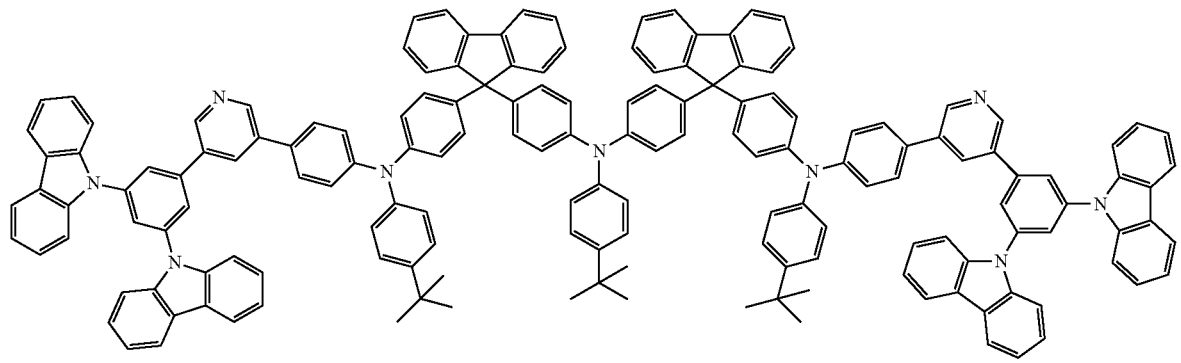
[Chemical Formula 87]
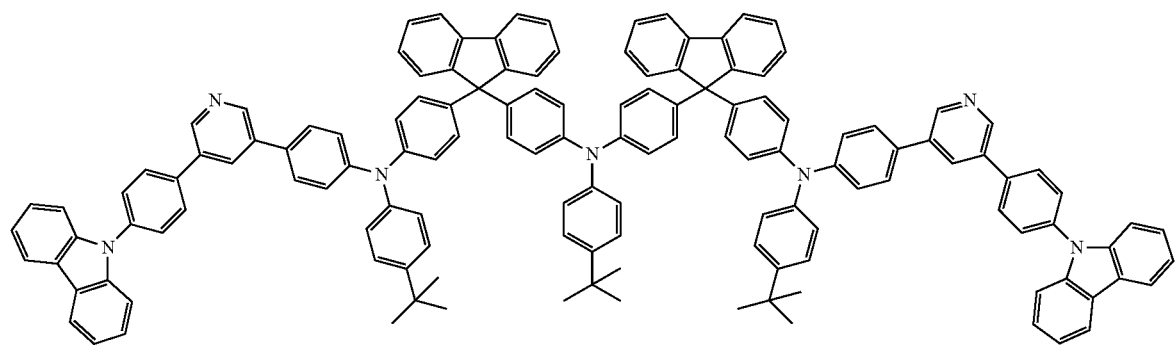
[Chemical Formula 88]
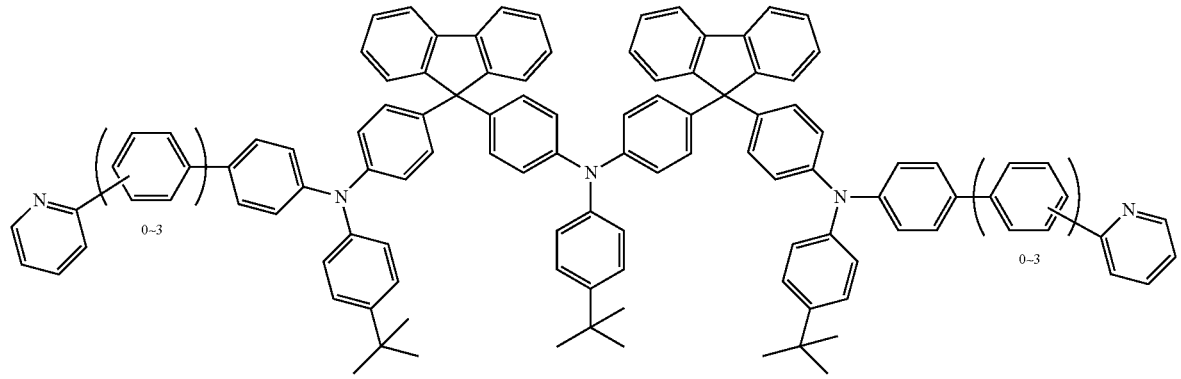

[Chemical Formula 89]
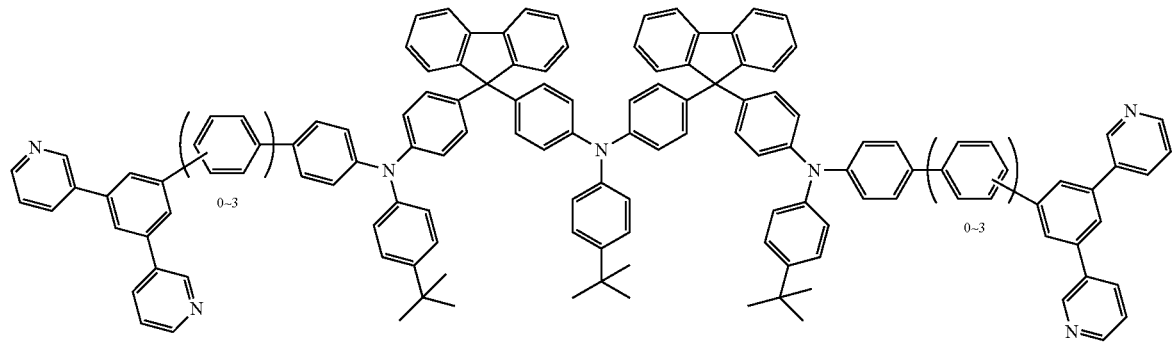
[Chemical Formula 90]
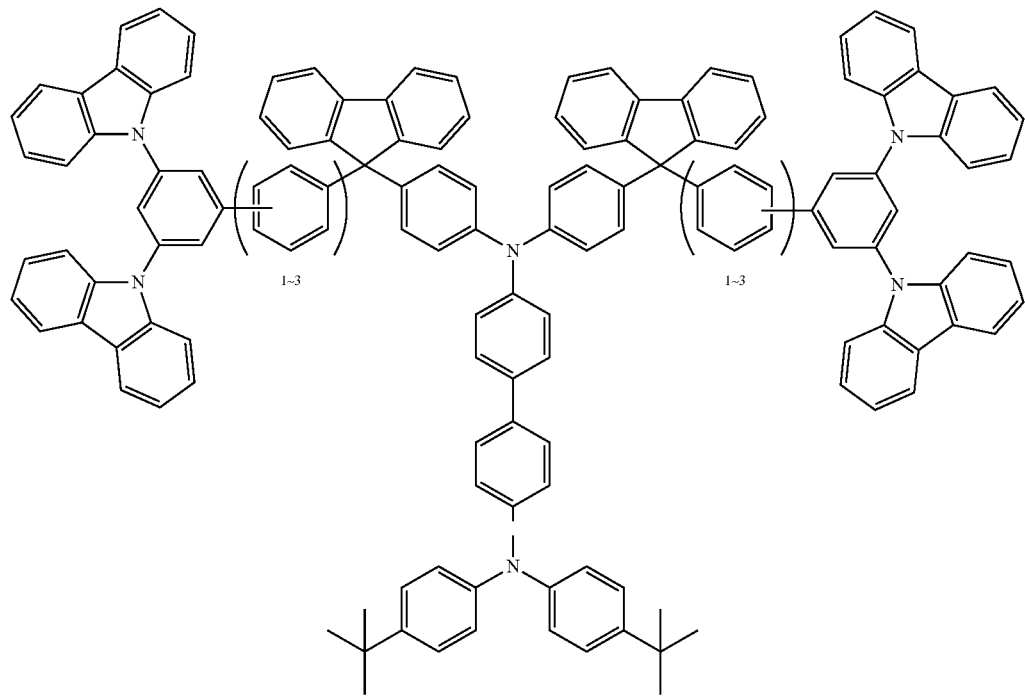

-continued
[Chemical Formula 91]
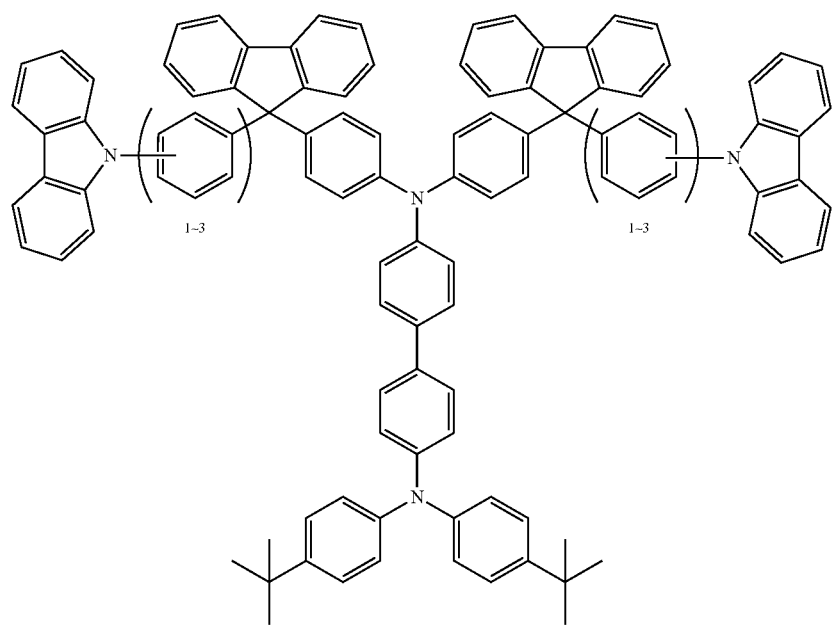
[Chemical Formula 92]
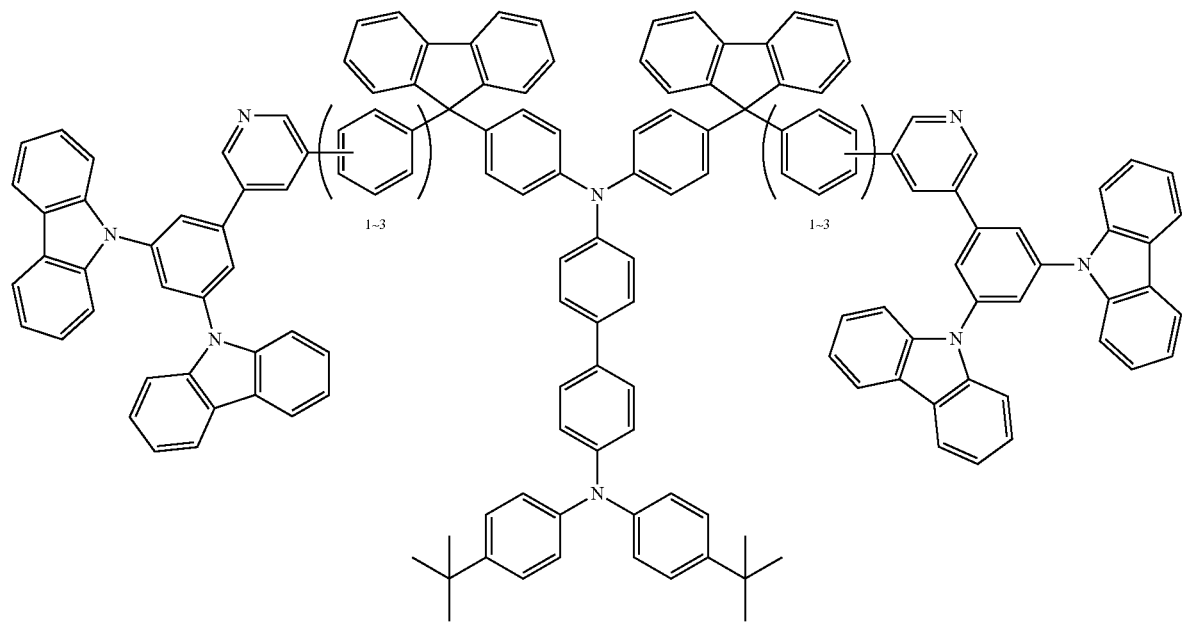

[Chemical Formula 93]
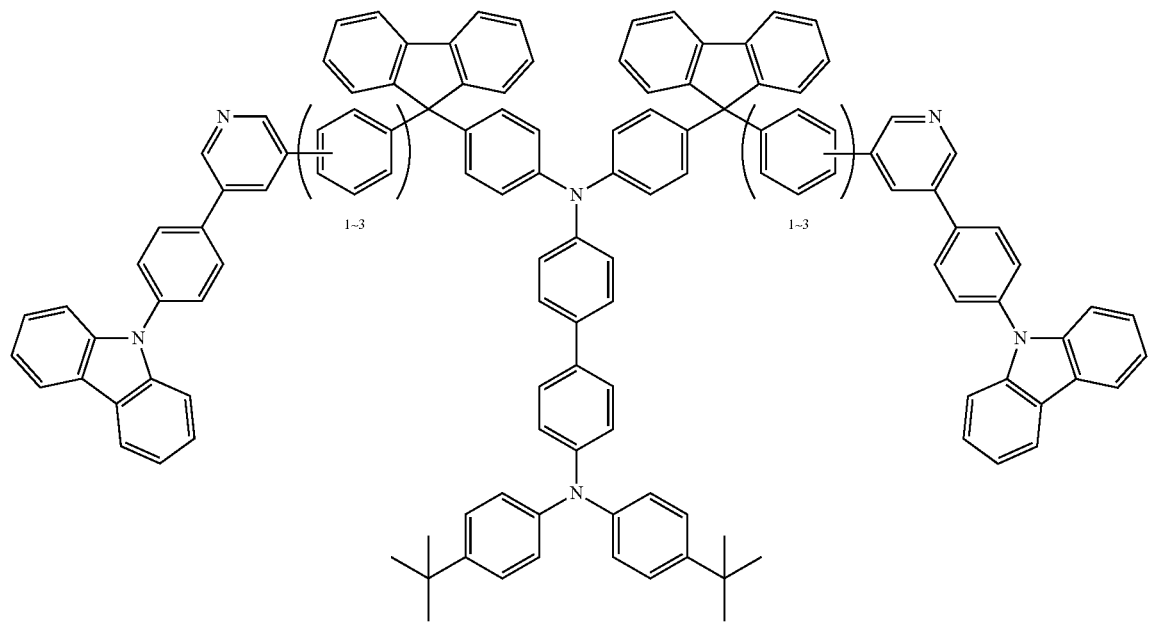
[Chemical Formula 94]
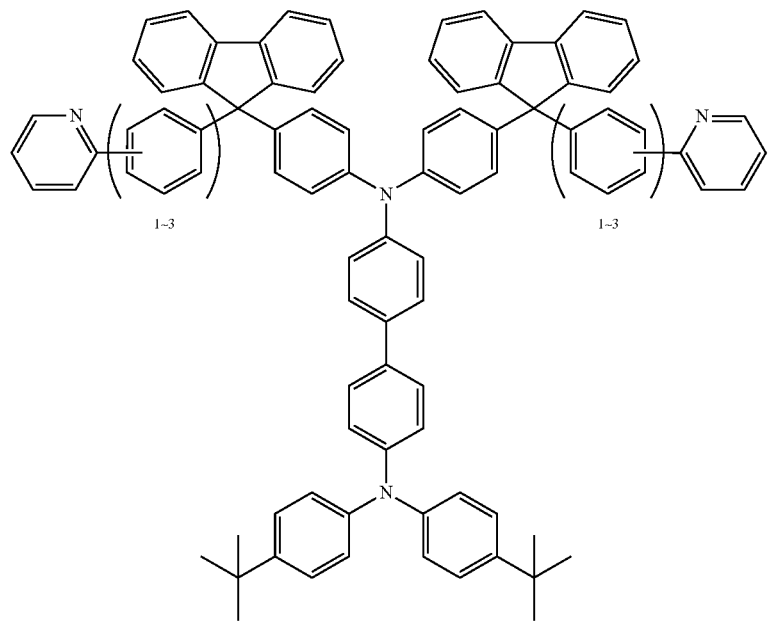

[Chemical Formula 95]
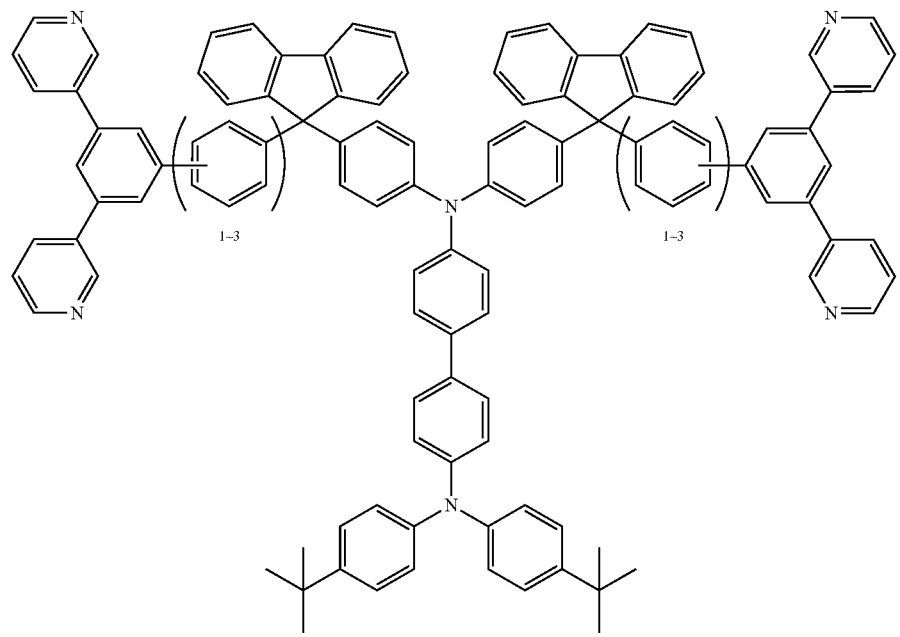
[Chemical Formula 96]
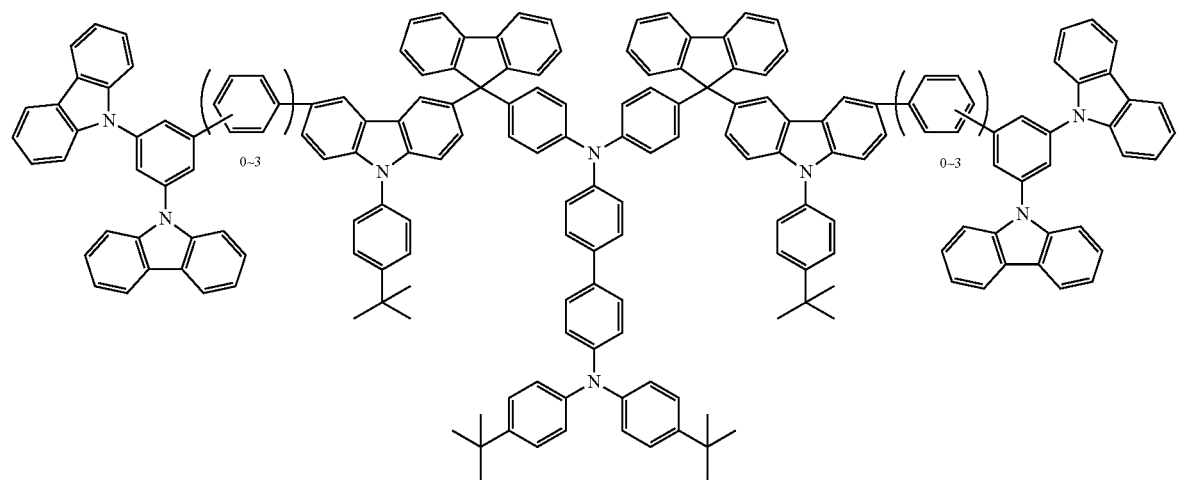

[Chemical Formula 97]
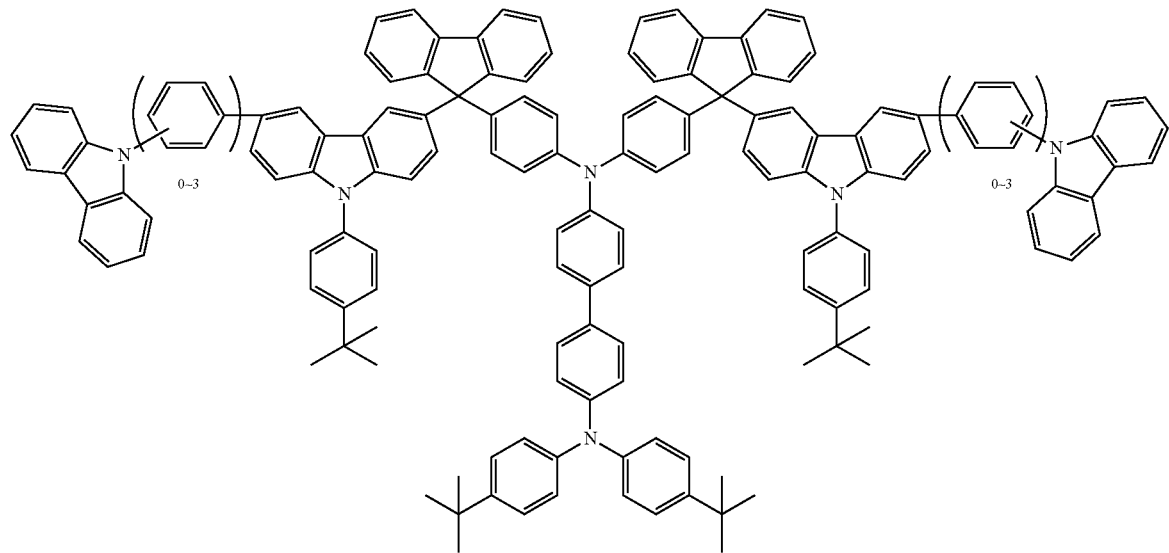
[Chemical Formula 98]
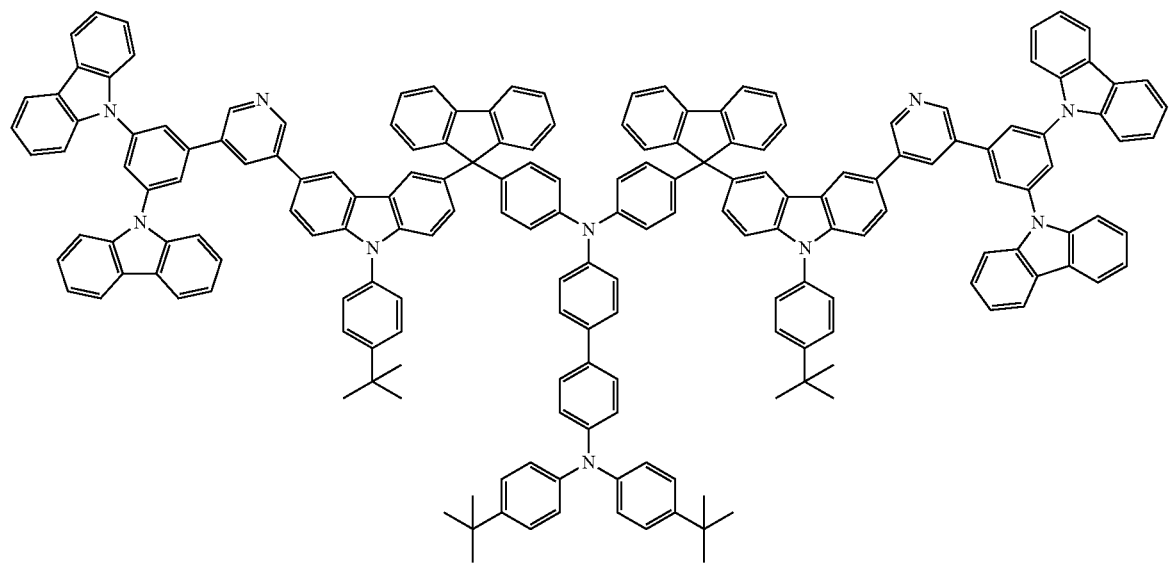
[Chemical Formula 99]
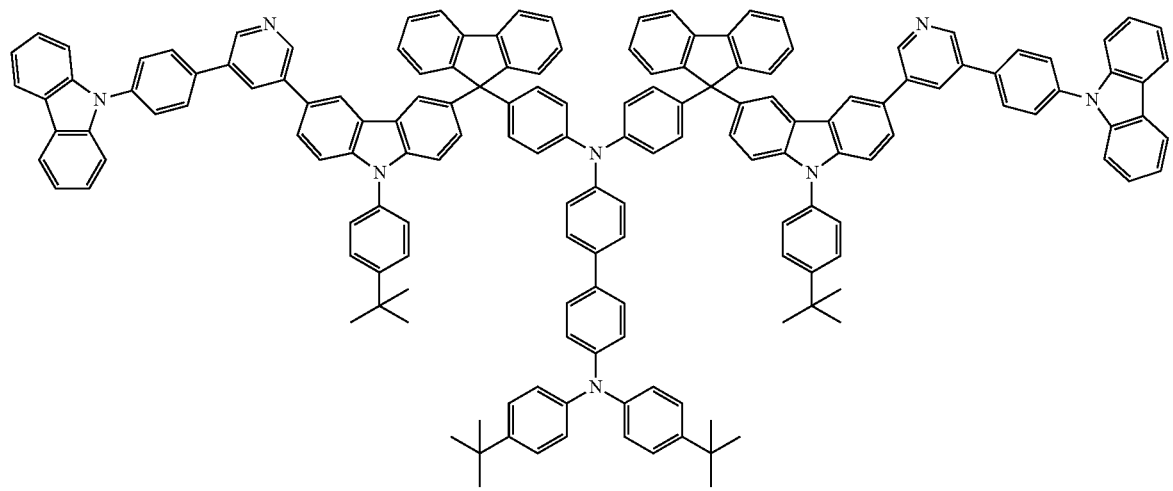

[Chemical Formula 100]
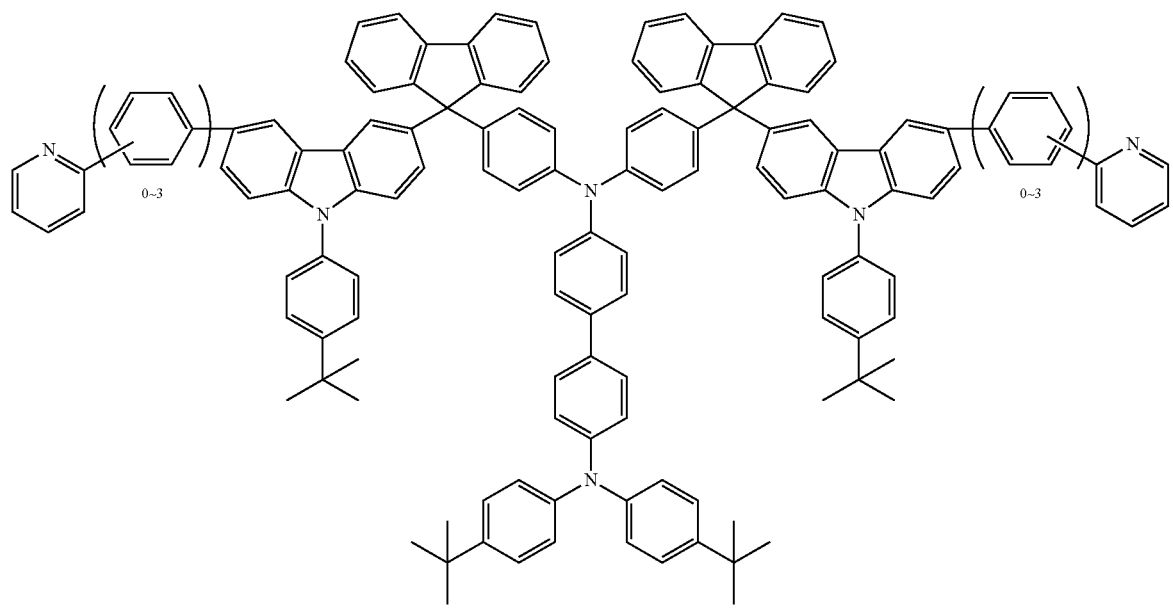
[Chemical Formula 101]
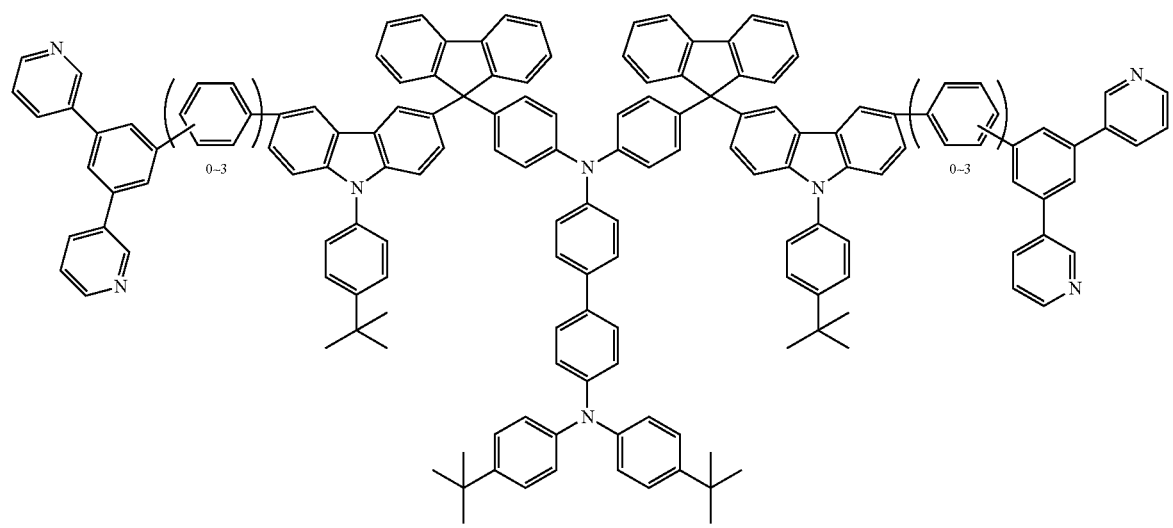
[Chemical Formula 102]
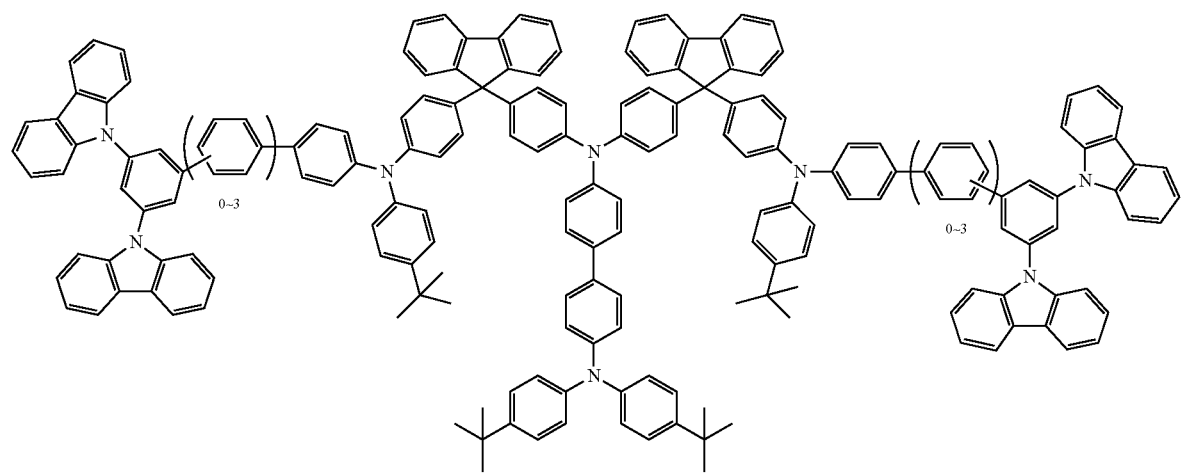

[Chemical Formula 103]
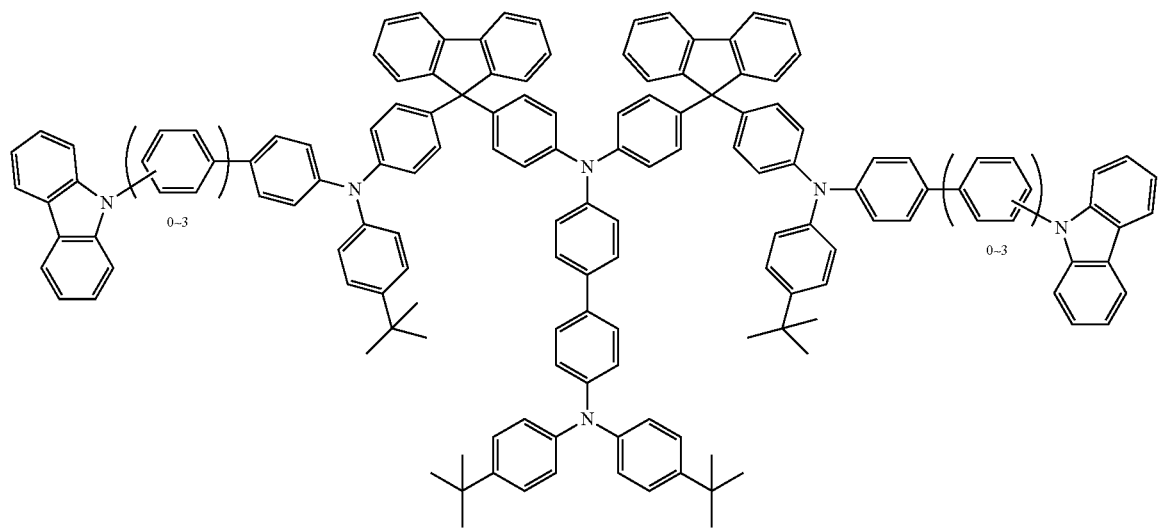
[Chemical Formula 104]
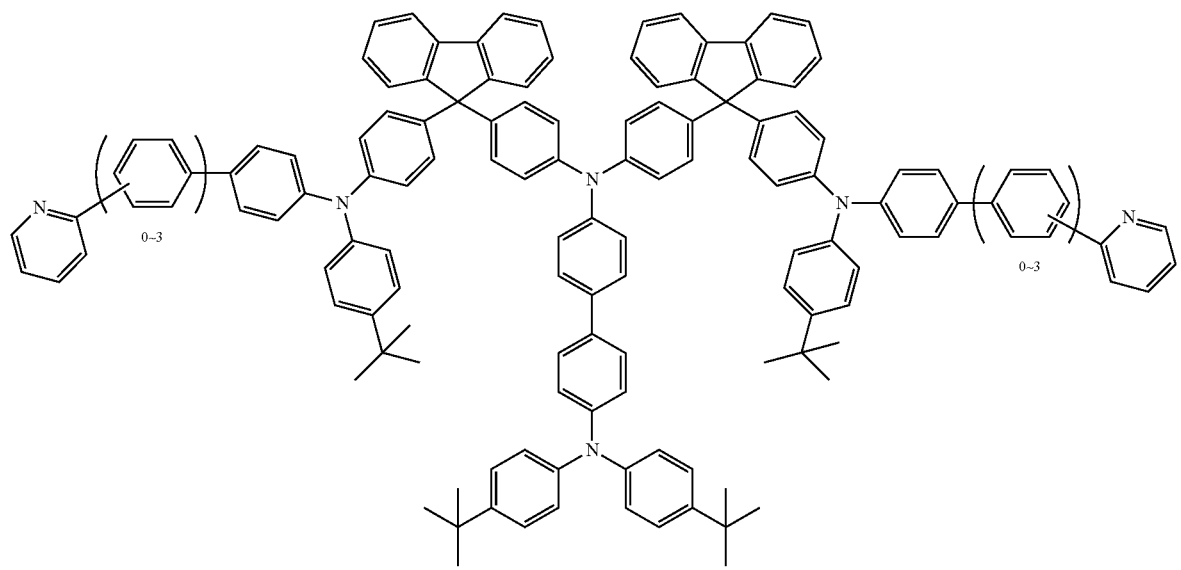
[Chemical Formula 105]
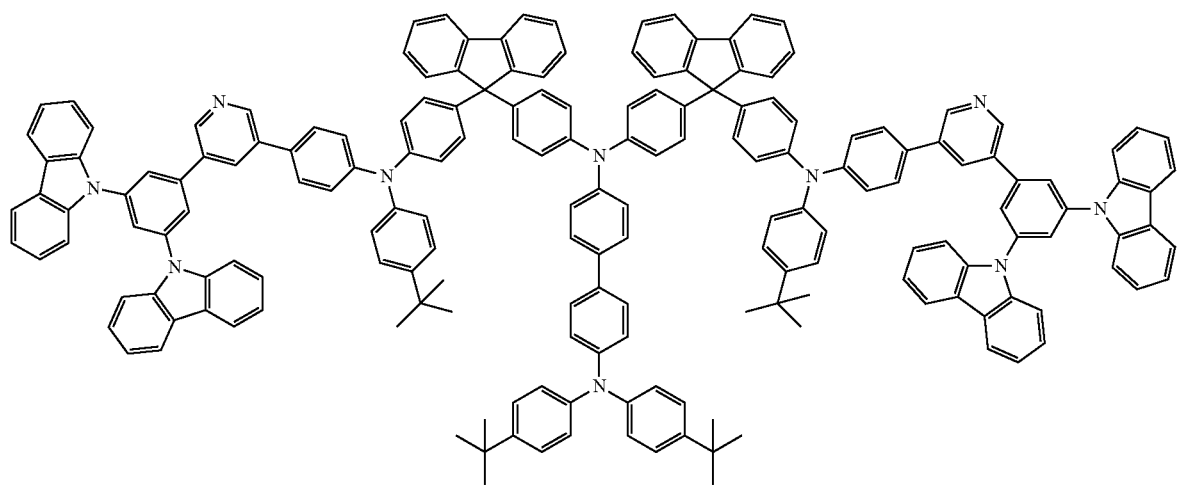

[Chemical Formula 106]
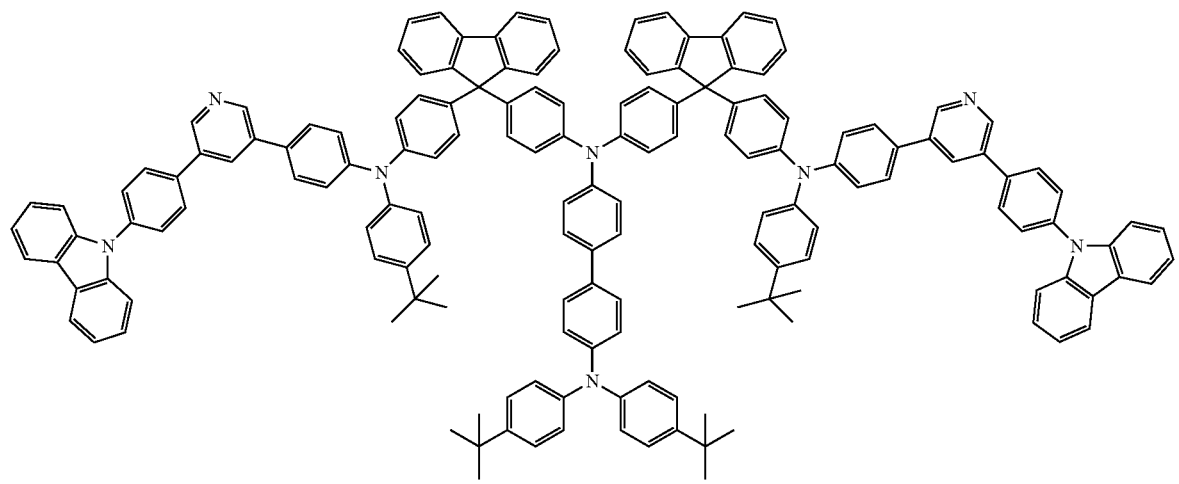
[Chemical Formula 107]
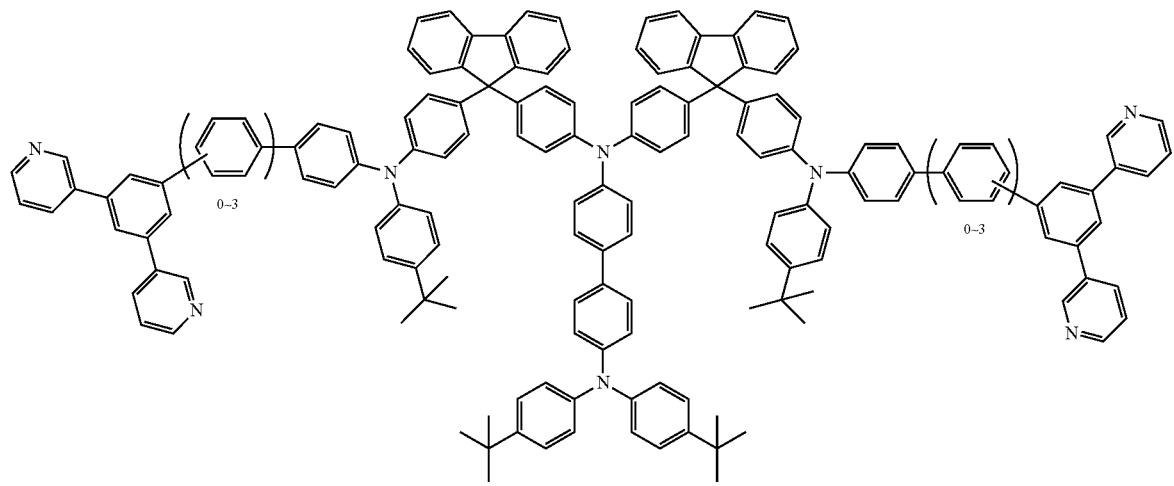
[Chemical Formula 108]
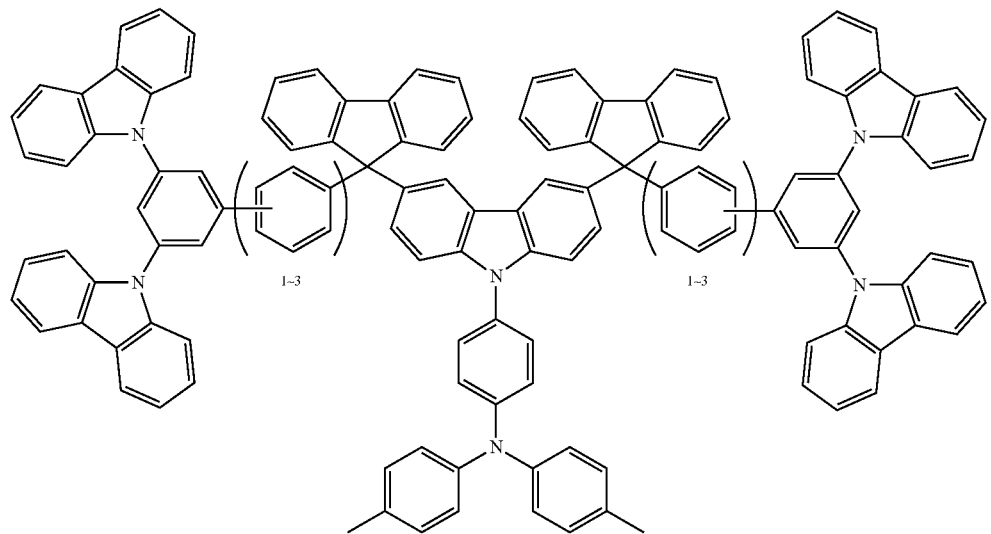

[Chemical Formula 109]
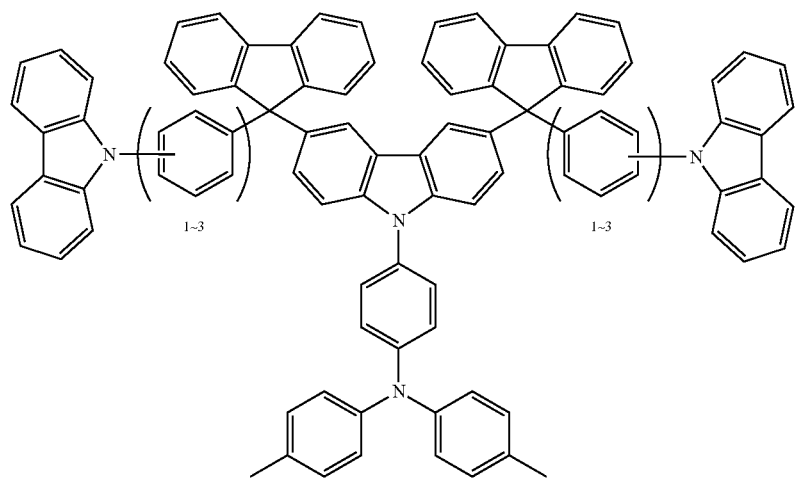
[Chemical Formula 110]
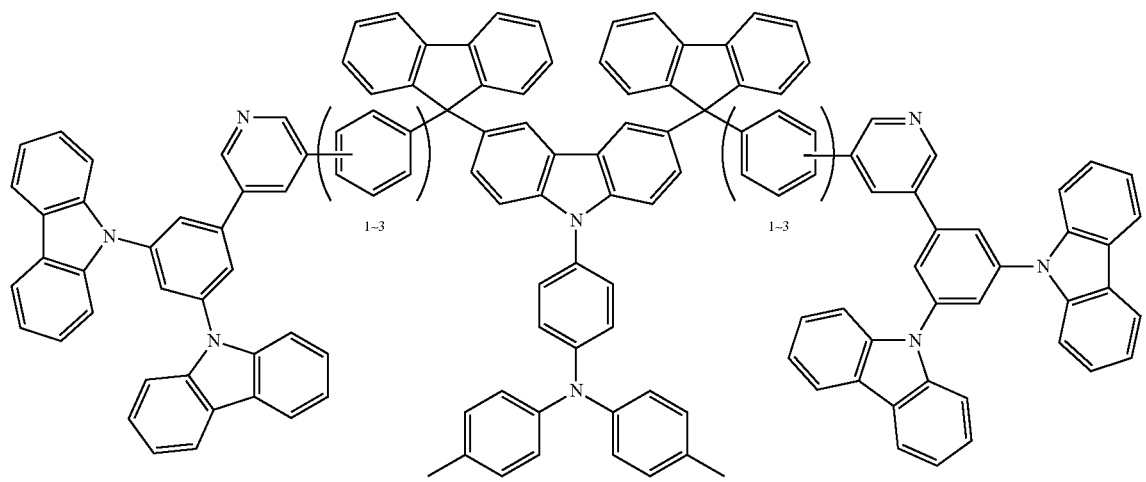
[Chemical Formula 111]
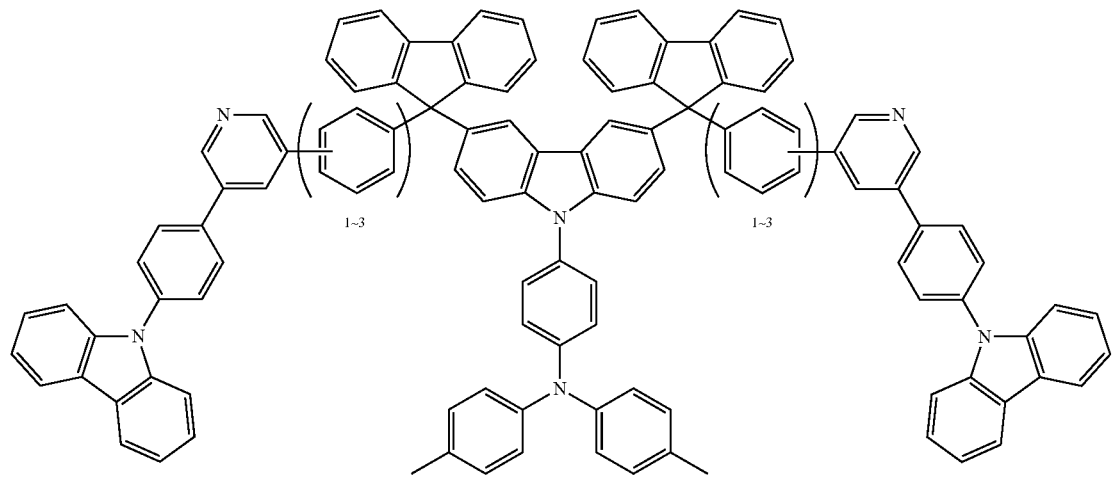

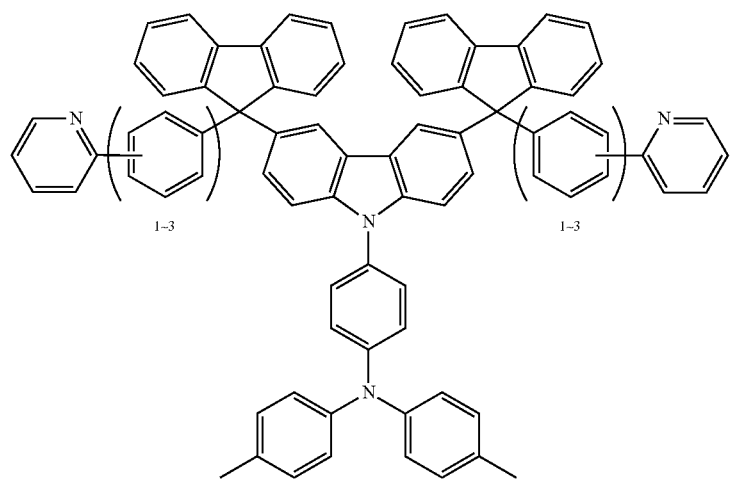
[Chemical Formula 112]
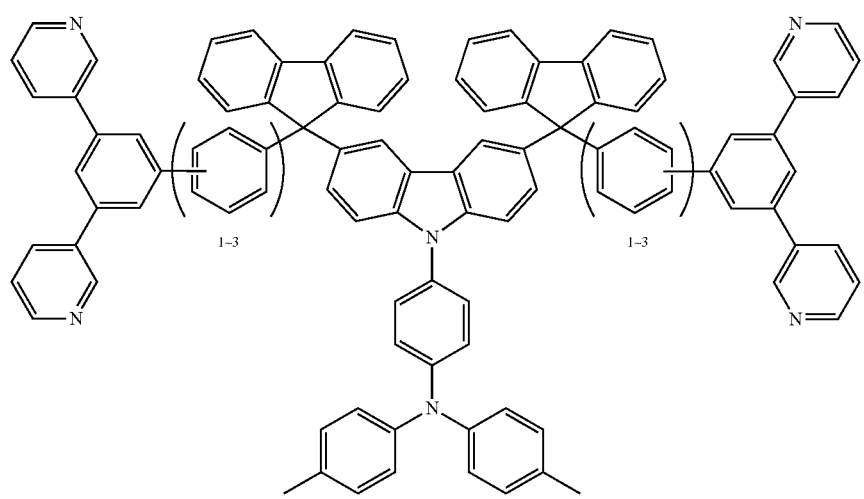
[Chemical Formula 113]
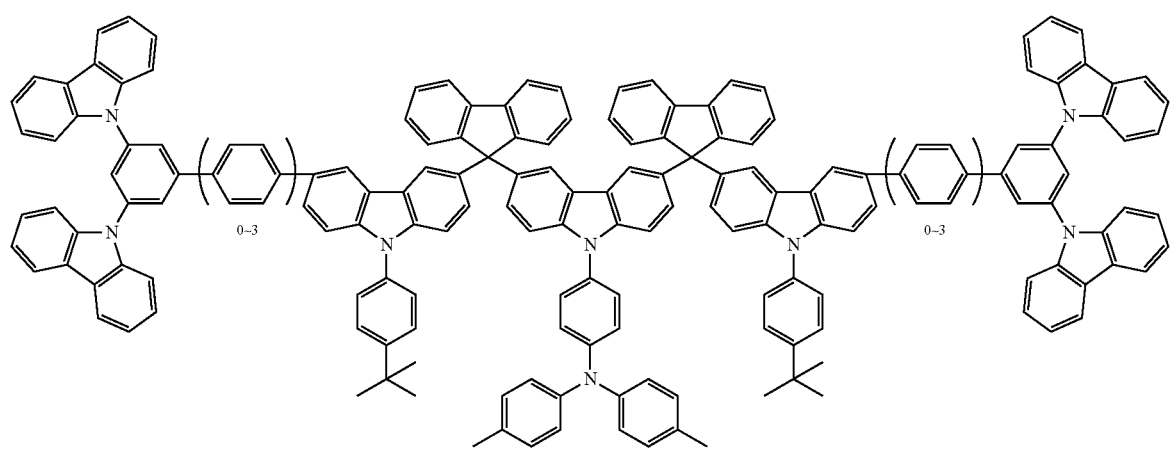
[Chemical Formula 114]

[Chemical Formula 115]
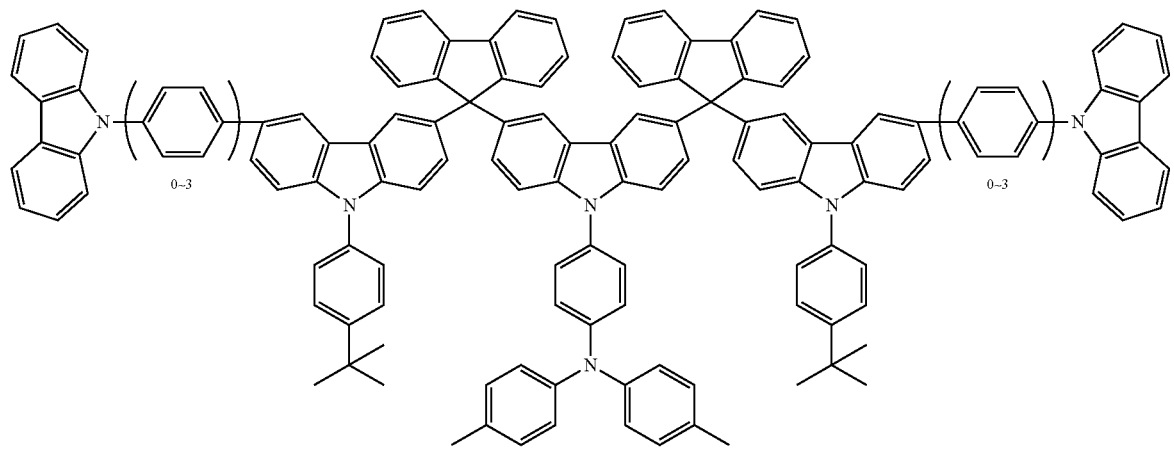
[Chemical Formula 116]
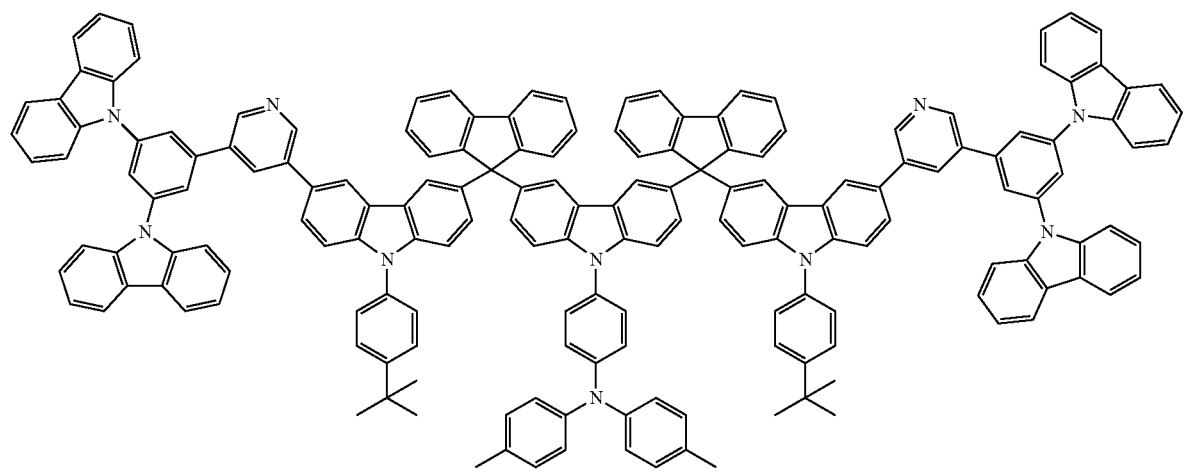
[Chemical Formula 117]
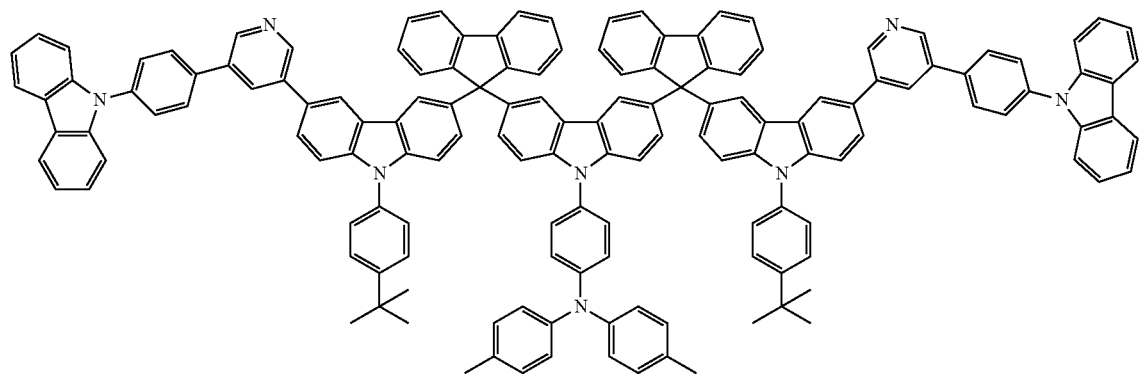

[Chemical Formula 118]
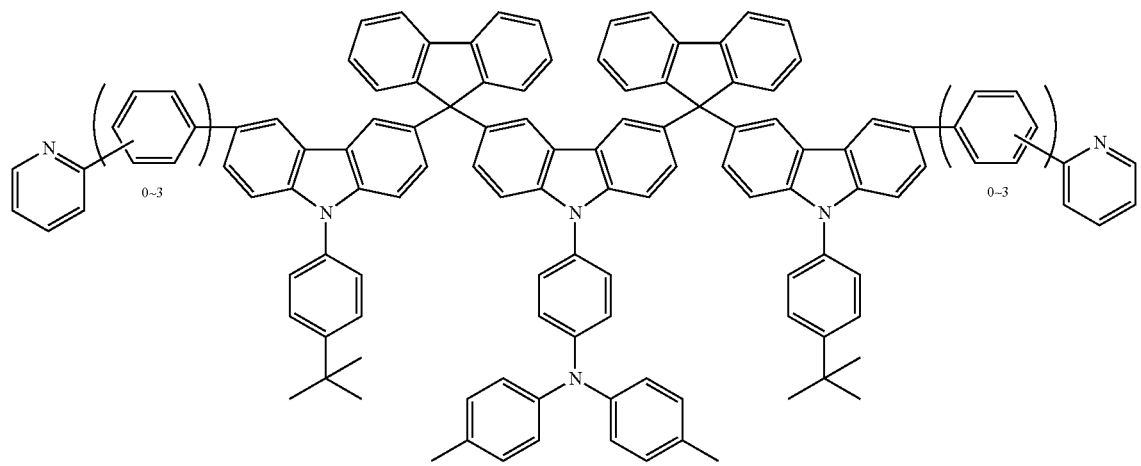
[Chemical Formula 119]
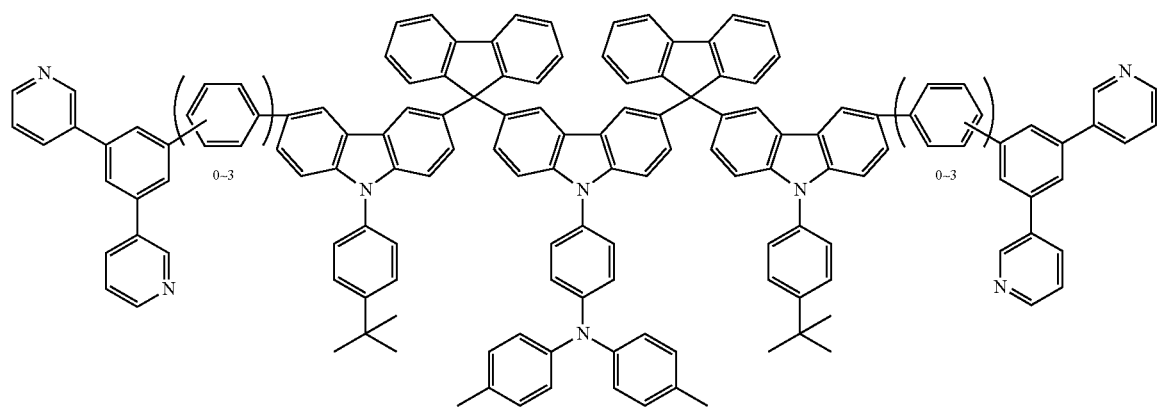
[Chemical Formula 120]
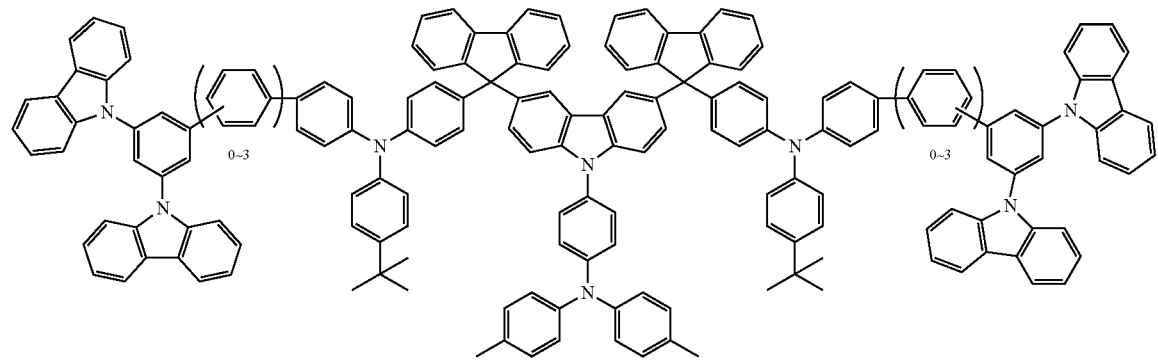

[Chemical Formula 121]
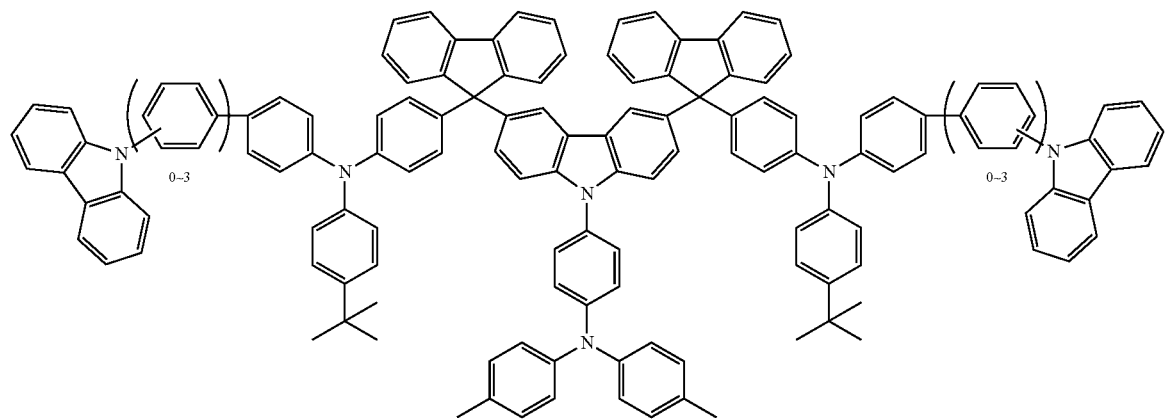
[Chemical Formula 122]
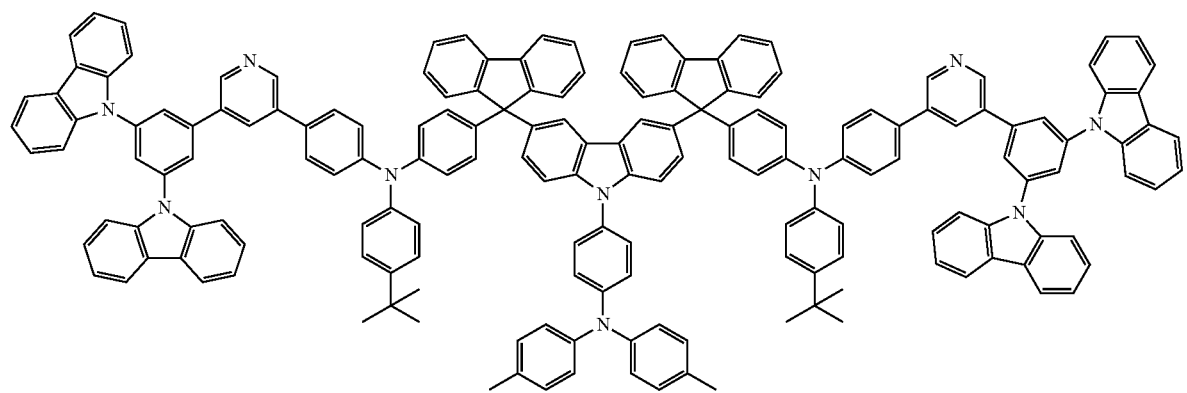
[Chemical Formula 123]
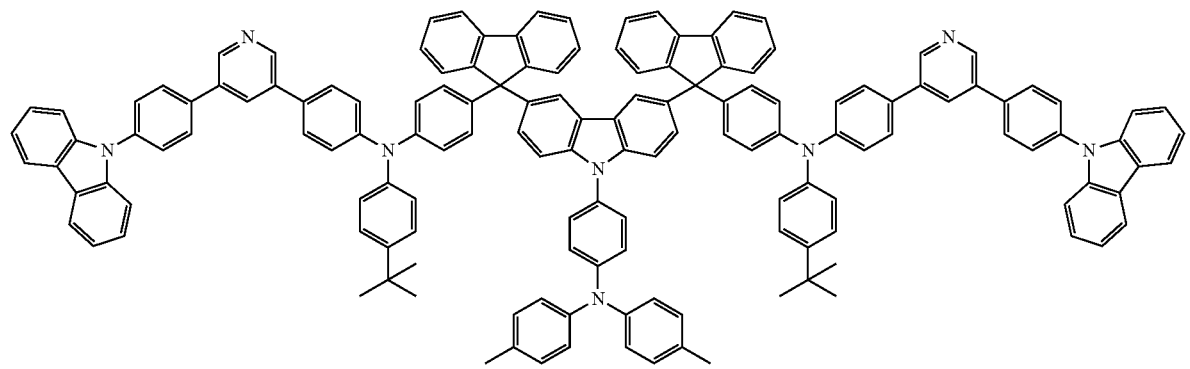

[Chemical Formula 124]
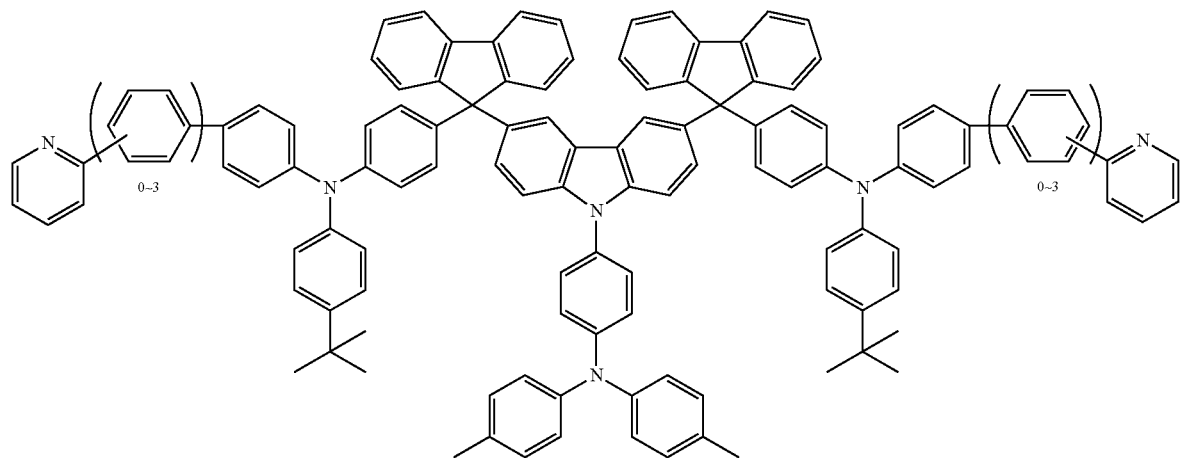
[Chemical Formula 125]
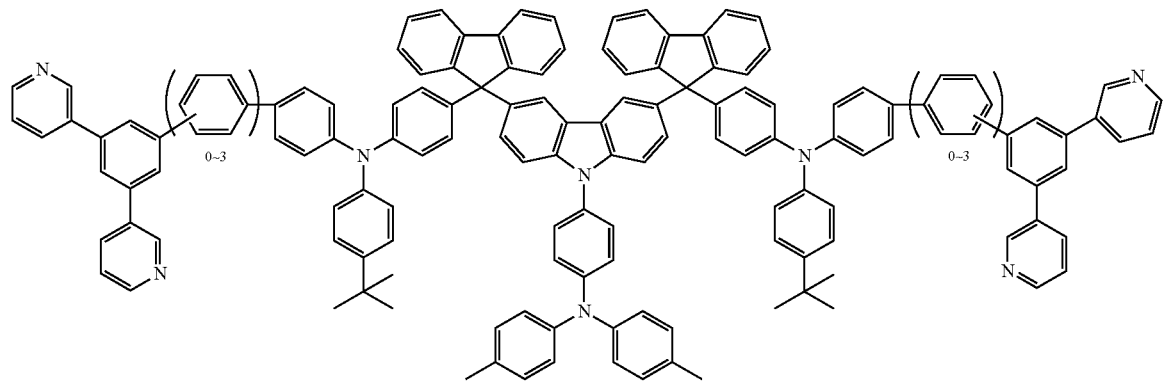
[Chemical Formula 126]
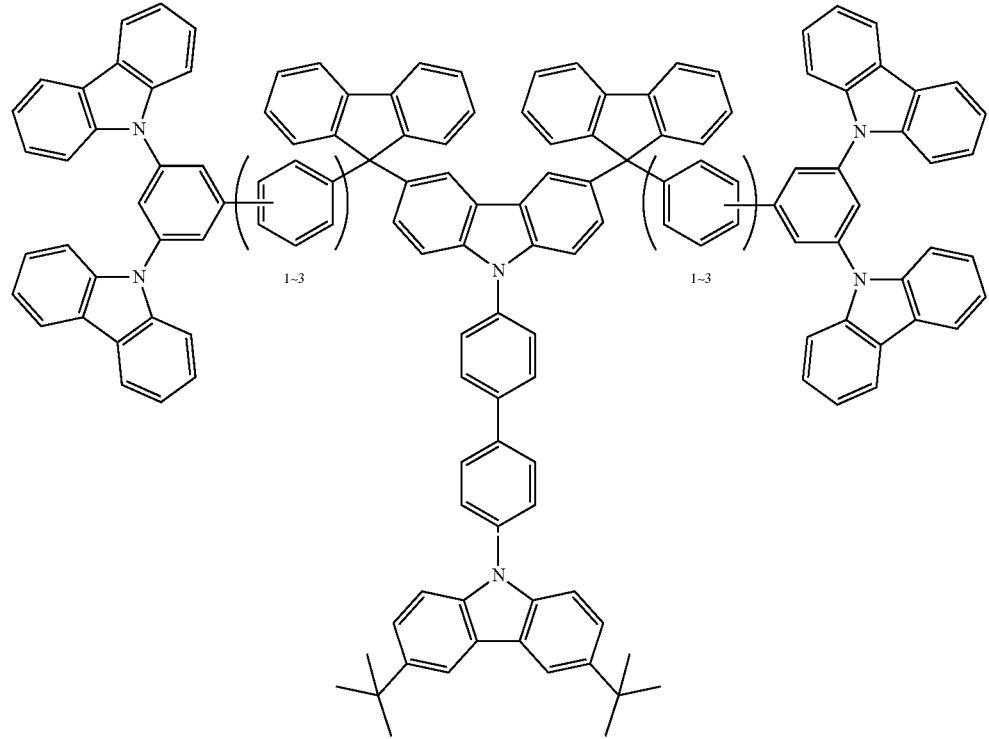

The above Chemical Formulae 38 to 126 are examples of Chemical Formula 1. The compounds where $X_1$ to $X_{16}$ are N in the above Chemical Formula 1 are not exemplified.

The organic compounds may be prepared using a generally-used preparation method of organic compounds without limitation. In one embodiment, the preparation method may be Yamamoto reactions, Suzuki reactions, Stille reactions, Ullman reactions, or so on.

Reaction temperatures, reaction solvents, and reaction times of the preparation method can be adjusted to provide the above organic compounds.

Another embodiment of the present invention provides an organic photoelectric device that includes an organic layer including the above-described organic compounds between a pair of electrodes. In one embodiment, the organic photoelectric device may be an organic light emitting diode.

The organic layer may be an emission layer, a hole injection layer (HIL), a hole transport layer (HTL), an electron transport layer (ETL), an electron injection layer (EIL), an interlayer, and a hole blocking layer. In another embodiment, the emission layer is appropriate for the organic layer.

The organic photoelectric device may further selectively include an interlayer, a hole transport layer (HTL), and an electron transport layer (ETL) as well as a basic device structure of anode/emission layer/cathode.

FIG. 1 is a cross-sectional schematic view of the organic photoelectric device 1 according to one embodiment. FIG. 1 shows an organic photoelectric device including a substrate 11, an anode 12, a hole transport layer (HTL) 13, an emission layer 14, an electron transport layer (ETL) 15, and a cathode 16.

Referring to FIG. 1, the organic photoelectric device may be fabricated using the organic compounds as follows.

First, an anode 12 material is coated on an upper side of the substrate 11.

The substrate 11 is a glass substrate or a transparent plastic substrate having excellent general transparence, face smoothness, handling ease, and water repellency.

The anode 12 material may include transparent and highly conductive indium tin oxide (ITO), tin oxide ($SnO_2$), zinc oxide (ZnO), or so on.

Then, a hole transport layer (HTL) 13 is disposed on the anode 12 using vacuum deposition, sputtering, or spin coating, and an emission layer 14 is disposed on the hole transport layer (HTL) 13 using vacuum deposition, or a solution coating method such as spin coating, Inkjet printing, and so on.

An electron transport layer (ETL) 15 is disposed between the emission layer 14 and a cathode 16.

The emission layer 14 has a thickness ranging from 5 nm to 1 μm, and preferably 10 to 500 nm, and the hole transport layer (HTL) 13 and electron transport layer (ETL) 15 respectively have a thickness ranging from 10 to 10,000 Å.

The electron transport layer (ETL) 15 is formed using vacuum deposition, sputtering, or spin coating of generally-used electron transport layer (ETL) 15 materials.

The hole transport layer (HTL) 13 and electron transport layer (ETL) 15 play roles of efficiently transporting a carrier to the emission layer 14 to heighten light emitting recombination in the emission layer 14.

The hole transport layer (HTL) 13 material includes, but is not limited to, poly(3,4-ethylenedioxy-thiophene) (PEDOT) doped with poly(styrenesulfonic acid) (PSS), and N,N'-bis(3-methylphenyl)-N,N-diphenyl-[1,1¹-biphenyl]-4,4'-diamine (TPD).

The electron transport layer (ETL) 15 material includes, but is not limited to, aluminum trihydroxyquinoline ($Alq_3$), a 1,3,4-oxadiazole derivative such as 2-(4-biphenylyl-5-phenyl-1,3,4-oxadiazole (PBD), a quinoxaline derivative such as 1,3,4-tris[(3-phenyl-6-trifluoromethyl)quinoxalin-2-yl]benzene (TPQ), and a triazole derivative.

The organic compound may be mixed with a phosphorescent light emitting organic compound. The phosphorescent organic compound may be a phosphorescent light emitting organic metal complex from its triplet state, and is preferably a metal complex of at least one group VIII metal ion according to the periodic table of Gregor Johann Mendel. The group VIII metal ion includes a metal ion selected from Fe, Co, Ni, Ru, Rh, Pd, Os, Ir, and Pt, and is preferably Ir or Pt.

Examples of the metal complex may be represented by the following

Chemical Formulae 127 to 129, but are not limited thereto.

[Chemical Formula 127]

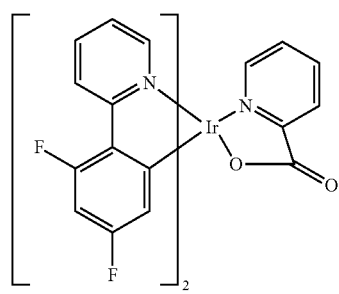

[Chemical Formula 128]

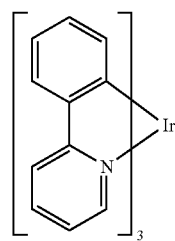

[Chemical Formula 129]

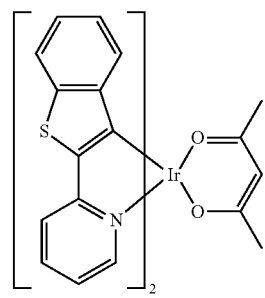

When the organic layer including the organic compound is formed using a solution coating, another low molecular host material can be included along with the organic compound. Examples of the low molecular host material include the compound of the following Chemical Formulae 130 to 133, but are not limited thereto.

[Chemical Formula 130]

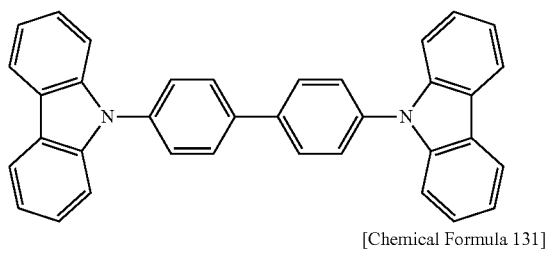

[Chemical Formula 131]

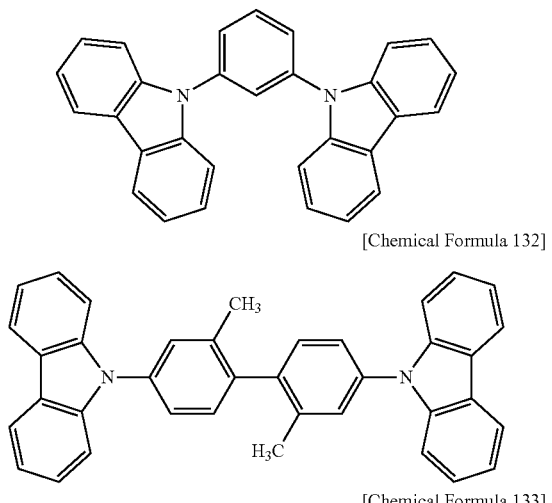

[Chemical Formula 132]

[Chemical Formula 133]

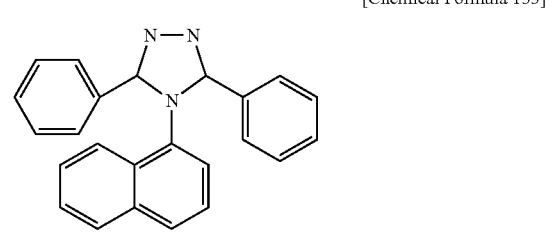

The organic compound may be used by mixing with polymers having conjugated double bonds such as fluorene-based polymers, polyphenylenevinylene-based polymers, and polyparaphenylene-based polymers, and also by mixing with binder resins.

The binder resins may include polyvinylcarbazole (PVK), polycarbonate, polyester, polyarylate, polystyrene, acryl polymers, methacryl polymers, polybutyral, polyvinylacetal, diallylphthalate polymers, phenol resins, epoxy resins, silicone resins, polysulfone resins, or urea resins, and these resins can be used singularly and in combinations.

Selectively, a hole blocking layer may be disposed using vacuum deposition to limit a transport speed of holes into the emission layer 14 and thus to increase recombination opportunity of electrons and holes.

A cathode 16 material is coated on the electron transport layer (ETL) 15.

The cathode material may be lithium (Li), magnesium (Mg), calcium (Ca), aluminum (Al), Al:Li, Ba:Li, or Ca:Li having a small work function.

Hereinafter, the embodiments are illustrated in more detail with reference to examples. However, the following are exemplary embodiments and are not limiting.

A person having ordinary skills in this art can sufficiently understand parts of the present invention that are not specifically described.

EXAMPLE 1

Synthesis of M-1

[Reaction Scheme 1]

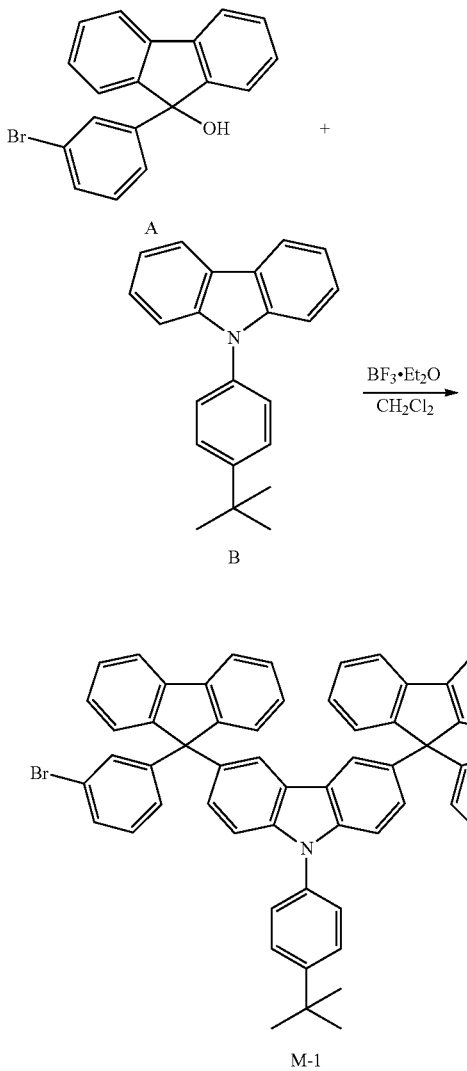

6.0 g (17.79 mmol) of 9-(3-bromophenyl)-9-H-fluorene-9-ol (A) and 2.13 g (7.11 mmol) of 9-(4-tert-butylphenyl)9-H-carbazole (B) were dissolved in 40 mL of dichloromethane under a nitrogen atmosphere, and 3 mL of a boron trifluoride diethylether complex ($BF_3.OEt_2$) was slowly added thereto in a dropwise fashion. The mixture was agitated at room temperature for 12 hours, and 50 mL of water was added thereto, completing the reaction. The reactant was extracted with dichloromethane and washed four times. The extraction solution was dried with anhydrous magnesium sulfate. Then, the solvent in the dried solution was removed under reduced pressure. The resulting product was purified through silica gel column using a solvent of methylenechloride/hexane mixed in a ratio of 1:3, obtaining 5 g (56.2%) of white M-1.

EXAMPLE 2

Synthesis of M-2

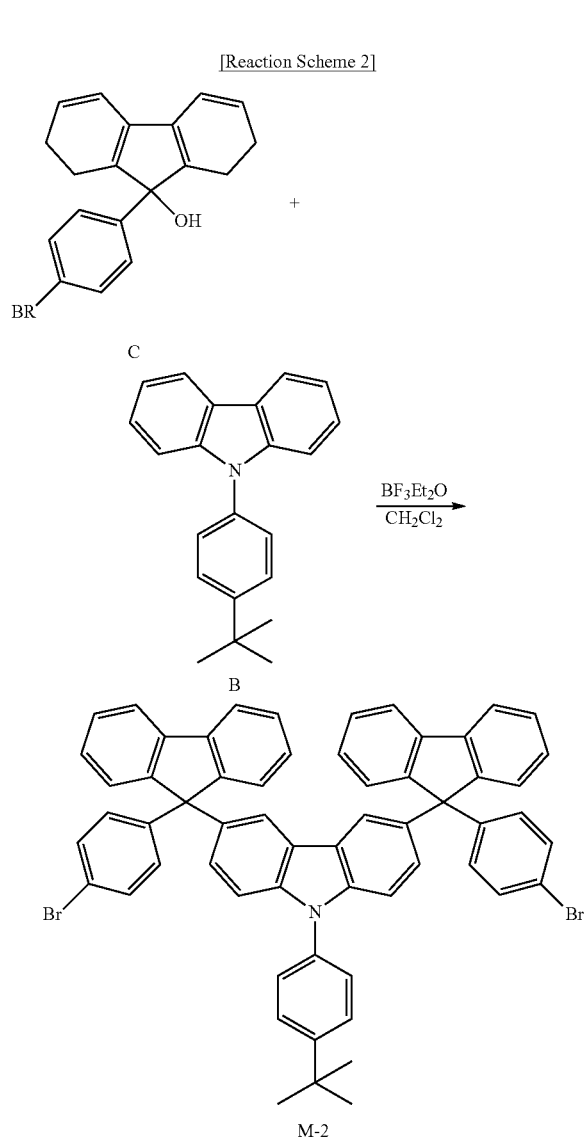

EXAMPLE 3

Synthesis of M-3

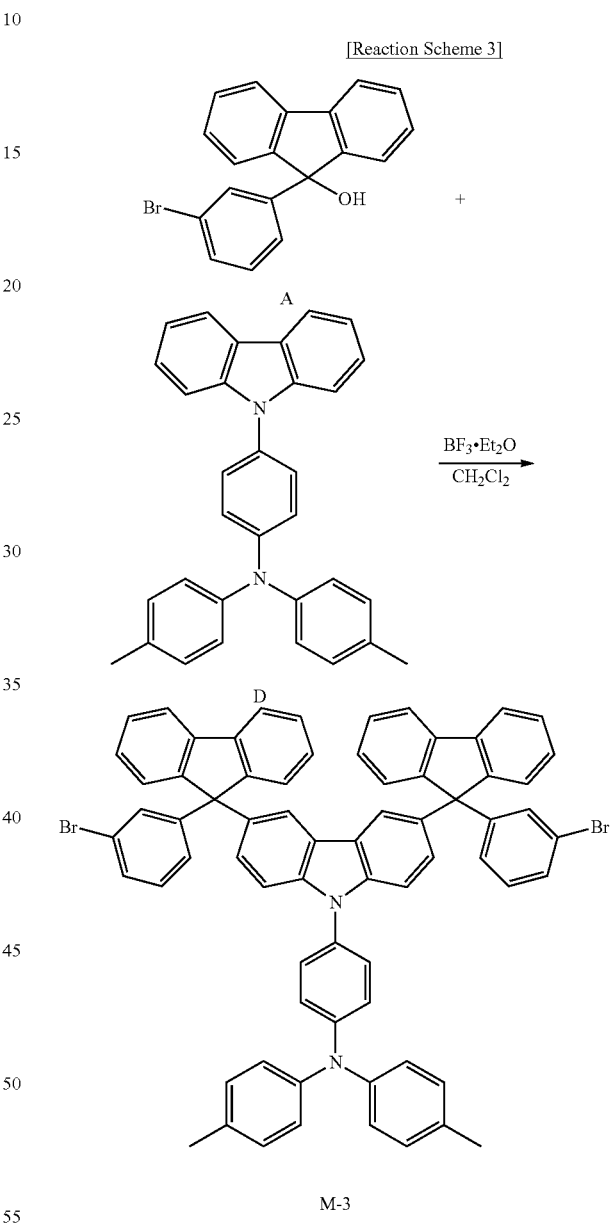

6.0 g (17.79 mmol) of 9-(4-bromophenyl)-9-H-fluorene-9-ol (C) and 2.13 g (7.11 mmol) of (9-(4-tert-butylphenyl)-9-H-carbazole) (B) were dissolved in 40 mL of dichloromethane under a nitrogen atmosphere, and 3 mL of a boron trifluoride diethylether complex ($BF_3 \cdot OEt_2$) was slowly added thereto in a dropwise fashion. The mixture was agitated at room temperature for 12 hours, and 50 mL of water was added thereto, completing the reaction. The reactant was extracted with dichloromethane and washed four times. The extraction solution was dried with anhydrous magnesium sulfate. Then, the solvent was removed from the dried solution under reduced pressure. The resulting product was purified through a silica gel column using a solvent of methylenechloride/hexane mixed in a ratio of 2:3, obtaining 5.0 g (75%) of white M-2.

3.0 g (8.89 mmol) of 9-(3-bromophenyl)-9-H-fluorene-9-ol (A) and 1.77 g (4.04 mmol) of a material D were dissolved in 50 mL of dichloromethane under a nitrogen atmosphere, and 1.5 mL of a boron trifluoride diethylether complex ($BF_3 \cdot OEt_2$) was slowly added thereto in a dropwise fashion. The mixture was agitated at room temperature for 12 hours, and 50 mL of water was added thereto, completing the reaction. The reactant was extracted and washed four times with dichloromethane. The extraction solution was dried with anhydrous magnesium sulfate. Then, the solvent was removed from the dried solution under reduced pressure. The resulting product was purified through a silica gel column using a solvent of methylenechloride/hexane mixed in a ratio of 1:2, obtaining 3.3 g (75.8%) of white M-3.

EXAMPLE 4

Synthesis of M-4

[Reaction Scheme 4]

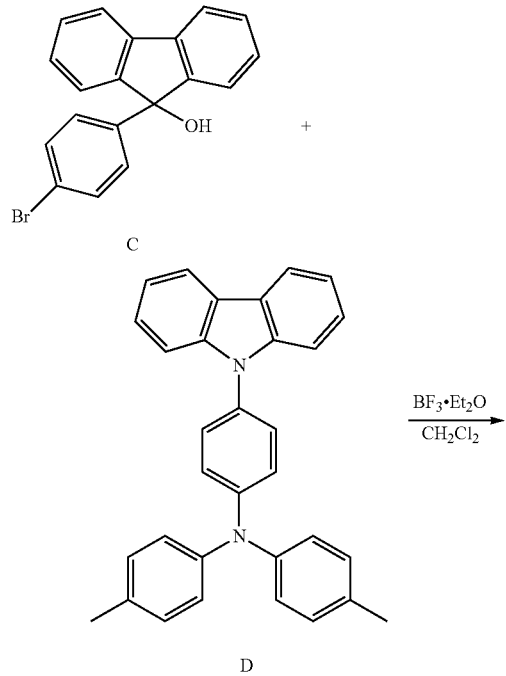

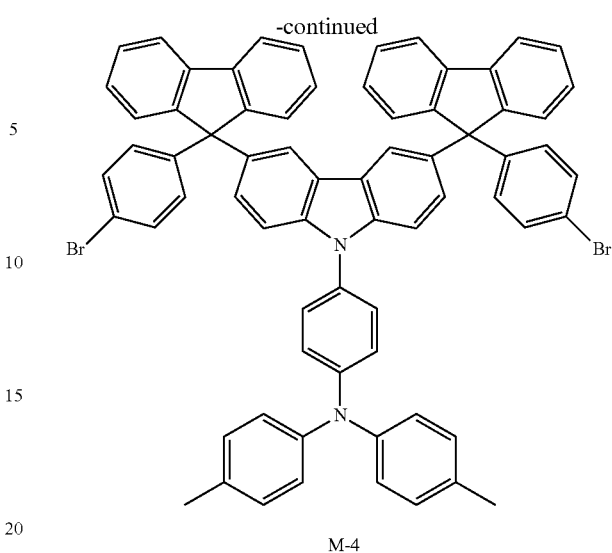

3.0 g (8.89 mmol) of 9-(4-bromophenyl)-9-H-fluorene-9-ol and 1.77 g (4.04 mmol) of a material D were dissolved in 50 mL of dichloromethane under a nitrogen atmosphere, and 1.5 mL of a boron trifluoride diethylether complex ($BF_3 \cdot OEt_2$) was slowly added thereto in a dropwise fashion. The mixture was agitated at room temperature for 12 hours, and 50 mL of water was added thereto, completing the reaction. The reactant was extracted with dichloromethane and washed four times with water. The extraction solution was dried with anhydrous magnesium sulfate. The solution was removed from the resulting solution under reduced pressure. The resulting product was purified through a silica gel column using a solvent of methylenechloride/hexane mixed in a ratio of 1:2, obtaining 3.0 g (69%) of white M-4.

EXAMPLE 5

Synthesis of M-5

[Reaction Scheme 5]

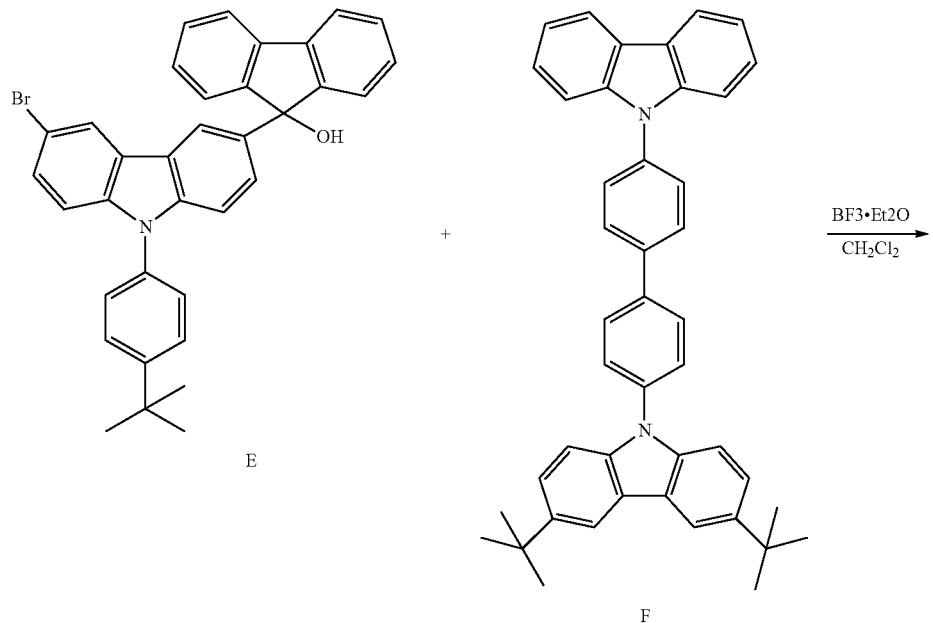

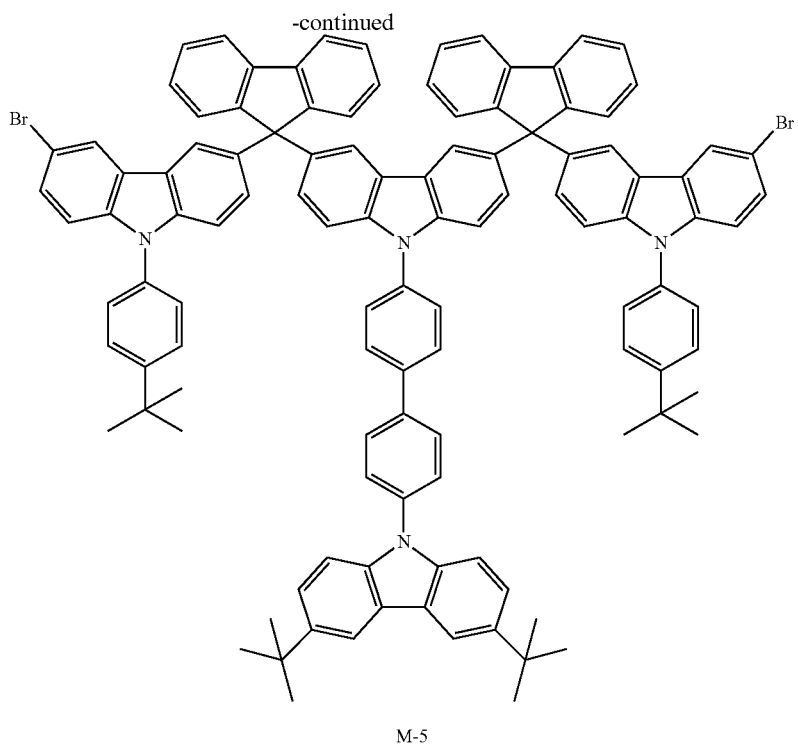

M-5

4.11 g (7.37 mmol) of a material E and 2.0 g (3.35 mmol) of a material F were dissolved in 40 mL of dichloromethane under a nitrogen atmosphere, and 1.5 mL of a trifluoride diethylether complex ($BF_3.OEt_2$) was slowly added thereto in a dropwise fashion. The mixture was agitated at room temperature for 12 hours, and 50 mL of water was added thereto, completing the reaction. The reactant was extracted with dichloromethane and washed four times with water. The extraction solution was dried with anhydrous magnesium sulfate. Then, the solvent was removed from the dried solution under reduced pressure. The resulting product was purified through a silica gel column using a solvent of methylenechloride/hexane mixed in a ratio of 1:2, obtaining 4.1 g (73%) of white M-5.

EXAMPLE 6

Synthesis of CISH-1

[Reaction Scheme 6]

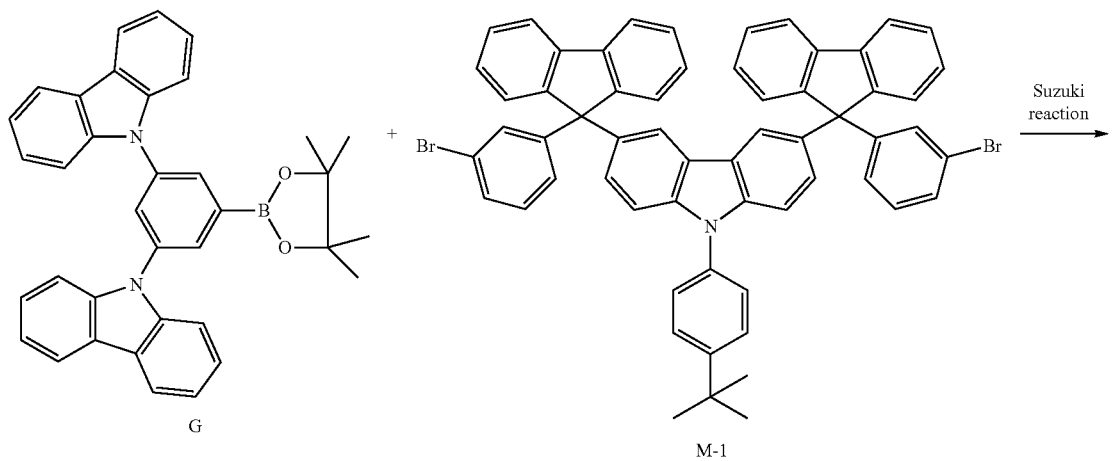

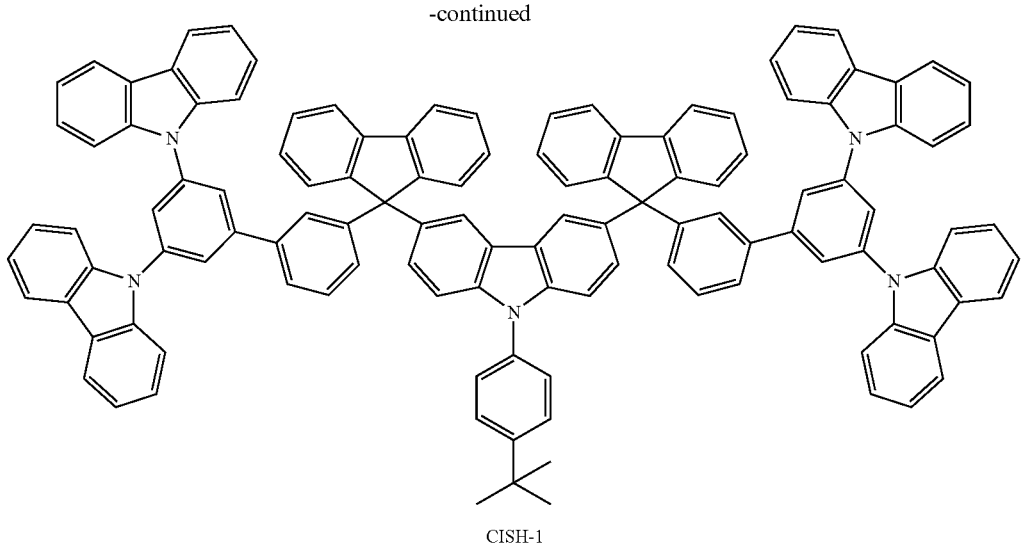

CISH-1

1.2 g (1.27 mmol) of M-1, 1.71 g (3.19 mmol) of a material G (3-(9H-carbazol-9-yl)-5-(4,4,5,5-tetramethyl-1,3,2-dioxaborolan-2-yl)phenyl)-9H-carbazole), and 0.06 g (0.05 mmol) of tetrakistriphenylphosphine palladium were dissolved in 30 mL of THF (tetrahydrofuran) in a 250 ml round flask with a thermometer, a reflux condenser, and an agitator, and 15 mL of 20% tetratriethylammonium hydroxide was added thereto. The resulting mixture was refluxed for reaction at 75° C. for 48 hours.

When the reaction was complete, the reactant was cooled to room temperature and then extracted several times with methylenechloride and washed several times with water.

Then, the reactant was treated with anhydrous magnesium sulfate to remove moisture. After the resulting product was filtered, the solvent was removed.

The reactant without the solvent was purified through a silica gel column using a solvent of methylenechloride/hexane mixed in a ratio of 2:3 and recrystallized in a mixed solvent of methylenechloride/hexane, obtaining 1.49 g (73.3%) of white CISH-1. This material had a maximum light emitting wavelength of 365 nm in a chloroform solution.

EXAMPLE 7

Synthesis of CISH-2

[Reaction Scheme 7]

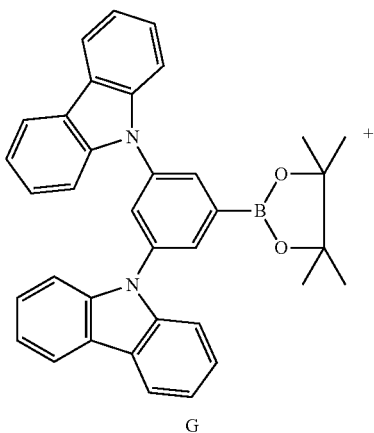

G

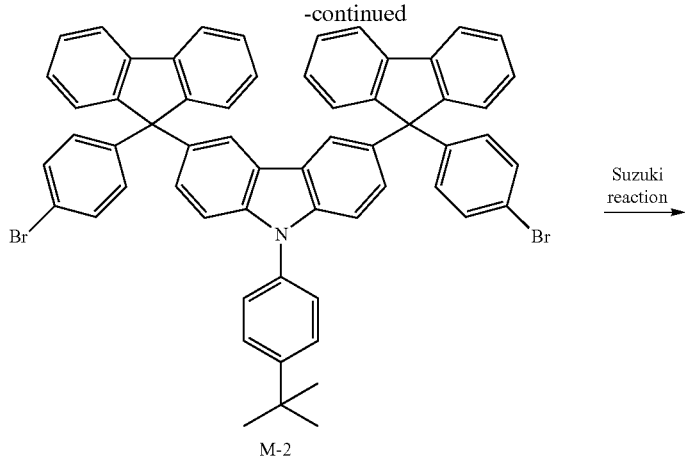

M-2

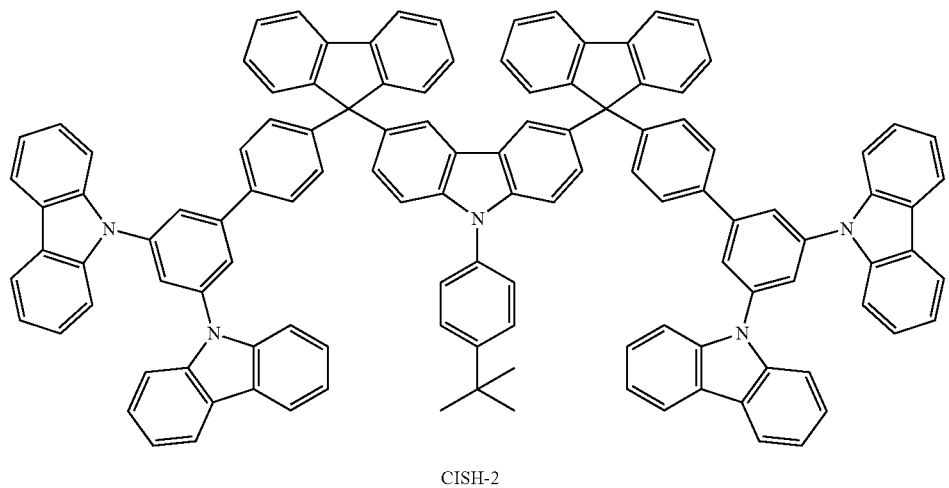

CISH-2

1.2 g (1.27 mmol) of M-2, 1.71 g (3.19 mmol) of a material G (3-(9H-carbazol-9-yl)-5-(4,4,5,5-tetramethyl-1,3,2-dioxaborolan-2-yl)phenyl)-9H-carbazole, and 0.06 g (0.05 mmol) of tetrakistriphenylphosphinepalladium were dissolved in 30 mL of THF (tetrahydrofuran) in a 250 ml round flask with a thermometer, a reflux condenser, and an agitator under an argon atmosphere, and 15 mL of 20% tetratriethylammonium hydroxide was added thereto. The resulting mixture was refluxed for reaction at 75° C. for 48 hours.

When the reaction was complete, the reactant was cooled to room temperature and extracted several times with methylenechloride, and was also washed several times with water.

Then, the washed reactant was treated with anhydrous magnesium sulfate to remove moisture. After the resulting product was filtered, the solvent was removed therefrom.

The reactant with no solvent was purified through a silica gel column using a solvent of methylenechloride/hexane mixed in a ratio of 2:3 and recrystallized in a mixed solvent of methylenechloride/hexane, obtaining 1.6 g (78.8%) of white CISH-2. This material had a maximum light emitting wavelength of 363 nm in a chloroform solution.

EXAMPLE 8

Synthesis of CISH-3

[Reaction Scheme 8]

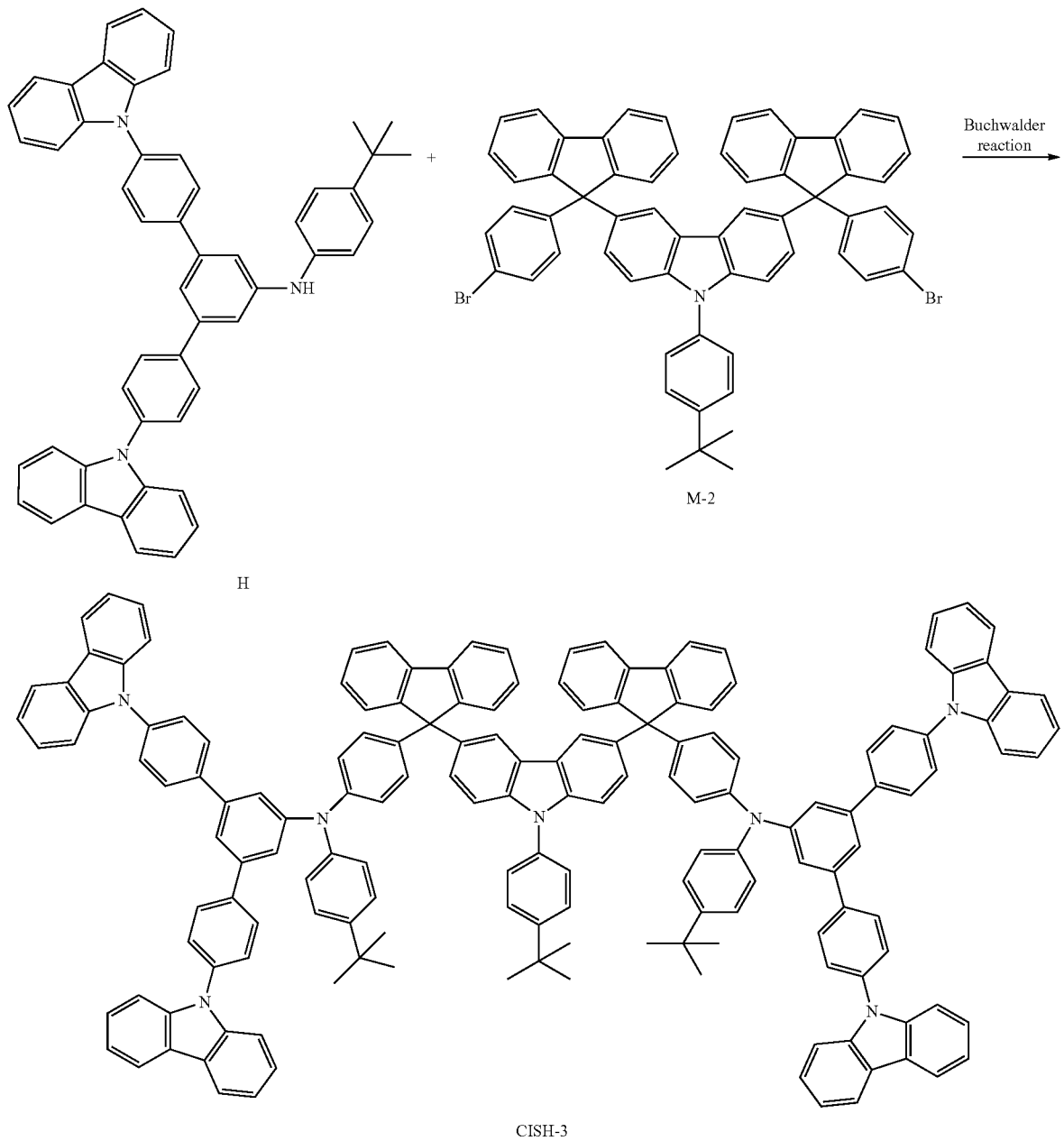

1.2 g (1.27 mmol) of M-2, 2.71 g (3.83 mmol) of a material H, 0.37 g (3.81 mmol) of sodium tert-butoxide, 23 mg (0.025 mmol) of Pd(dba)$_2$, and 7.7 mg (0.038 mmol) of P(t-Bu)$_3$ were dissolved in 60 mL of anhydrous toluene in a 250 ml round flask with a thermometer, a reflux condenser, and an agitator under an argon atmosphere. The mixture was refluxed for reaction at 75° C. for 48 hours.

When the reaction was complete, the reactant was cooled to room temperature and extracted several times extracted with toluene, and was also washed several times with water. Then, the reactant was treated with anhydrous magnesium sulfate to remove moisture. After the reactant was filtered, the solvent was removed therefrom.

The resulting reactant with no solvent was purified through a silica gel column using a solvent of methylenechloride/hexane mixed in a ratio of 1:2 and recrystallized in a mixed solvent of methylenechloride/acetone, obtaining 1.3 g (47.1%) of white CISH-3. This material had a maximum light emitting wavelength of 443 nm in a chloroform solution.

EXAMPLE 9

Synthesis of CISH-4

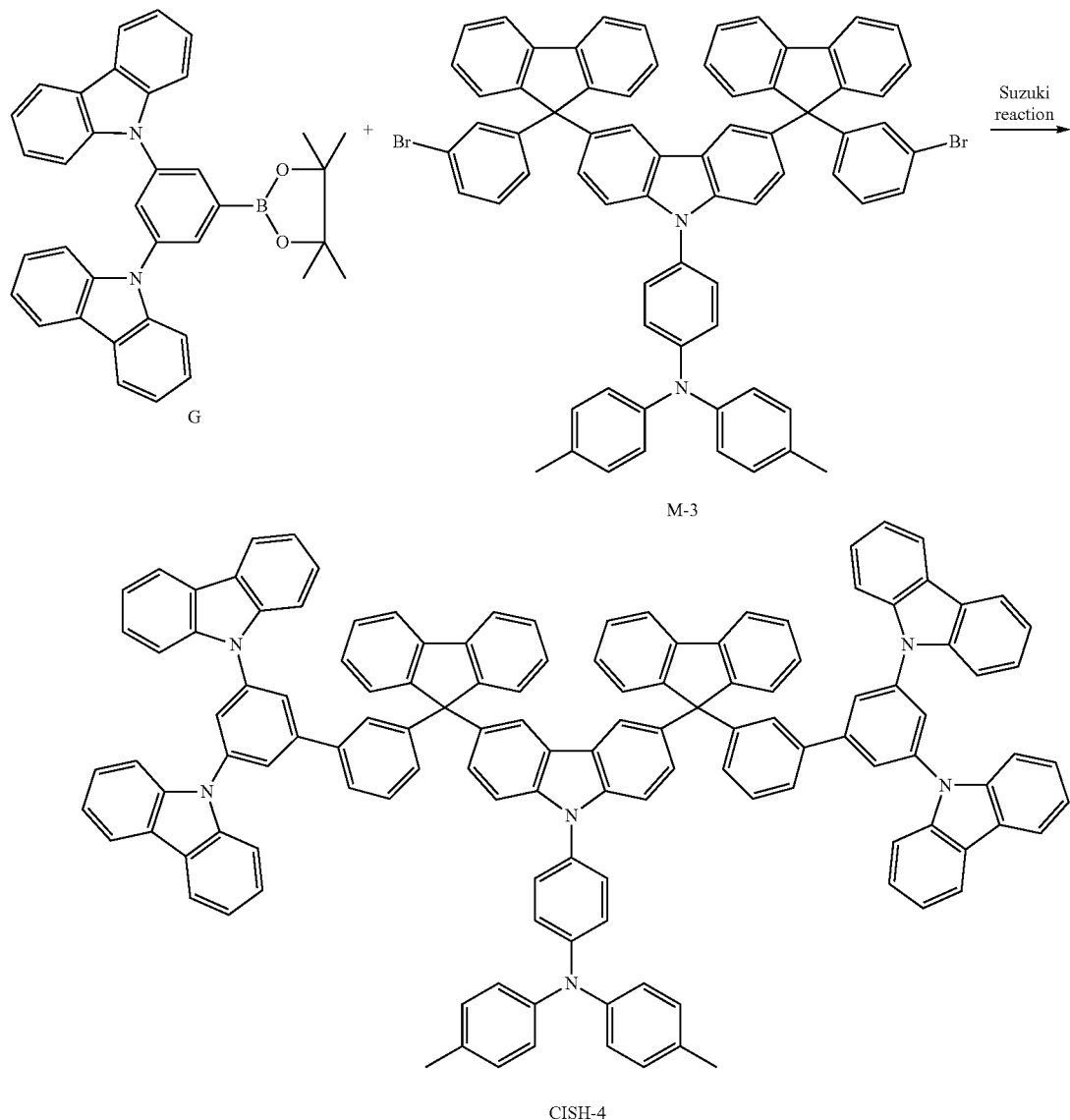

1.2 g (1.11 mmol) of M-3, 1.78 g (3.34 mmol) of a material G (3-(9H-carbazol-9-yl)-5-(4,4,5,5-tetramethyl-1,3,2-dioxaborolan-2-yl)phenyl)-9H-carbazole, and 0.06 g (0.05 mmol) of tetraistriphenylphosphinepalladium were dissolved in 30 mL of THF (tetrahydrofuran) in a 250 ml round flask with a thermometer, a reflux condenser, and an agitator under an argon atmosphere, and 15 mL of 20% tetratriethylammonium hydroxide was added thereto. The resulting mixture was refluxed for reaction at 75° C. for 48 hours.

When the reaction was complete, the reactant was cooled to room temperature. The reactant was extracted several times with methylenechloride, and was also washed several times with water.

Then, the reactant was treated with anhydrous magnesium sulfate to remove moisture. After it was filtered, the solvent was removed therefrom.

The reactant with no solvent was purified through a silica gel column using a solvent of methylenechloride/hexane mixed in a ratio of 1:2 and recrystallized a mixed solvent of acetone/hexane, obtaining 1.3 g (68%) of white CISH-4. This material had a maximum light emitting wavelength of 388 nm in a chloroform solution.

EXAMPLE 10
Synthesis of CISH-5
[Reaction Scheme 10]
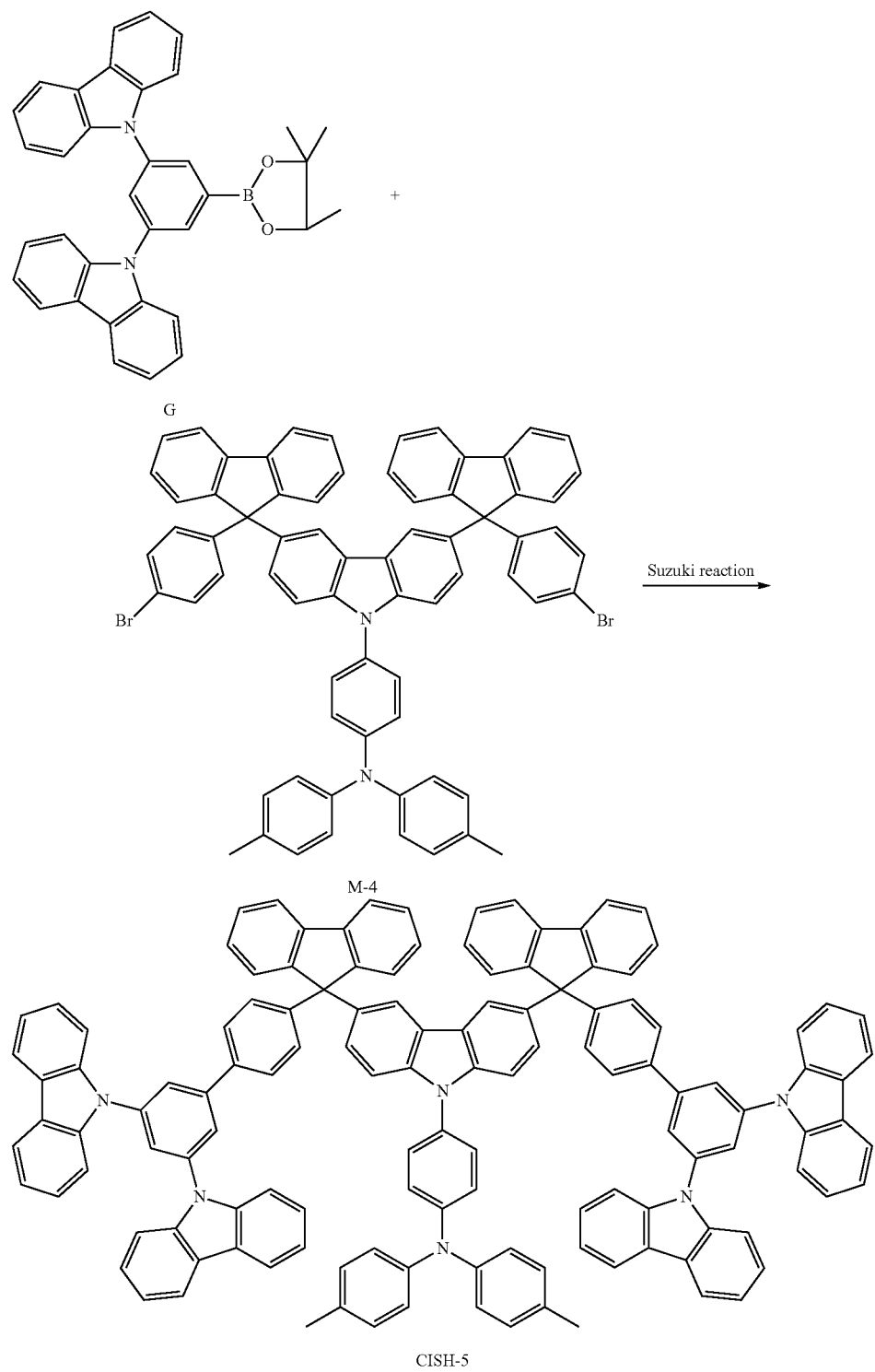
1.2 g (1.11 mmol) of M-4, 1.78 g (3.34 mmol) of a material G (3-(9H-carbazol-9-yl)-5-(4,4,5,5-tetramethyl-1,3,2-dioxaborolan-2-yl)phenyl)-9H-carbazole, and 0.06 g (0.05 mmol) of tetrakistriphenylphosphinepalladium were dissolved in 30 mL of THF (tetrahydrofuran) in a 250 ml round flask with a thermometer, a reflux condenser, and an agitator under an argon atmosphere, and 15 mL of 20% tetratriethylammonium hydroxide was added thereto. The resulting mixture was refluxed for reaction at 75° C. for 48 hours.

When the reaction was complete, the reactant was cooled to room temperature and then extracted several times with methylenechloride, and was also washed several times with water.

Then, the reactant was treated with anhydrous magnesium sulfate to remove moisture. After it was filtered, the solvent was removed therefrom.

The reactant with no solvent was purified through a silica gel column using a solvent of methylenechloride/hexane mixed in a ratio of 1:2 and recrystallized in a mixed solvent of acetone/hexane, obtaining 1.35 g (70%) of white CISH-5. This material had a maximum light emitting wavelength of 386 nm in a chloroform solution.

EXAMPLE 11

Synthesis of CISH-6

[Reaction Scheme 11]

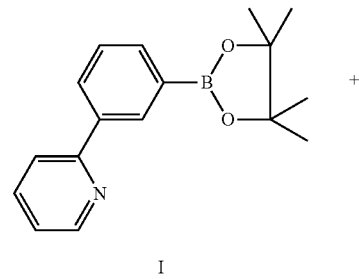

I

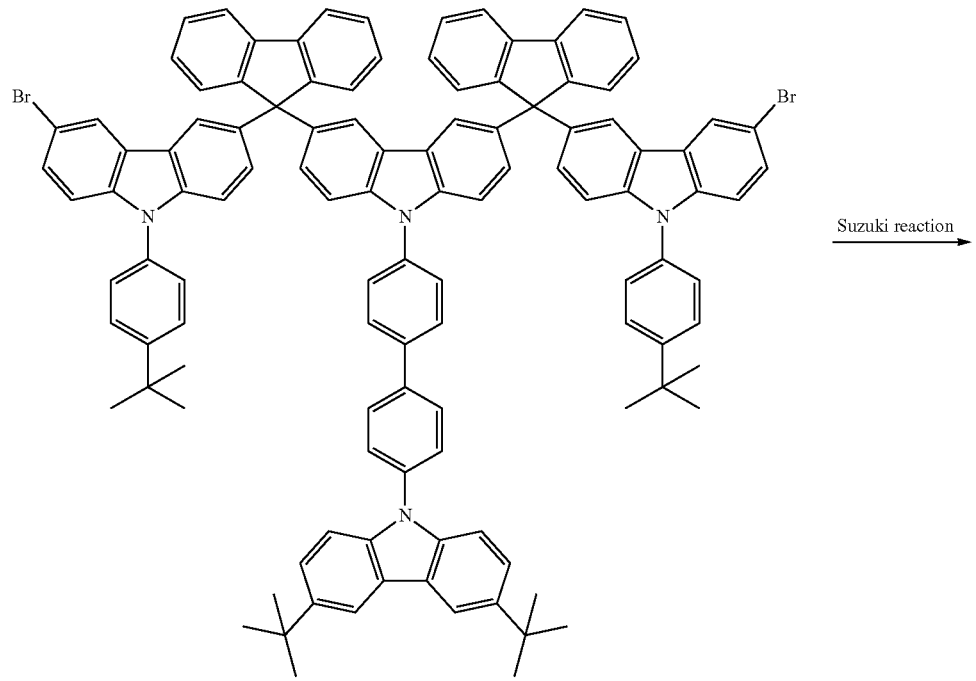

Suzuki reaction

M-5

-continued

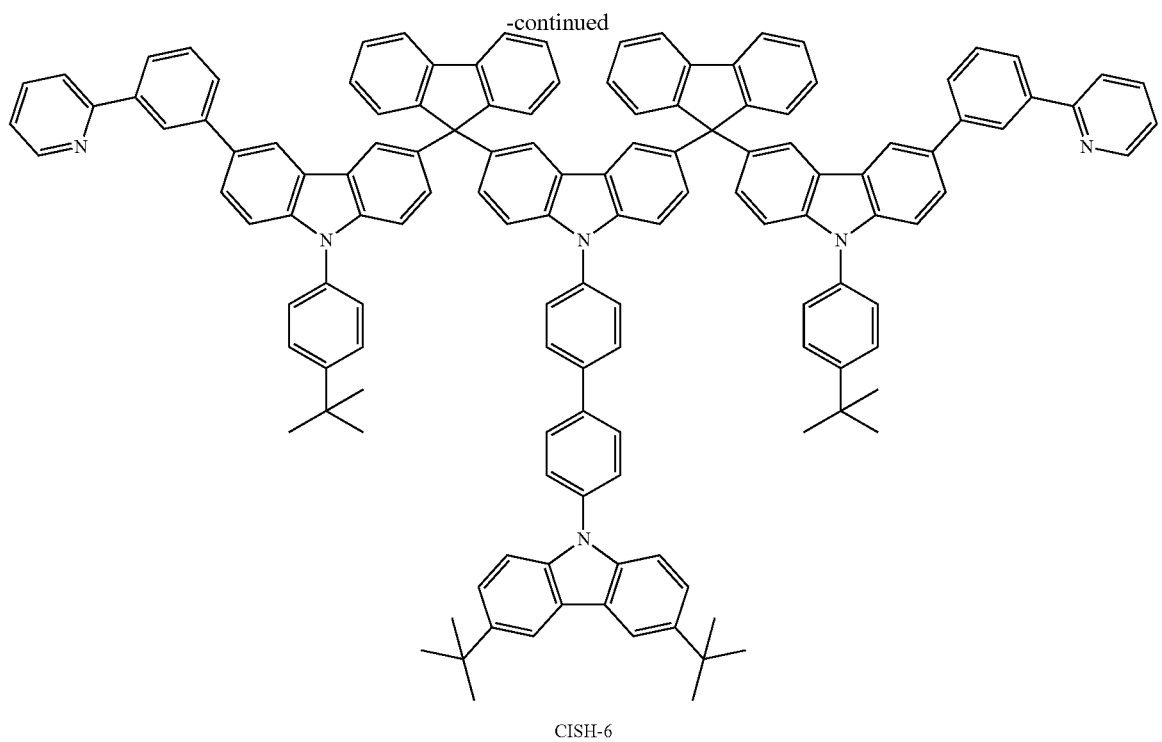

CISH-6

1.2 g (0.71 mmol) of M-5, 0.6 g (2.14 mmol) of a material I, and 0.05 g (0.043 mmol) of tetrakistriphenylphosphine-palladium were dissolved in 30 mL of THF (tetrahydrofuran) in a 250 ml round flask with a thermometer, a reflux condenser, and an agitator under an argon atmosphere, and 15 mL of 20% tetratriethylammonium hydroxide was added thereto. The resulting mixture was refluxed for reaction at 75° C. for 48.

When the reaction was complete, the reactant was cooled to room temperature and then extracted several times with methylenechloride, and was also washed several times with water.

Then, the reactant was treated with anhydrous magnesium sulfate to remove moisture. After it was filtered, the solvent was removed therefrom.

The reactant with no solvent was purified through a silica gel column using a solvent of methylenechloride/ethyl acetate mixed in a ratio of 9.8:0.2, obtaining 0.8 g (61.5%) of white CISH-6. This material had a maximum light emitting wavelength of 386 nm in a chloroform solution.

EXAMPLE 12

Synthesis of CISH-7

[Reaction Scheme 12]

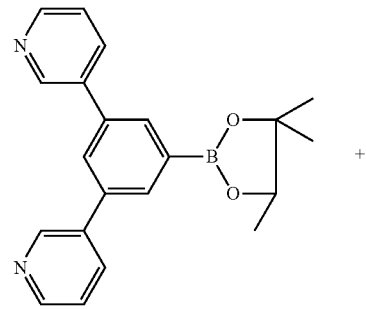

J

+

125    126
-continued
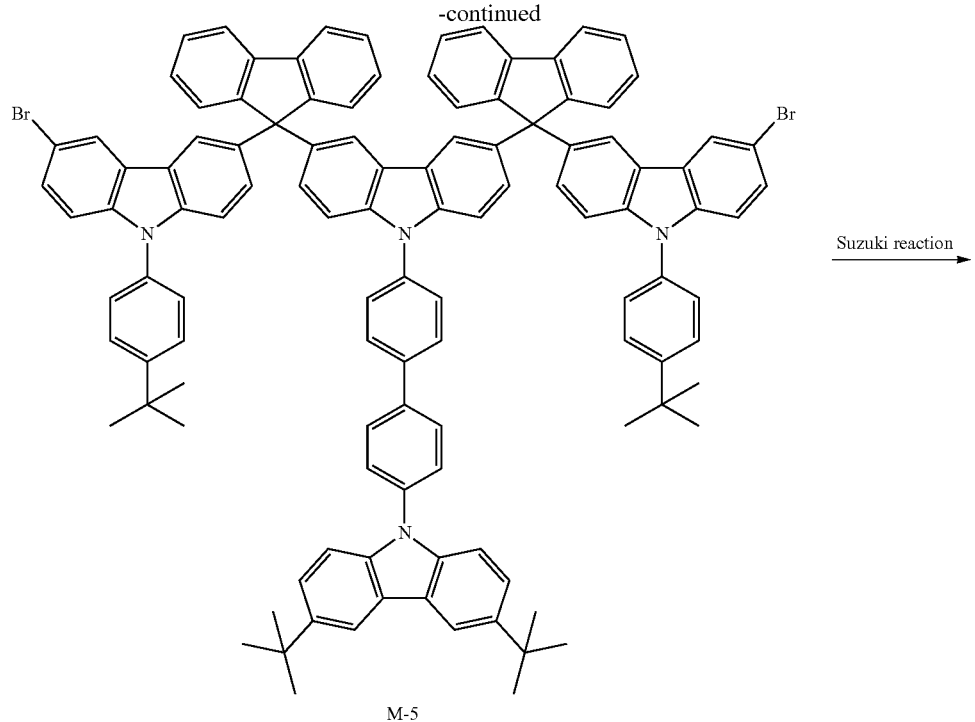
M-5
Suzuki reaction →
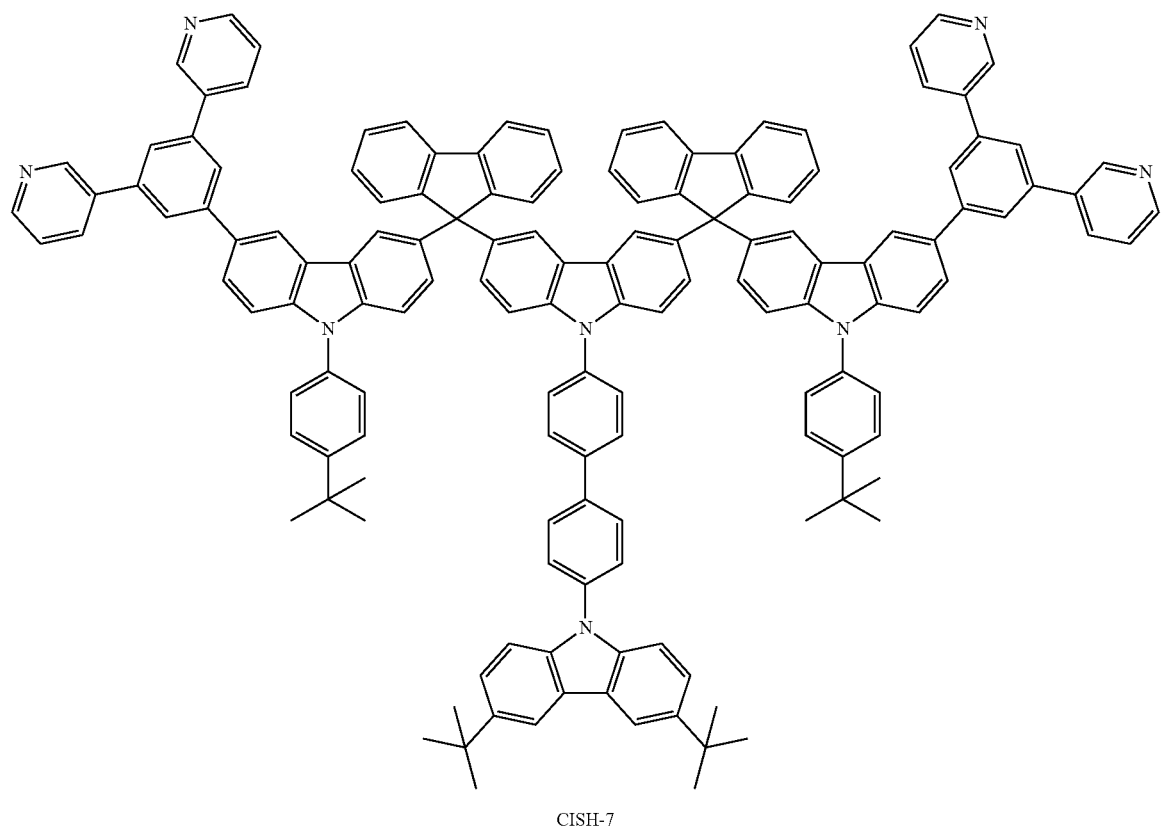
CISH-7

1.2 g (0.71 mmol) of M-5, 0.768 g (2.14 mmol) of a material J, and 0.05 g (0.043 mmol) of tetrakistriphenylphosphinepalladium were dissolved in 30 mL of THF (tetrahydrofuran) in a 250 ml round flask with a thermometer, a reflux condenser, and an agitator under an argon atmosphere, and 15 mL of 20% tetratriethylammonium hydroxide was added thereto. The resulting mixture was refluxed for reaction at 75° C. for 48 hours.

When the reaction was complete, the reactant was cooled to room temperature and then extracted several times with methylenechloride, and was also washed several times with water.

Then, the reactant was treated with anhydrous magnesium sulfate to remove moisture therefrom. After it was filtered, the solvent was removed therefrom.

The reactant with no solvent was purified through a silica gel column using a solvent of THF/ethylacetate mixed in a ratio ranging from 1:9 to 3:7, obtaining 0.5 g (35.4%) of white CISH-7. This material had a maximum light emitting wavelength of 387 nm in a chloroform solution.

EXAMPLE 13

Synthesis of CISH-8

[Reaction Scheme 13]

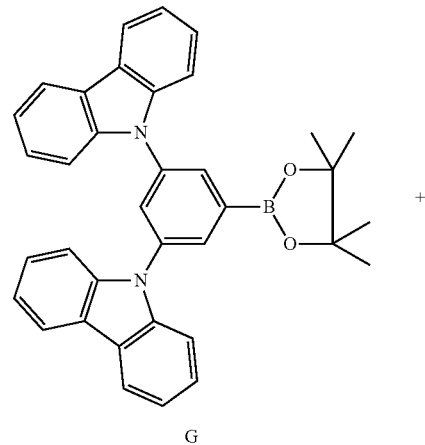

G

+

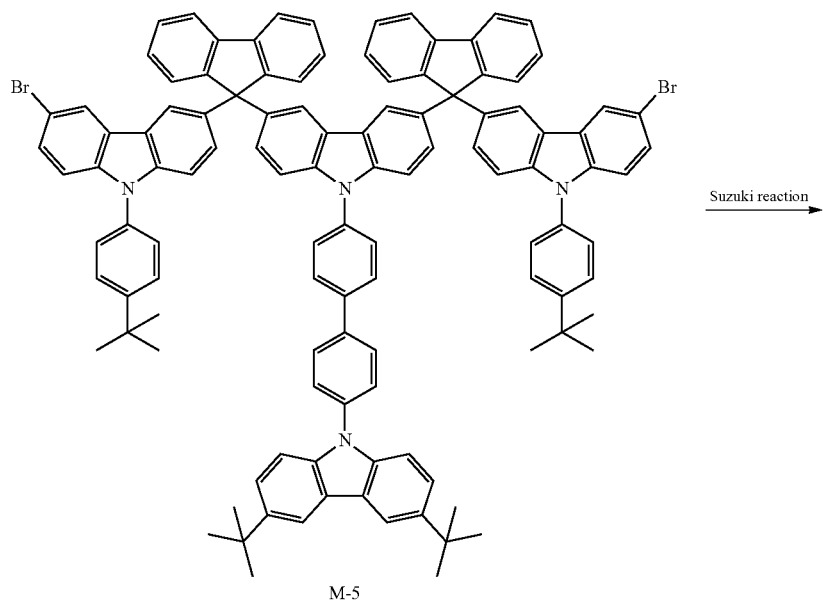

M-5

Suzuki reaction →

129                                                                                     130
-continued

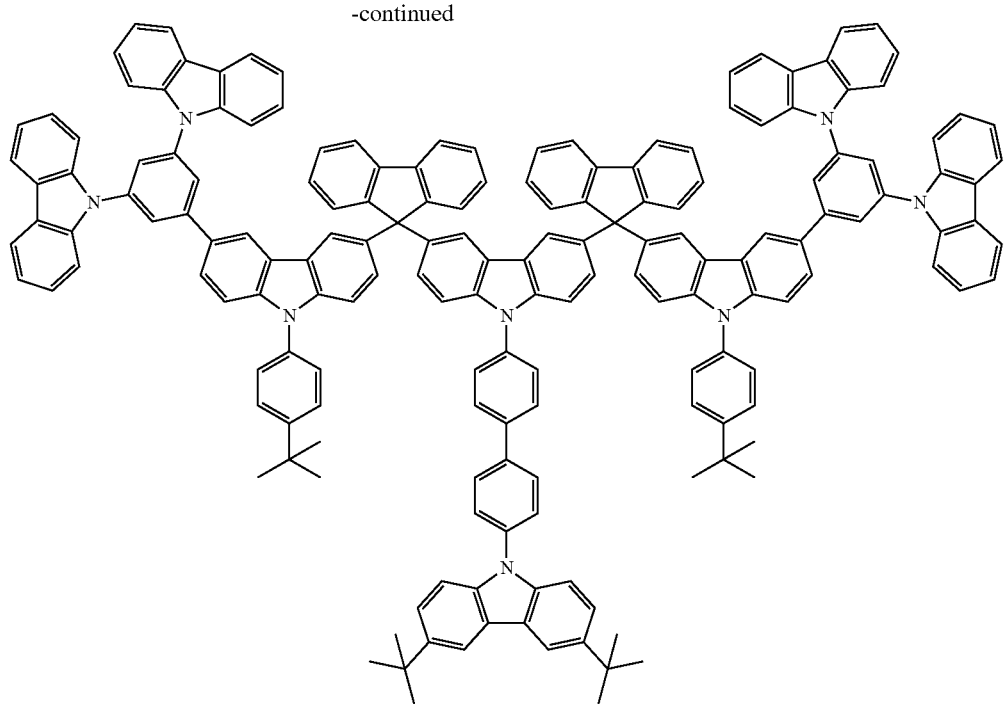

CISH-8

1.2 g (0.71 mmol) of M-5, 0.95 g (1.78 mmol) of a material G (3-(9H-carbazol-9-yl)-5-(4,4,5,5-tetramethyl-1,3,2-dioxaborolan-2-yl)phenyl)-9H-carbazole, and 0.05 g (0.043 mmol) of tetrakistriphenylphosphinepalladium were dissolved in 30 mL of THF (tetrahydrofuran) in a 250 ml round flask with a thermometer, a reflux condenser, and an agitator, and 15 mL of 20% tetratriethylammonium hydroxide was added thereto. The resulting mixture was refluxed for reaction at 75° C. for 48 hours.

When the reaction was complete, the reactant was cooled to room temperature and then extracted several times with methylenechloride, and was also washed several times with water.

Then, the reactant was treated with anhydrous magnesium sulfate to remove moisture. After it was filtered, the solvent was removed therefrom.

The reactant with no solvent was purified through a silica gel column using a solvent of methylenechloride/hexane mixed in a ratio of 2:3 and recrystallized with a mixed solvent of acetone/hexane, obtaining 0.9 g (54%) of white CISH-8.

This material had a maximum light emitting wavelength of 386 nm in a chloroform solution.

COMPARATIVE EXAMPLE 1
Synthesis of a Compound Represented by the Following Chemical Formula 127

[Chemical Formula 127]

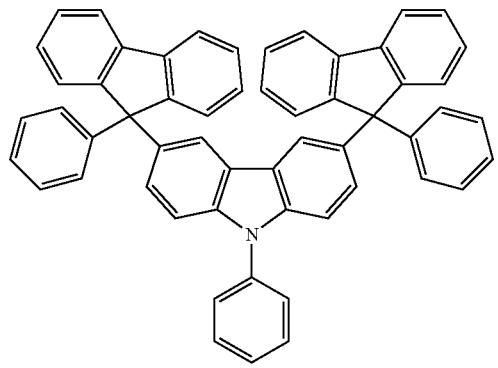

The compound of the above Chemical Formula 127 was synthesized according to the method described with reference to Organic Letters, 2006, 8, 2779.

Performance Evaluation of the Prepared Organic Compounds

Figure 2:
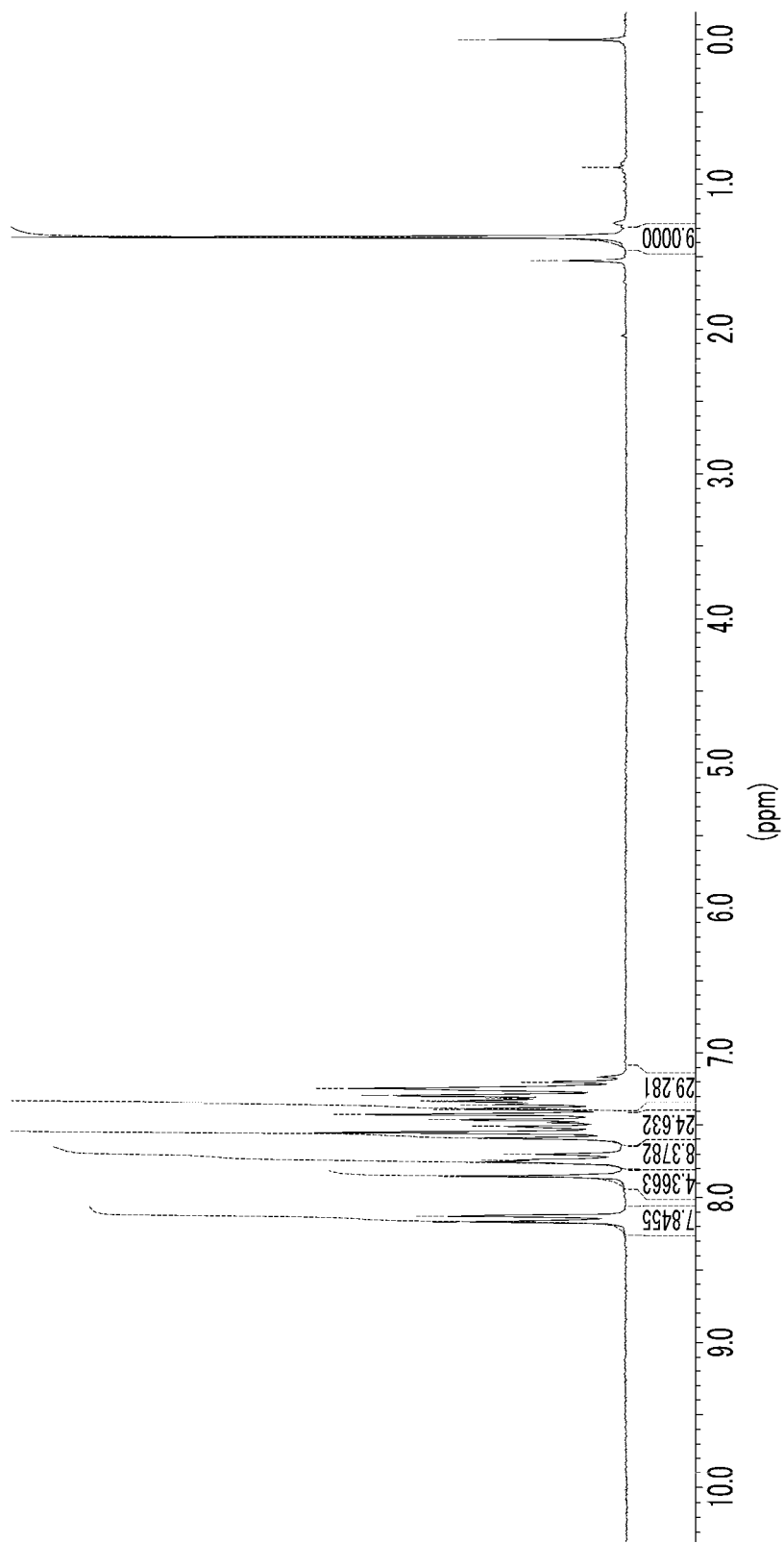
FIG. 2 shows a $^1$H-NMR spectrum of the organic compound according to Example 7.

The CISH-2 of Example 7 was measured regarding $^1$H-NMR using Bruker 300 MHz®. The result is shown in FIG. 2. Referring to FIG. 2, the organic compound of Example 7 was identified as CISH-2.

Figure 3:
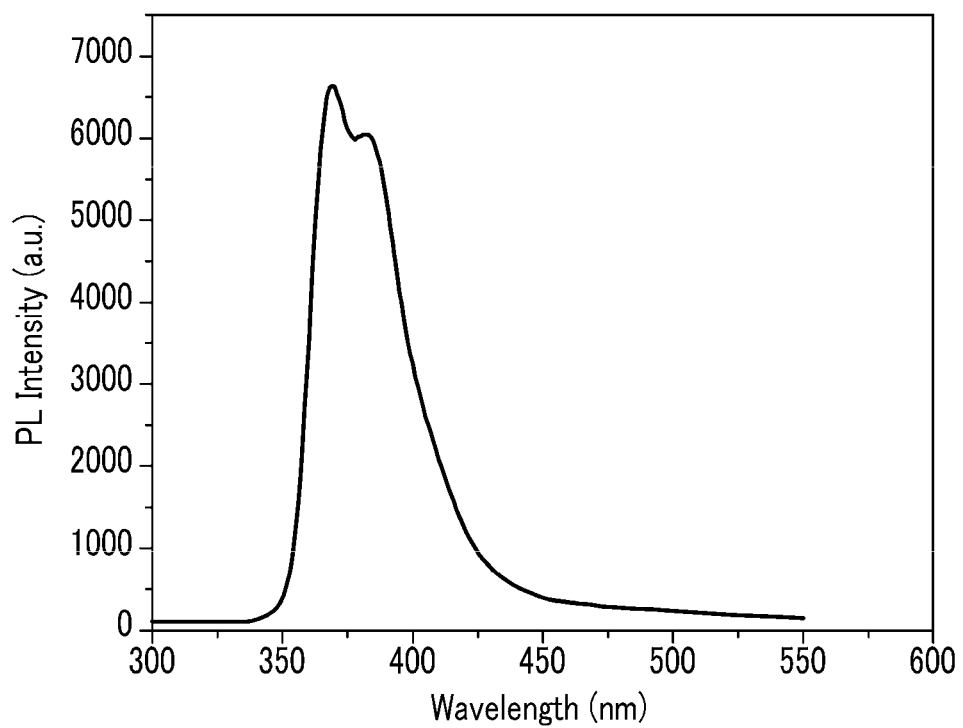
FIG. 3 is a graph showing PL (photoluminescence) wavelength of the organic compound according to Example 7.

In addition, the CISH-2 was used to form a thin film on a glass substrate and measured regarding photoluminescence (PL) wavelength using a HITACHI F-4500®. The result is shown in FIG. 3. Referring to FIG. 3, the CISH-2 was found to have a maximum light emitting wavelength of 368 nm, when it was made into a thin film.

Fabrication of an Organic Photoelectric Device

EXAMPLE 14

Fabrication of a Device Using Example 7 (CISH-2)

An ITO substrate was used as an anode, and poly(3,4-ethylenedioxy-thiophene) (PEDOT) was spin-coated thereon.

Next, an emission layer was formed on the PEDOT by doping Ir(mppy)$_3$ in an amount of 6 to 7% as a dopant into CISH-2.

Then, a 50 Å-thick hole-blocking layer was formed by vacuum-depositing BAlq on the emission layer.

Then, a 200 Å-thick electron transport layer (ETL) was formed on the emission layer by vacuum-depositing Alq$_3$.

Subsequently, LiF 10 Å and Al 1000 Å were sequentially vacuum-deposited on the electron transport layer (ETL) to form a cathode, completing an organic photoelectric device.

As for a comparison reference device structure, PVK was used as a polymer host.

Herein, an evaluation device structure included Al 1000 Å/LiF 10 Å/Alq$_3$ 200 Å/BAlq 50 Å/EML (CISH-2+Ir(mppy)$_3$)/PEDOT/ITO 1500 Å. A comparison reference device structure included Al 1000 Å/LiF 10 Å/Alq$_3$ 200 Å/BAlq 50 Å/EML (PVK+Ir(mppy)$_3$)/PEDOT/ITO 1500 Å.

EXAMPLE 15

Fabrication of a Device Using Example 9 (CISH-4)

An organic photoelectric device was fabricated using the same method as Example 14, except that CISH-4 was used instead of CISH-2 as a compound of an emission layer.

COMPARATIVE EXAMPLE 2

Fabrication of a Device Using Comparative Example 1

An organic photoelectric device was fabricated using the same method as Example 14, except that a compound of Comparative Example 1 was used instead of CISH-2 as a compound of an emission layer.

COMPARATIVE EXAMPLE 3

Fabrication of a Device Using poly(9-vinylcarbazole)

An organic photoelectric device was fabricated using the same method as Example 14, except that poly(9-vinylcarbazole) was used instead of CISH-2 as a compound of an emission layer.

Performance Evaluation of the Organic Photoelectric Device

The organic photoelectric device of Example 14 was measured regarding output efficiency and luminance changes depending on voltage change. The results are respectively shown in FIGS. 4 and 5.

In addition, its threshold voltage, driving voltage, current efficiency, and electrical power efficiency at 1000 nit were measured. The results are shown in the following Table 1.

TABLE 1

| | | At 1000 nit | | | |
|---|---|---|---|---|---|
| | Device | Threshold voltage (V) | Driving voltage (V) | Current efficiency (cd/A) | Electrical power efficiency (lm/W) |
| Green | Comparative Example 3 | 2.8 | 7.2 | 4.75 | 2.07 |
| | Example 14 | 2.8 | 7.4 | 6.58 | 2.79 |

Figure 4:
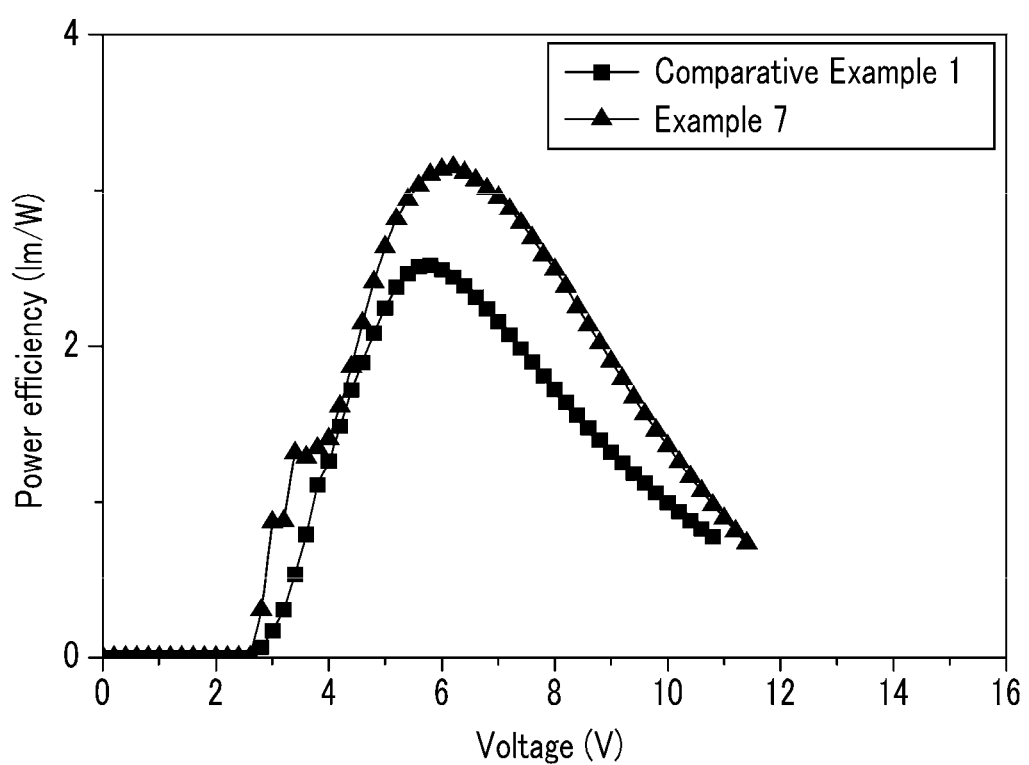
FIG. 4 is a graph showing output efficiency of the organic photoelectric device including the organic compound according to Example 7.
Figure 5:
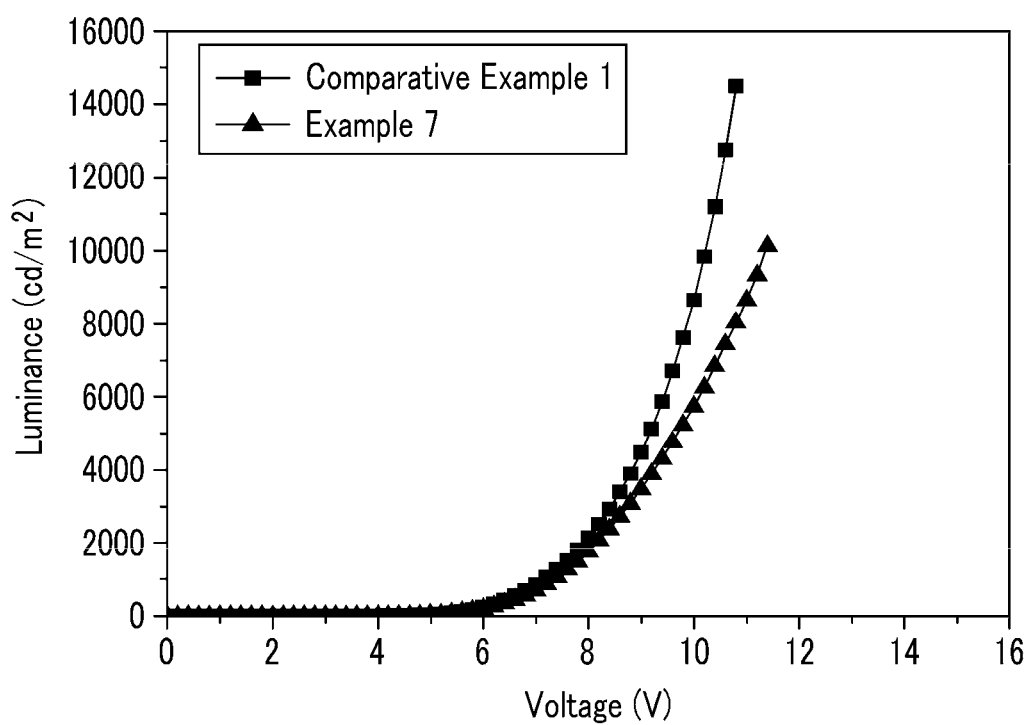
FIG. 5 is a graph showing voltage-luminance of the organic photoelectric device including the organic compound according to Example 7.

Referring to FIGS. 4 and 5 and Table 1, an organic compound of the present invention can be used as a host material for an organic photoelectric device.

(Measurement of Characteristics of Compound)

DSC, TGA of the compounds of Examples 7 and 9, and Comparative Example 1 were measured, and the glass transition temperature, the decomposition temperature, the melting point, and the triplet exciton energy level were compared.

Figure 6A:
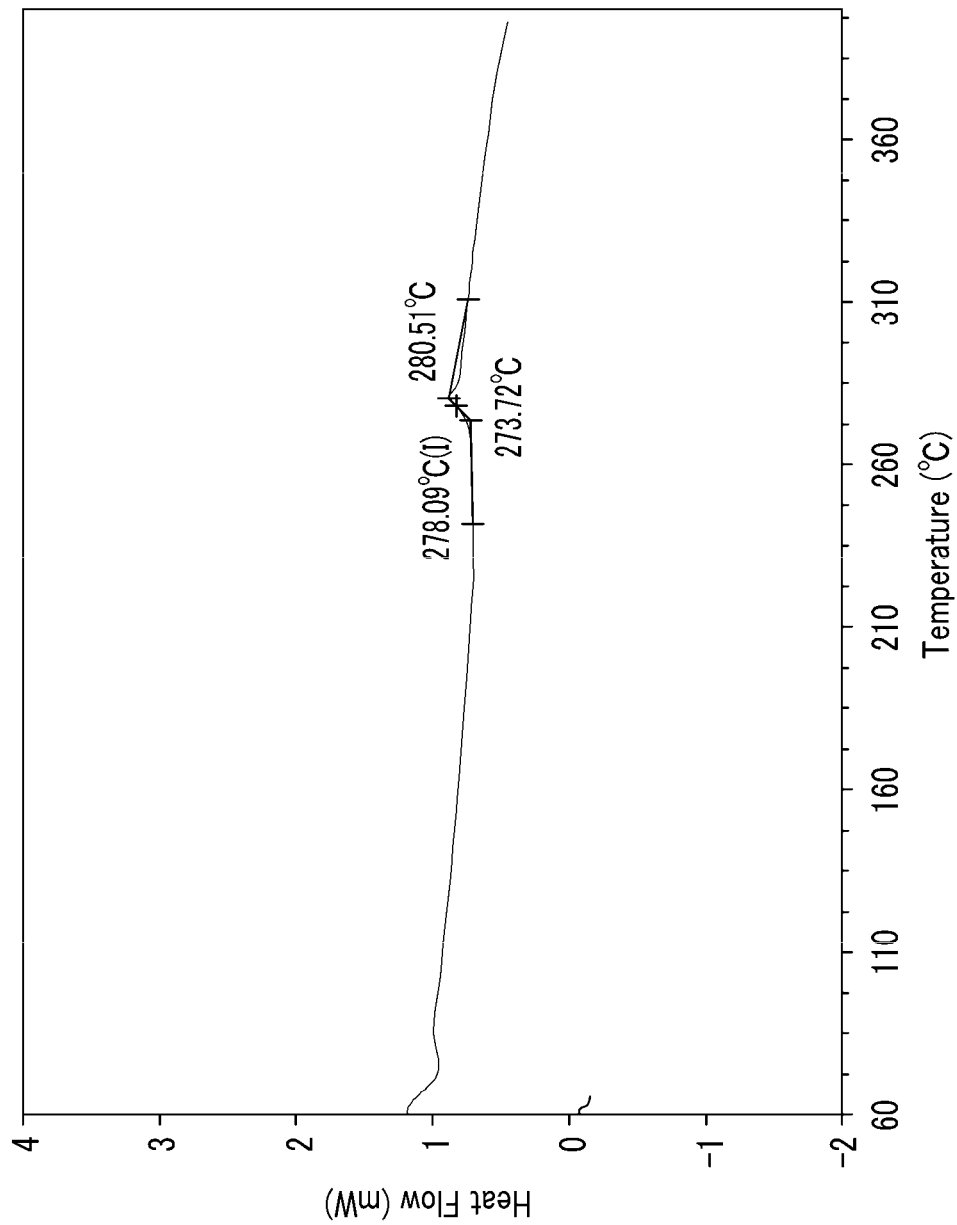
FIG. 6A shows a differential scanning calorimetry (DSC) result of Example 7.
Figure 6B:
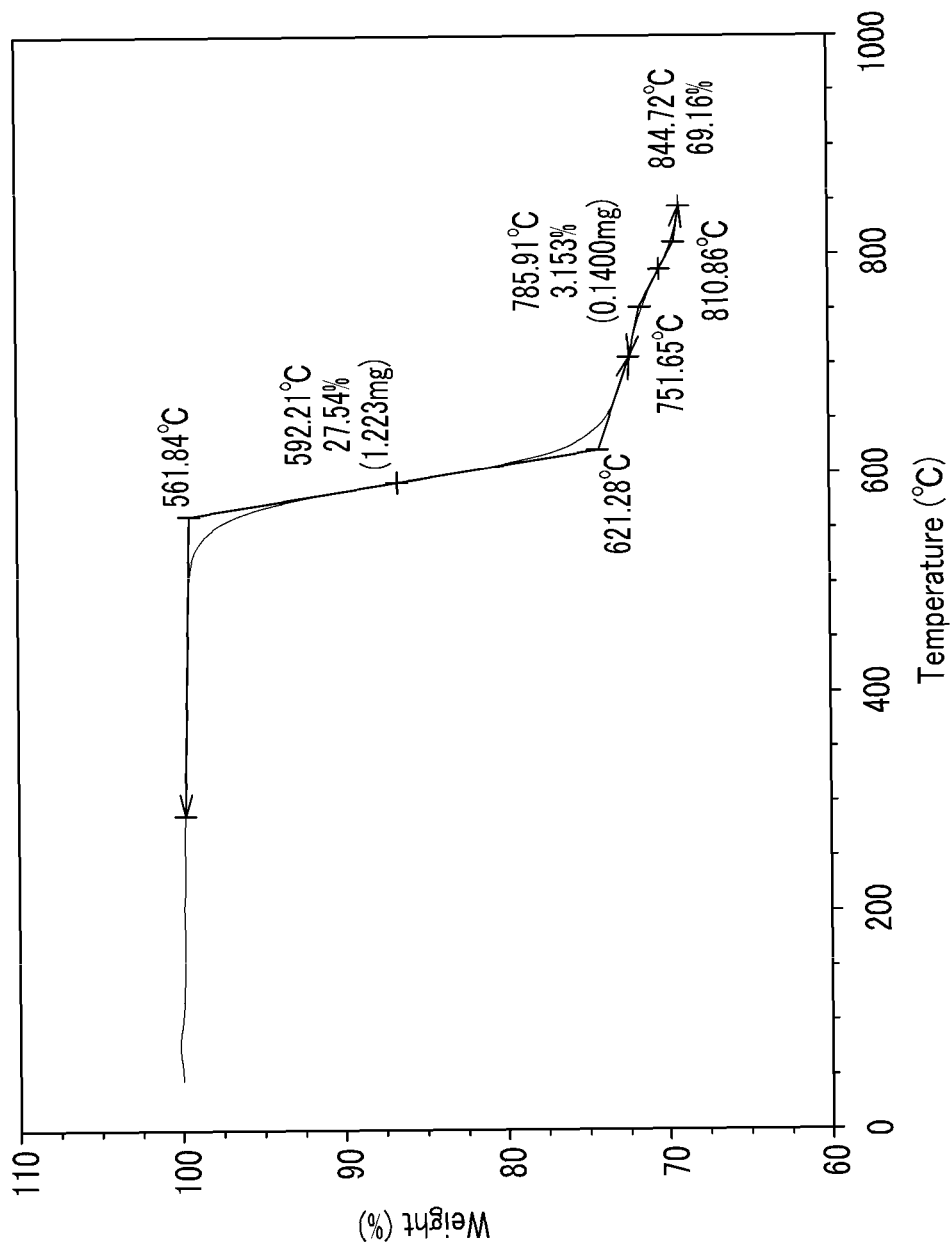
FIG. 6B shows a thermogravimetric analysis (TGA) result of Example 7.

FIG. 6A shows the result of differential scanning calorimetry (DSC) of Example 7, and FIG. 6B shows the result of a thermogravimetric analysis (TGA) of Example 7.

Figure 7A:
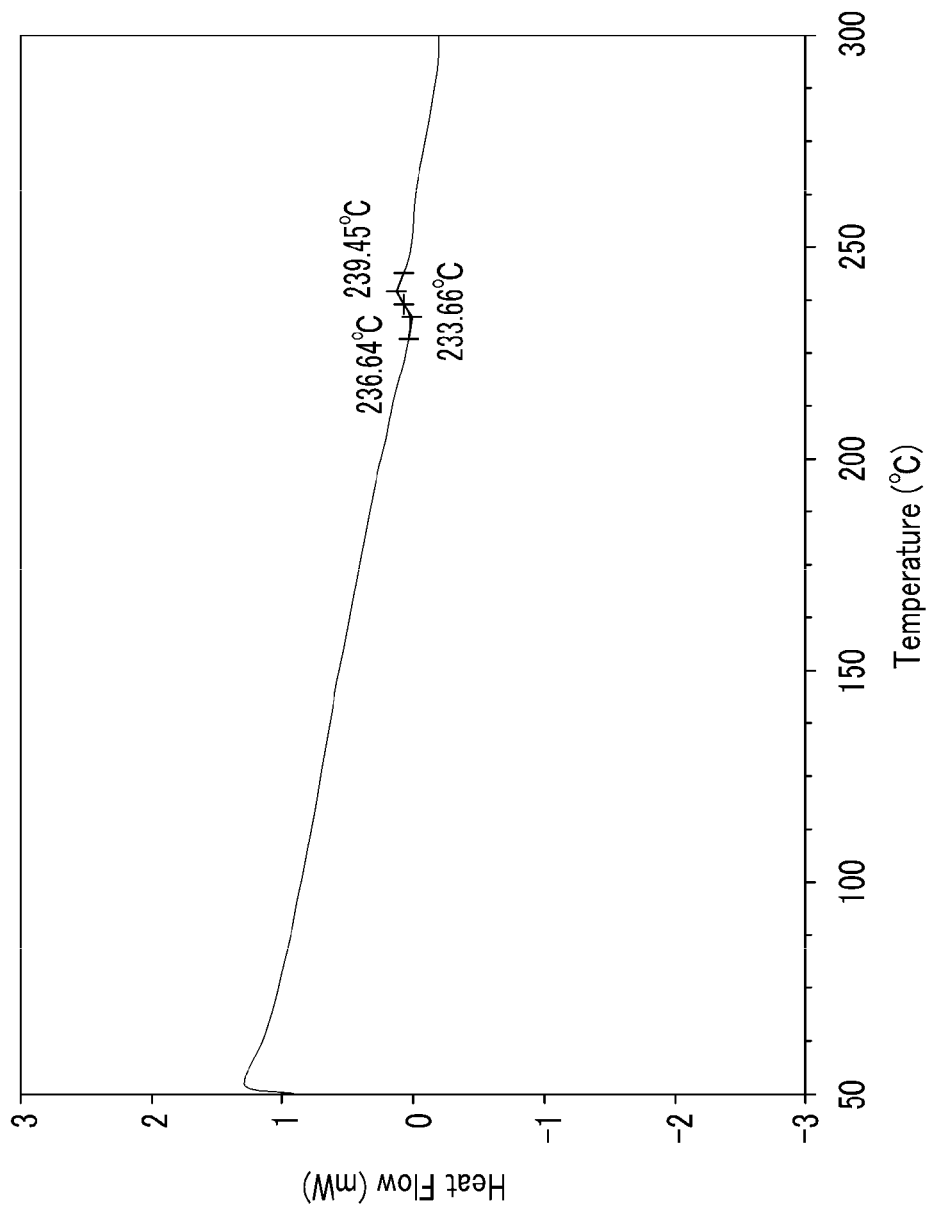
FIG. 7A shows a DSC result of Example 10.
Figure 7B:
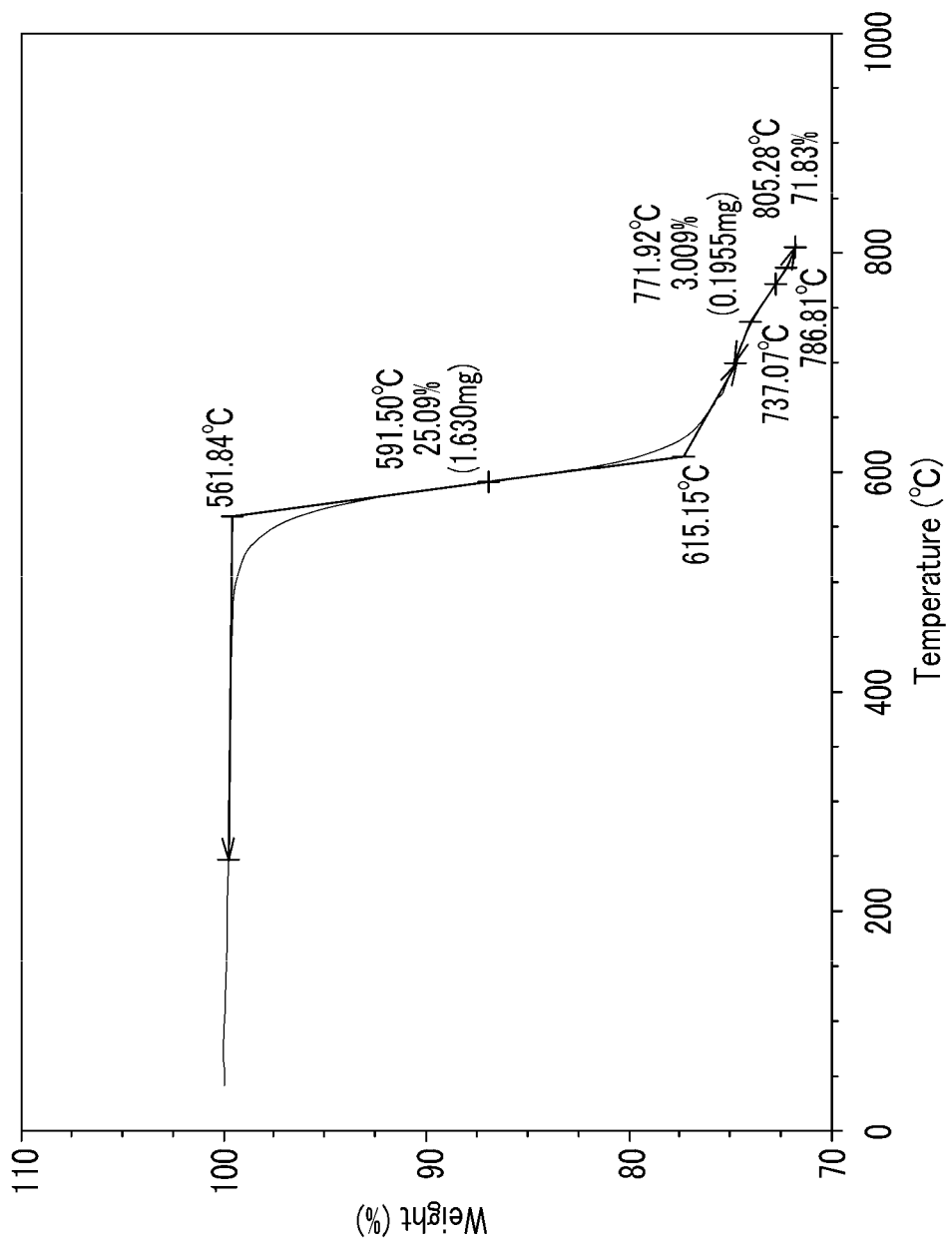
FIG. 7B shows a TGA result of Example 10.

FIG. 7A shows the result of DSC of Example 10, and FIG. 7B shows the result of a TGA of Example 10.

The results of FIGS. 6A, 6B, 7A, and 7B are as shown in the following Table 2.

TABLE 2

| Material | Tg | Tm | Td |
|---|---|---|---|
| Comparative Example 1 | 171 | 328 | 429 |
| Example 7 | 278 | N.D | 561 |
| Example 9 | 236 | N.D | 560 |

Tg: glass transition temperature
Tm: melting point
Td: decomposition temperature
N.D: Not determined The thermal property data of the compound of Comparative Example 1 is referred to with reference to Chinese Patent Laid-Open Publication No. CN1769269 A.

As shown in Table 2, Examples 7 and 9 have remarkably improved thermal properties compared with Comparative Example 1.

The thermal stability of a compound as a material remarkably affects the life-span of a device, and as a person of ordinary skill in the art can understand this, a device prepared according to Examples 7 and 9 is expected to have an excellent life-span compared to a device prepared according to Comparative Example 1.

(Evaluation of Efficiency of Organic Photoelectric Device)

Efficiency of the organic photoelectric devices according to Examples 14 and 15 and Comparative Example 2 were evaluated. The results are shown in FIGS. 8A and 8B.

Figure 8A:
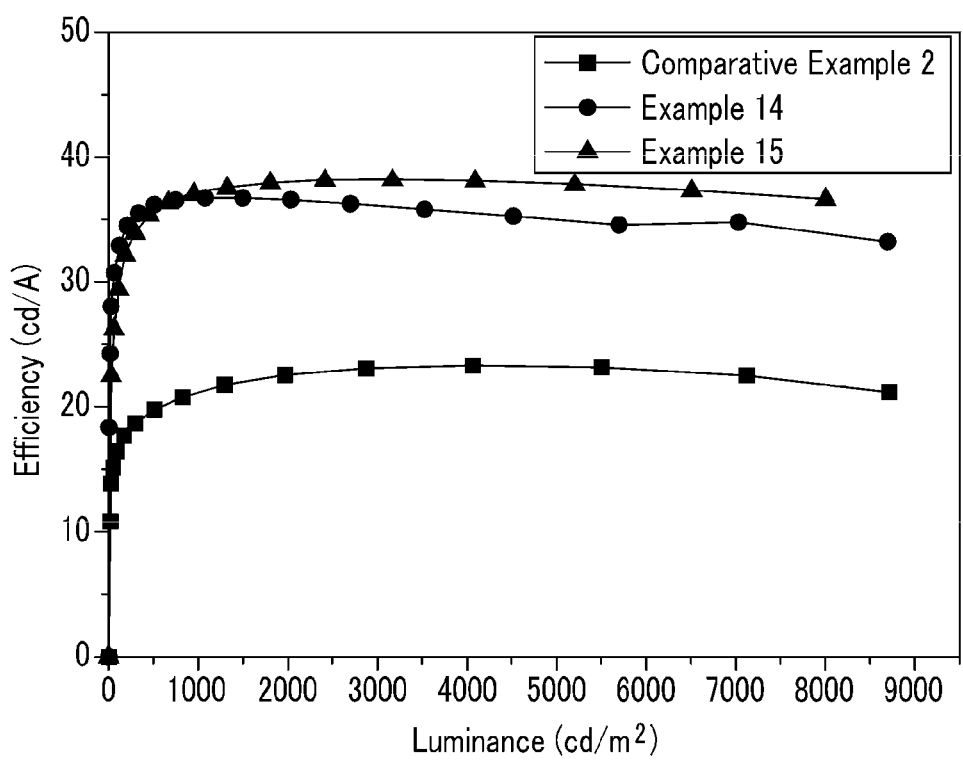
FIG. 8A shows luminous efficiency data of Examples 14 and 15 and Comparative Example 2.
Figure 8B:
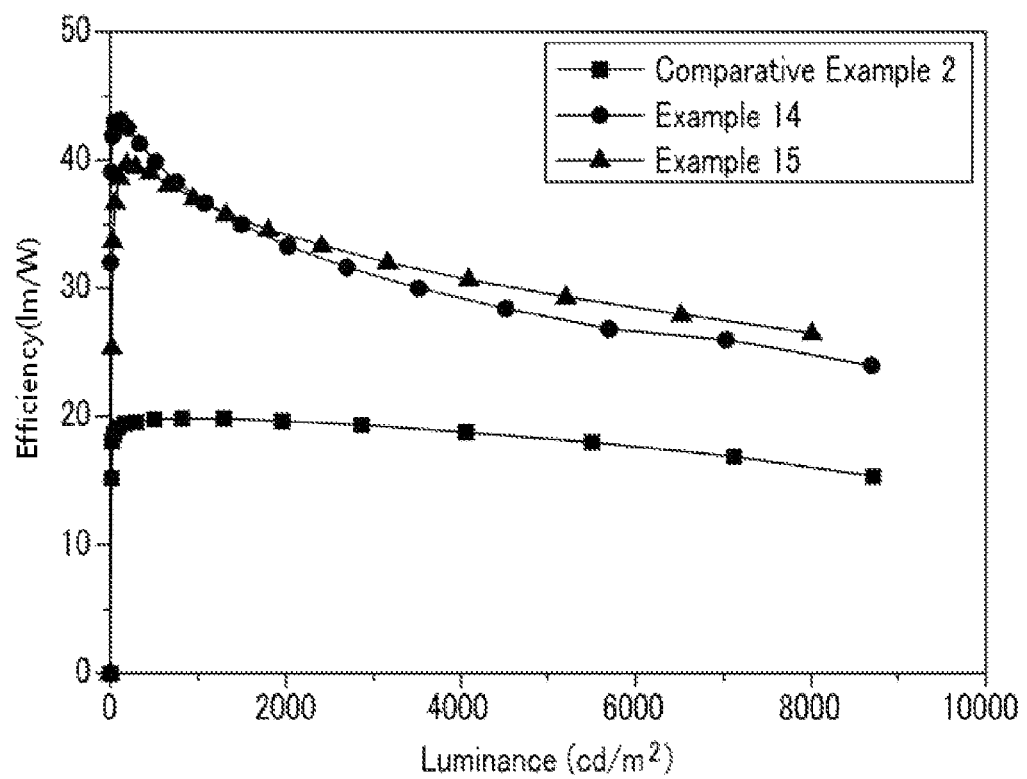
FIG. 8B shows electrical power efficiency data of Examples 14 and 15 and Comparative Example 2.

FIG. 8A shows luminous efficiency data of Examples 14 and 15 and Comparative Example 2, and FIG. 8B shows electrical power efficiency data of Examples 14 and 15 and Comparative Example 2.

As for Comparative Example 2, the material used did not have a bulky structure without a substituent, and since the device was prepared with the material through a solution process, the thin film characteristics were poor, and the device characteristics were remarkably deteriorated due to low thermal stability.

However, the device prepared according to Examples 14 and 15 had remarkably increased thermal stability and thin film characteristics because the material used had a bulky structure including a hetero aryl at the terminal end, and had increased molecular weight, and therefore it had excellent device characteristics.

(Evaluation of Thin Film Characteristics)

The compounds of Comparative Example 1 and Examples 7 and 9 were used to form an emission layer of an organic photoelectric device through a solution process, and the surfaces of the prepared layers were compared with an atomic force microscope (AFM).

Figure 9A:
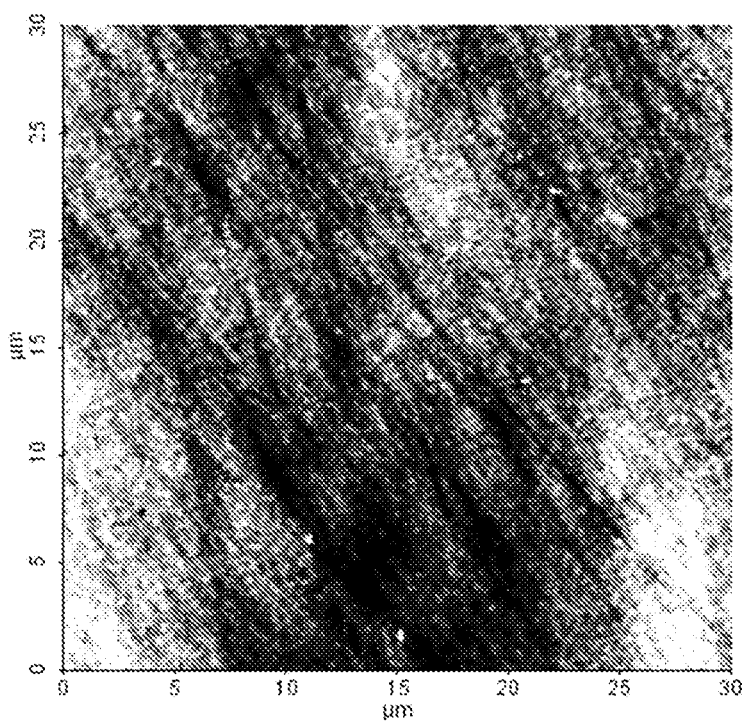
FIG. 9A shows a topography image after forming an emission layer according to Comparative Example 1.
Figure 9B:
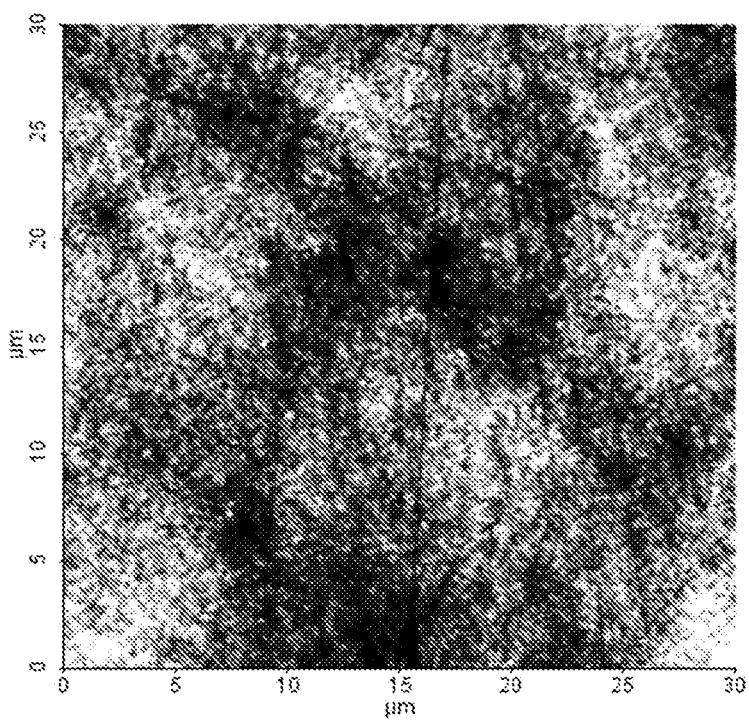
FIG. 9B shows a topography image after forming an emission layer according to Example 7.
Figure 9C:
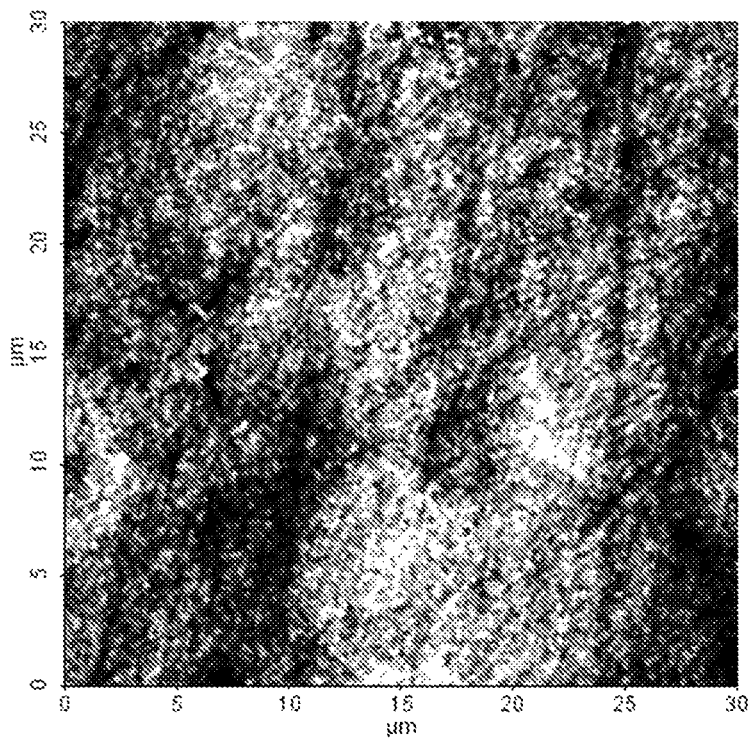
FIG. 9C shows a topography image after forming an emission layer according to Example 9.

FIG. 9A shows a topography image of an emission layer according to Comparative Example 1, FIG. 9B shows a topography image of an emission layer according to Example 7, and FIG. 9C shows a topography image of an emission layer according to Example 9.

Rq was surface roughness measured with the AFM.

TABLE 3

| Compound | Rq (nm) |
| --- | --- |
| Comparative Example 1 | 0.876 |
| Example 7 | 0.520 |
| Example 9 | 0.645 |

The compounds of Examples 7 and 9 are suitable materials for an organic photoelectric device for a solution process, and as shown in Table 3, when an emission layer is formed through a solution process using the compounds, it has low Rq which is surface roughness.

A low Rq refers to low surface roughness indicating that the surface may be formed very uniformly.

As a result of crystallinity of a resulting material, Comparative Example 1 having a light molecular weight has bad surface roughness of an emission layer due to crystallization of a compound through a solution process.

As shown in Table 3, Examples 7 and 9 have superb molecular weight compared with Comparative Example 1 because they have a structure including a heteroaryl substituent at the terminal end thereof, and the substituent prevents crystallization of a compound and recrystallization after a solution process does not occur. The benefit not only accrues because of the molecular weight of Examples 7 and 9, but also because of low tacticity of the compound.

Therefore, as shown in Table 3, the surface roughness of Examples 7 and 9 is low.

When the surface roughness is increased the device characteristics are remarkably decreased, as is well known to a person of ordinary skill in the art.

It is therefore absolutely expected that the organic photoelectric device prepared according to Examples 7 and 9 may have excellent device characteristics compared to the organic photoelectric device prepared according to Comparative Example 1.

(Evaluation of Optical Characteristics of Organic Photoelectric Device)

Optical characteristics of the organic photoelectric devices according to Example 14 and Comparative Example 2 were evaluated.

Figure 10A:
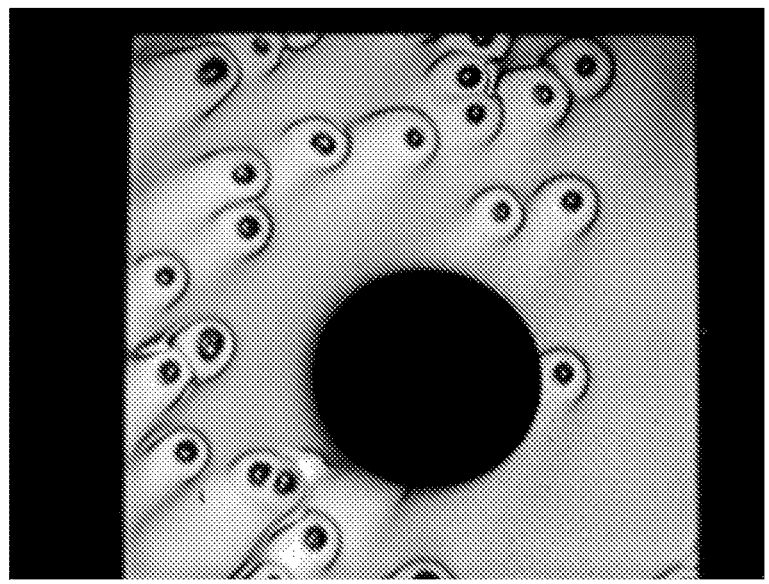
FIG. 10A is a photograph showing light emission of a device of Comparative Example 2.
Figure 10B:
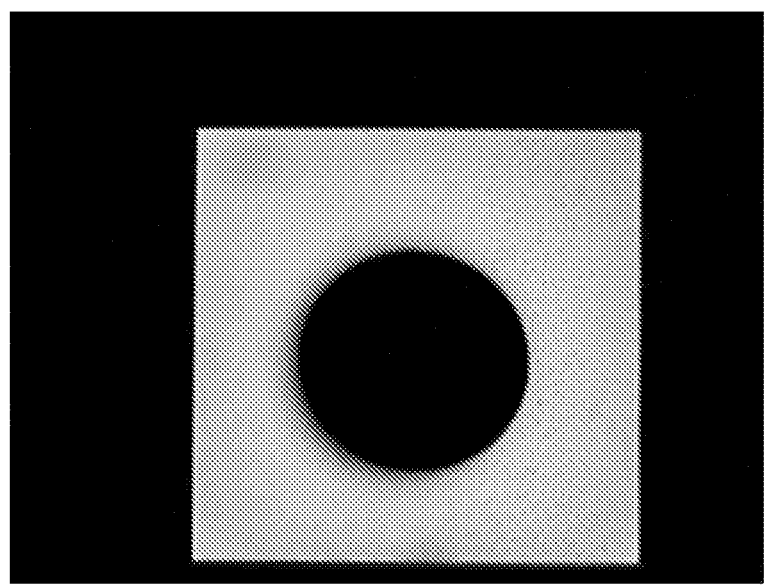
FIG. 10B is a photograph showing light emission of a device of Example 14.

FIG. 10A shows a light emission photograph of the device of Comparative Example 2, and FIG. 10B shows a light emission photograph of the device of Example 14.

As shown in the photographs of FIGS. 10A and 10C, when the compound of Comparative Example 1 that is a compound of the emission layer of Comparative Example 2 is formed as a thin film with a dopant during a solution process, it has a light molecular weight as well as a firm structure, and therefore it is easily recrystallized during thin film conditions.

The recrystallization of a host used for an emission layer causes non-uniform light emission and shortens the life-span of a device.

The device of Example 14 using the compound of Example 7 shows very uniform light emission. Therefore, recrystallization is remarkably decreased.

The present invention is not limited to the embodiments illustrated with the drawings and table, but can be fabricated into various modifications and equivalent arrangements included within the spirit and scope of the appended claims by a person who is ordinarily skilled in this field. Therefore, the aforementioned embodiments should be understood to be exemplary but not limiting the present invention in any way.

What is claimed is:

1. An organic compound represented by the following Chemical Formula 1:

[Chemical Formula 1]

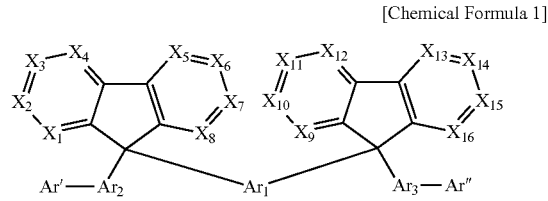

wherein, in the above Chemical Formula 1, $X_1$ to $X_{16}$ are the same or different, and are independently selected from CR' and N, $Ar_1$ is selected from a substituted or unsubstituted C6 to C30 arylene group, and a substituted or unsubstituted C2 to C30 heteroarylene group, provided that when $Ar_1$ includes a carbazolylene moiety, the carbazolylene moiety is N-bonded with a substituted phenyl, $Ar_2$ to $Ar_3$ are the same or different, and are independently selected from a substituted or unsubstituted C6 to C30 arylene group, and a substituted or unsubstituted C2 to C30 heteroarylene group, Ar' and Ar" are the same or different, and are independently selected from a substituted or unsubstituted C6 to C30 aryl group, and a substituted or unsubstituted C2 to C30 heteroaryl group, and R' is independently selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthio group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, and a substituted or unsubstituted C3 to C40 silyl group.

2. The organic compound of claim 1, wherein,

Ar$_1$ is selected from a carbazole N-bonded with a substituted phenyl, a substituted or unsubstituted arylamine, a substituted or unsubstituted phenyl, a substituted or unsubstituted tolyl, a substituted or unsubstituted naphthyl, a substituted or unsubstituted stilbene, a substituted or unsubstituted fluorenyl, a substituted or unsubstituted anthracenyl, a substituted or unsubstituted terphenyl, a substituted or unsubstituted pyrenyl, a substituted or unsubstituted diphenyl anthracenyl, a substituted or unsubstituted dinaphthylanthracenyl, a substituted or unsubstituted pentacenyl, a substituted or unsubstituted bromophenyl, a substituted or unsubstituted hydroxyphenyl, a substituted or unsubstituted thienyl, a substituted or unsubstituted pyridyl, a substituted or unsubstituted azobenzenyl, and a substituted or unsubstituted ferrocenyl, Ar$_2$ to Ar$_3$ are the same or different, and are independently selected from a substituted or unsubstituted carbazole, a substituted or unsubstituted arylamine, a substituted or unsubstituted phenyl, a substituted or unsubstituted tolyl, a substituted or unsubstituted naphthyl, a substituted or unsubstituted stilbene, a substituted or unsubstituted fluorenyl, a substituted or unsubstituted anthracenyl, a substituted or unsubstituted terphenyl, a substituted or unsubstituted pyrenyl, a substituted or unsubstituted diphenyl anthracenyl, a substituted or unsubstituted dinaphthylanthracenyl, a substituted or unsubstituted pentacenyl, a substituted or unsubstituted bromophenyl, a substituted or unsubstituted hydroxyphenyl, a substituted or unsubstituted thienyl, a substituted or unsubstituted pyridyl, a substituted or unsubstituted azobenzenyl, and a substituted or unsubstituted ferrocenyl, and Ar' and Ar" are the same or different, and are independently selected from a substituted or unsubstituted carbazole, a substituted or unsubstituted arylamine, a substituted or unsubstituted phenyl, a substituted or unsubstituted naphthyl, a substituted or unsubstituted anthracenyl, a substituted or unsubstituted fluorene, a substituted or unsubstituted thiophene, a substituted or unsubstituted pyrrole, a substituted or unsubstituted pyridine, a substituted or unsubstituted aryloxadiazole, a substituted or unsubstituted triazole, and a substituted or unsubstituted arylsilane.

3. The organic compound of claim 1, wherein Ar' and Ar" the same or different, and are independently selected from the substituents of the following Chemical Formulae 2 to 31:

[Chemical Formula 2]

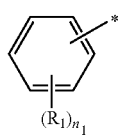

[Chemical Formula 3]

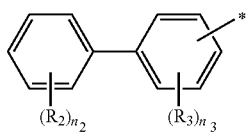

[Chemical Formula 4]

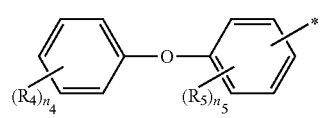

[Chemical Formula 5]

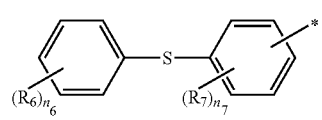

[Chemical Formula 6]

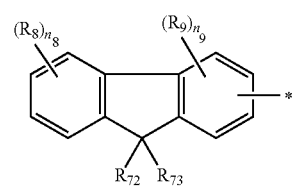

[Chemical Formula 7]

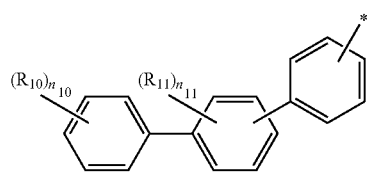

[Chemical Formula 8]

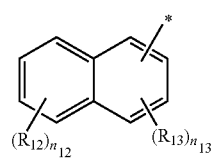

[Chemical Formula 9]

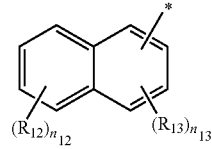

[Chemical Formula 10]

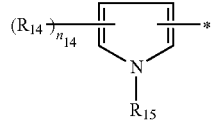

[Chemical Formula 11]

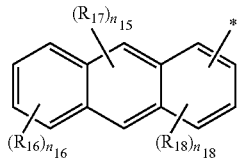

[Chemical Formula 12]

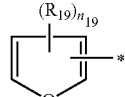

[Chemical Formula 13]
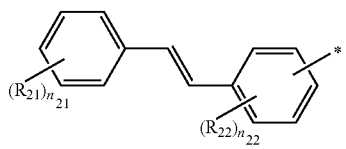
[Chemical Formula 14]
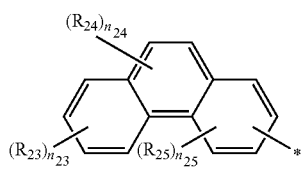
[Chemical Formula 15]
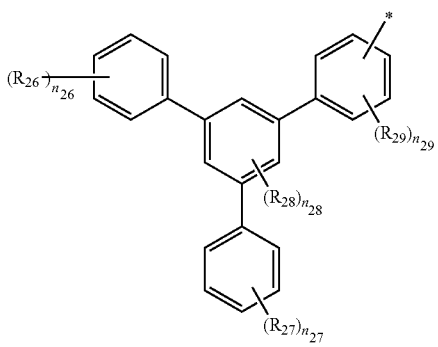
[Chemical Formula 16]
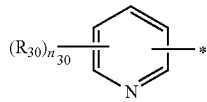
[Chemical Formula 17]
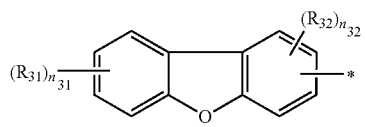
[Chemical Formula 18]
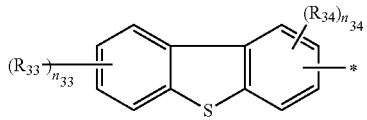
[Chemical Formula 19]
[Chemical Formula 20]
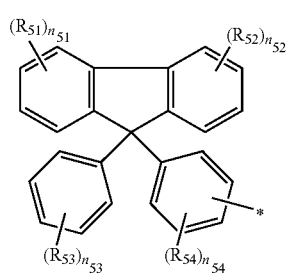
[Chemical Formula 21]
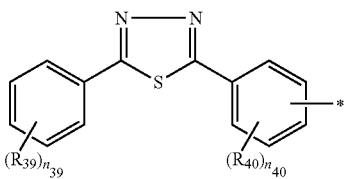
[Chemical Formula 22]
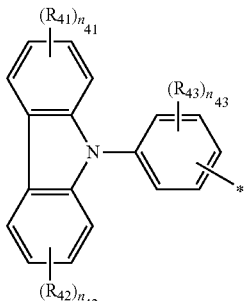
[Chemical Formula 23]
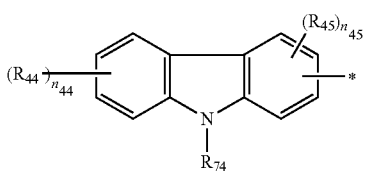
[Chemical Formula 24]
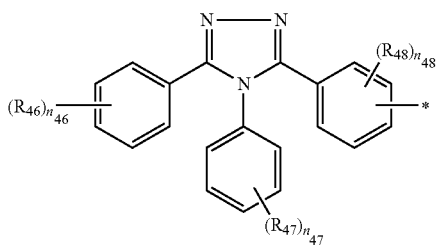
[Chemical Formula 25]
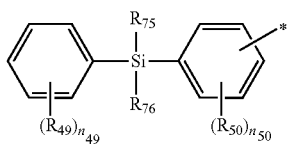
[Chemical Formula 26]

[Chemical Formula 27]

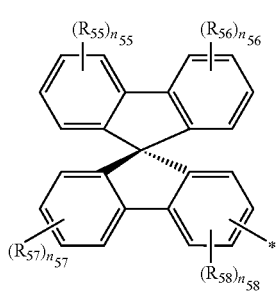

[Chemical Formula 28]

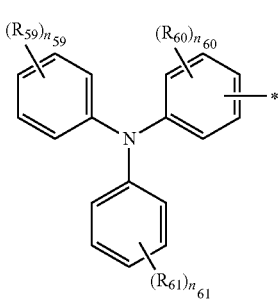

[Chemical Formula 29]

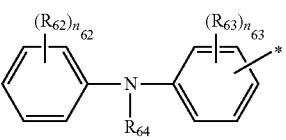

[Chemical Formula 30]

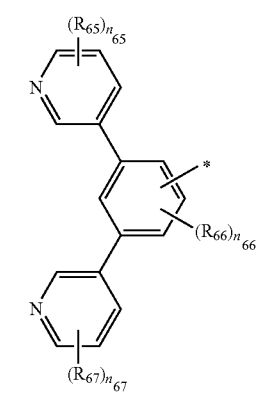

[Chemical Formula 31]

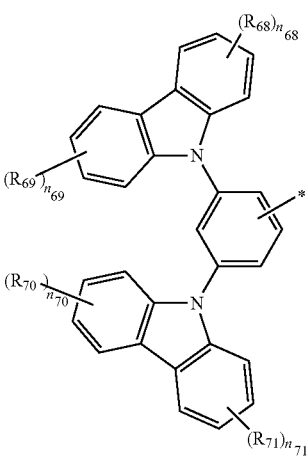

wherein, in the above Chemical Formulae 2 to 31, $R_1$ to $R_{76}$ are the same or different, and are independently selected from a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyl oxy group, a substituted or unsubstituted C1 to C20 acyl group, a substituted or unsubstituted C2 to C20 alkoxy carbonyl group, a substituted or unsubstituted C2 to C20 acyl oxy group, a substituted or unsubstituted C2 to C20 acyl amino group, a substituted or unsubstituted C2 to C20 alkoxy carbonyl amino group, a substituted or unsubstituted C7 to C20 aryloxycarbonylamino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 aryl thiol group, a substituted or unsubstituted C1 to C20 hetero cycloalkyl thiol group, a substituted or unsubstituted C1 to C20 ureide group, a substituted or unsubstituted C1 to C20 phosphoric acid amide group, and a substituted or unsubstituted C3 to C40 silyl group, $n_1$, $n_2$, $n_4$, $n_6$, $n_{10}$, $n_{21}$, $n_{26}$, $n_{27}$, $n_{35}$, $n_{39}$, $n_{46}$, $n_{47}$, $n_{49}$, $n_{53}$, $n_{59}$, $n_{61}$, and $n_{62}$ are the same or different, and are integers ranging from 0 to 5, $n_3$, $n_5$, $n_7$, $n_8$, $n_{11}$, $n_{12}$, $n_{16}$, $n_{22}$, $n_{23}$, $n_{29}$, $n_{30}$, $n_{31}$, $n_{33}$, $n_{36}$, $n_{37}$, $n_{40}$, $n_{41}$ to $n_{44}$, $n_{48}$, $n_{50}$ to $n_{52}$, $n_{54}$, $n_{55}$, $n_{57}$, $n_{60}$, $n_{63}$, $n_{65}$, $n_{67}$, $n_{68}$, $n_{69}$, $n_{70}$, and $n_{71}$ are the same or different, and are integers ranging from 0 to 4, $n_9$, $n_{13}$, $n_{14}$, $n_{18}$, $n_{19}$, $n_{20}$, $n_{25}$, $n_{28}$, $n_{32}$, $n_{34}$, $n_{38}$, $n_{45}$, $n_{56}$, $n_{58}$, and $n_{66}$ are the same or different, and are integers ranging from 0 to 3, and $n_{15}$ and $n_{24}$ are the same or different, and are integers ranging from 0 to 2.

4. An organic compound represented by the following Chemical Formula 32:

[Chemical Formula 32]

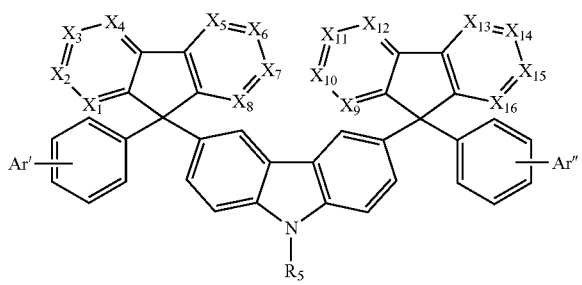

wherein, in the above Chemical Formula 32, $X_1$ to $X_{16}$ are the same or different, and are independently selected from CR' and N, Ar' and Ar'' are the same or different, and are independently selected from a substituted or unsubstituted C6 to C30 aryl group, and a substituted or unsubstituted C2 to C30 heteroaryl group, and $R_5$ is selected from a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted C6 aryl group, a substituted or unsubstituted C7 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, and a substituted or unsubstituted C3 to C40 silyl group, R' is selected from hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, and a substituted or unsubstituted C3 to C40 silyl group.

5. The organic compound of claim 4, wherein Ar' and Ar'' are the same or different, and are independently selected from the substituents represented by the following Chemical Formulae B-1 to B-9:

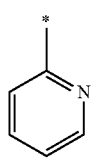

[Chemical Formula B-1]

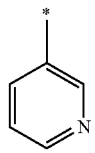

[Chemical Formula B-2]

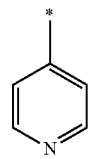

[Chemical Formula B-3]

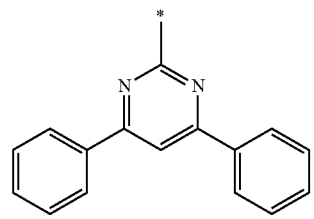

[Chemical Formula B-4]

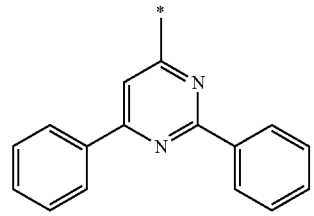

[Chemical Formula B-5]

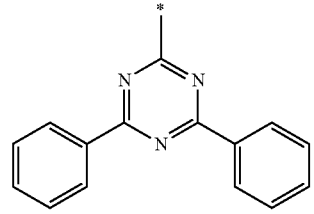

[Chemical Formula B-6]

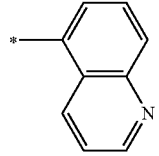

[Chemical Formula B-7]

[Chemical Formula B-8]
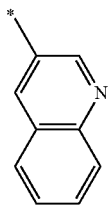
[Chemical Formula B-9]
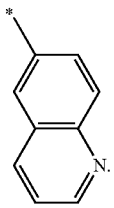
6. An organic compound represented by one of Chemical Formulae selected from the following Chemical Formulae 33, 34, and 37:
[Chemical Formula 33]
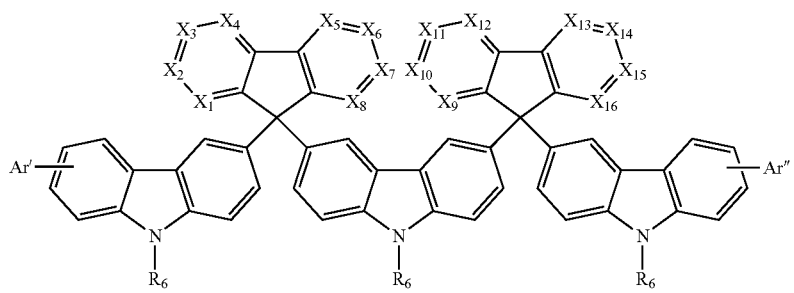
[Chemical Formula 34]
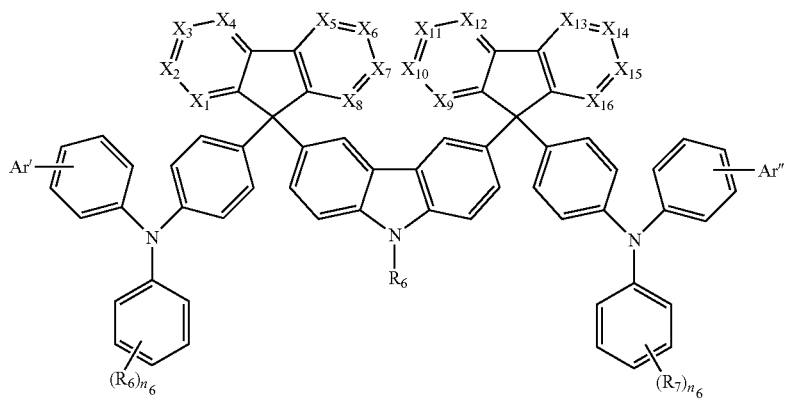
[Chemical Formula 37]
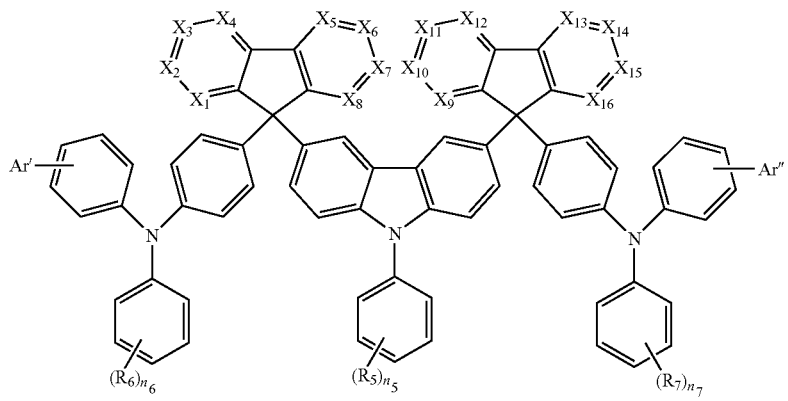

wherein, in the above Chemical Formulae 33, 34, and 37,
X$_1$ to X$_{16}$ are the same or different, and are independently selected from CR' and N, Ar' and Ar" are the same or different, and are independently selected from a substituted or unsubstituted C6 to C30 aryl group, and a substituted or unsubstituted C2 to C30 heteroaryl group, R$_5$ is selected from a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted C6 aryl group, a substituted or unsubstituted C7 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino gimp, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, and a substituted or unsubstituted C3 to C40 silyl group, R$_6$, R$_7$ and R' are the same or different, and are independently hydrogen, a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, and a substituted or unsubstituted C3 to C40 silyl group, n$_5$ to n$_7$ are the same or different, and are independently integers ranging from 0 to 5 and n$_5$' is an integer ranging from 1 to 5.

7. The organic compound of claim 6, wherein Ar' and Ar" are the same or different, and are independently selected from the substituents represented by the following Chemical Formulae B-1 to B-9:

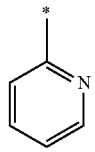

[Chemical Formula B-1]

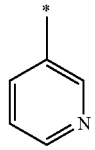

[Chemical Formula B-2]

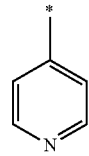

[Chemical Formula B-3]

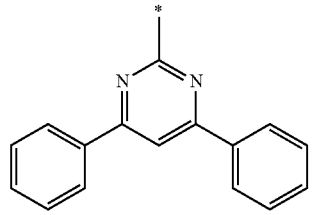

[Chemical Formula B-4]

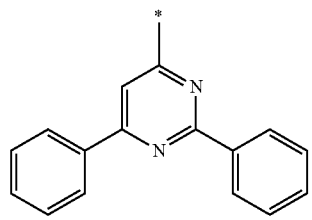

[Chemical Formula B-5]

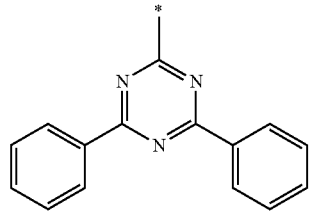

[Chemical Formula B-6]

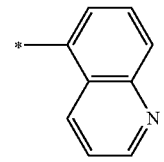

[Chemical Formula B-7]

-continued

[Chemical Formula B-8]

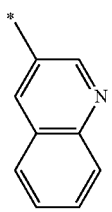

[Chemical Formula B-9]

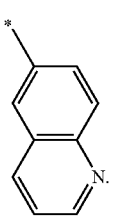

8. The organic compound of claim 4, wherein Ar' and Ar" are the same or different, and are independently selected from a substituted or unsubstituted carbazole, a substituted or unsubstituted arylamine, a substituted or unsubstituted phenyl, a substituted or unsubstituted naphthyl, a substituted or unsubstituted anthracenyl, a substituted or unsubstituted fluorenyl, a substituted or unsubstituted thiophene, a substituted or unsubstituted pyrrole, a substituted or unsubstituted pyridine, a substituted or unsubstituted aryloxadiazole, a substituted or unsubstituted triazole, and a substituted or unsubstituted arylsilane.

9. The organic compound of claim 6, wherein Ar' and Ar" are the same or different, and are independently selected from a substituted or unsubstituted carbazole, a substituted or unsubstituted arylamine, a substituted or unsubstituted phenyl, a substituted or unsubstituted naphthyl, a substituted or unsubstituted anthracenyl, a substituted or unsubstituted fluorene, a substituted or unsubstituted thiophene, a substituted or unsubstituted pyrrole, a substituted or unsubstituted pyridine, a substituted or unsubstituted aryloxadiazole, a substituted or unsubstituted triazole, and a substituted or unsubstituted arylsilane.

10. The organic compound of claim 4, wherein Ar' and Ar" are the same or different, and are independently selected from the following Chemical Formulae 2 to 31:

[Chemical Formula 2]

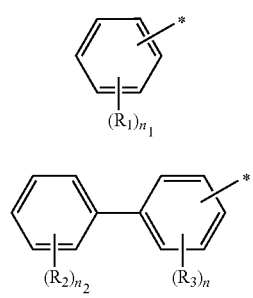

[Chemical Formula 3]

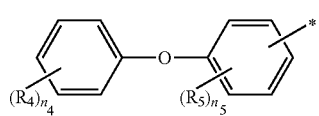

[Chemical Formula 4]

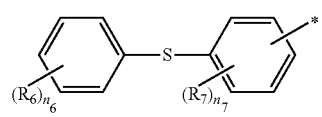

[Chemical Formula 5]

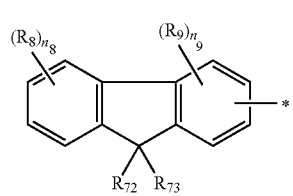

[Chemical Formula 6]

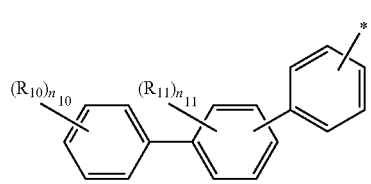

[Chemical Formula 7]

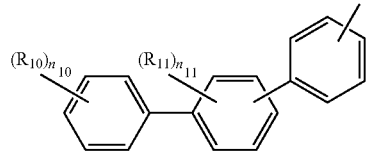

[Chemical Formula 8]

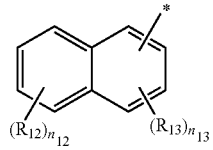

[Chemical Formula 9]

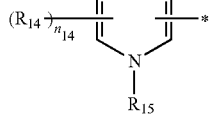

[Chemical Formula 10]

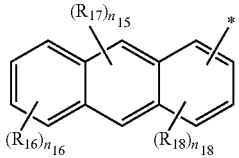

[Chemical Formula 11]

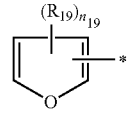

[Chemical Formula 12]

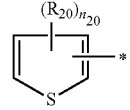

[Chemical Formula 13]

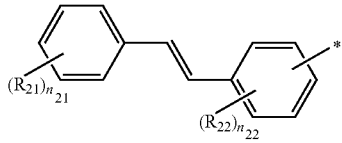

[Chemical Formula 14]

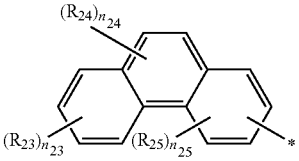

[Chemical Formula 15]
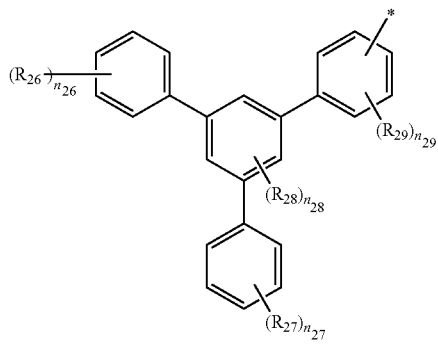
[Chemical Formula 16]
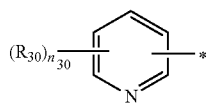
[Chemical Formula 17]
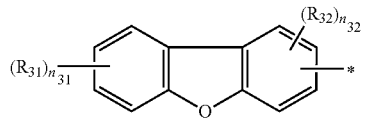
[Chemical Formula 18]
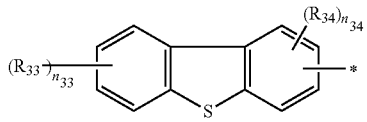
[Chemical Formula 19]
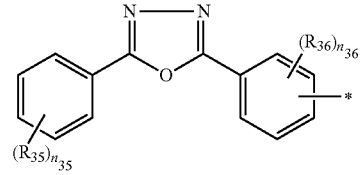
[Chemical Formula 20]
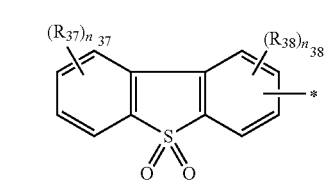
[Chemical Formula 21]
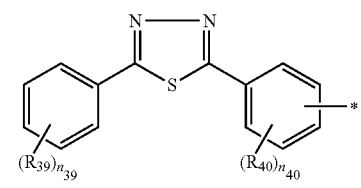
[Chemical Formula 22]
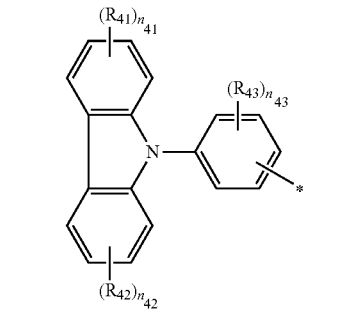
[Chemical Formula 23]
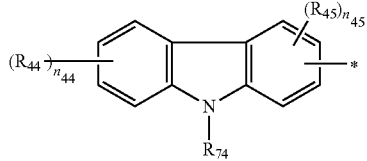
[Chemical Formula 24]
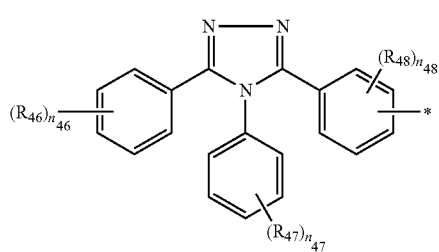
[Chemical Formula 25]
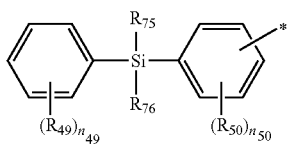
[Chemical Formula 26]
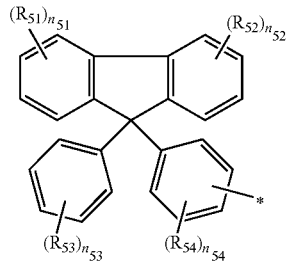
[Chemical Formula 27]
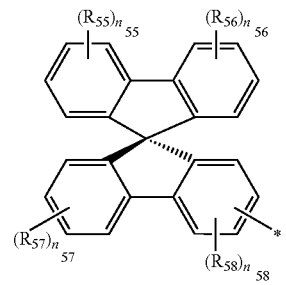
[Chemical Formula 28]
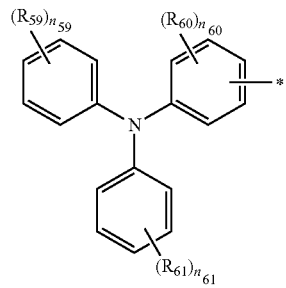
[Chemical Formula 29]
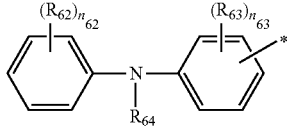

-continued

[Chemical Formula 30]

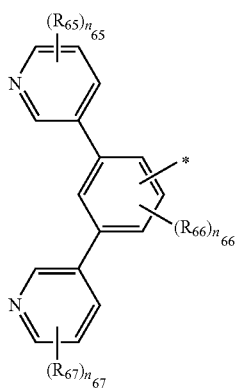

[Chemical Formula 31]

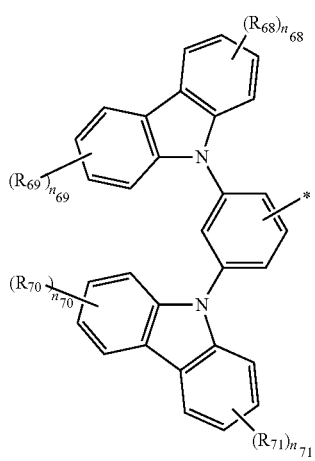

wherein, in the above Chemical Formulae 2 to 31,
$R_1$ to $R_{76}$ are the same or different, and are independently selected from a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyl oxy group, a substituted or unsubstituted C1 to C20 acyl group, a substituted or unsubstituted C2 to C20 alkoxy carbonyl group, a substituted or unsubstituted C2 to C20 acyl oxy group, a substituted or unsubstituted C2 to C20 acyl amino group, a substituted or unsubstituted C2 to C20 alkoxy carbonyl amino group, a substituted or unsubstituted C7 to C20 aryloxycarbonylamino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 aryl thiol group, a substituted or unsubstituted C1 to C20 hetero cycloalkyl thiol group, a substituted or unsubstituted C1 to C20 ureide group, a substituted or unsubstituted C1 to C20 phosphoric acid amide group, and a substituted or unsubstituted C3 to C40 silyl group, $n_1, n_2, n_4, n_6, n_{10}, n_{21}, n_{26}, n_{27}, n_{35}, n_{39}, n_{46}, n_{47}, n_{49}, n_{53}, n_{59}, n_{61}$, and $n_{62}$ are the same or different, and are integers ranging from 0 to 5, $n_3, n_5, n_7, n_8, n_{11}, n_{12}, n_{16}, n_{22}, n_{23}, n_{29}, n_{30}, n_{31}, n_{33}, n_{36}, n_{37}, n_{40}, n_{41}$ to $n_{44}, n_{48}, n_{50}$ to $n_{52}, n_{54}, n_{55}, n_{57}, n_{60}, n_{63}, n_{65}, n_{67}, n_{68}, n_{69}, n_{70}$, and $n_{71}$ are the same or different, and are integers ranging from 0 to 4, $n_9, n_{13}, n_{14}, n_{18}, n_{19}, n_{20}, n_{25}, n_{28}, n_{32}, n_{34}, n_{38}, n_{45}, n_{56}, n_{58}$, and $n_{66}$ are the same or different, and are integers ranging from 0 to 3, and $n_{15}$ and $n_{24}$ are the same or different, and are integers ranging from 0 to 2.

11. The organic compound of claim 6, wherein Ar' and Ar''' are the same or different, and are independently selected from compounds represented by the following Chemical Formulae 2 to 31:

[Chemical Formula 2]

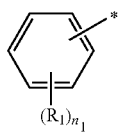

[Chemical Formula 3]

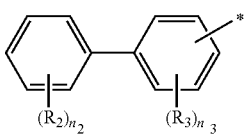

[Chemical Formula 4]

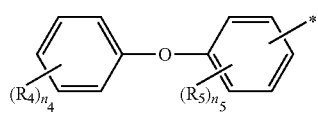

[Chemical Formula 5]

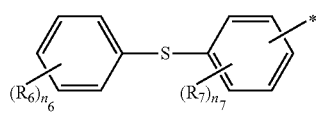

[Chemical Formula 6]

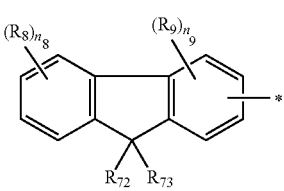

[Chemical Formula 7]

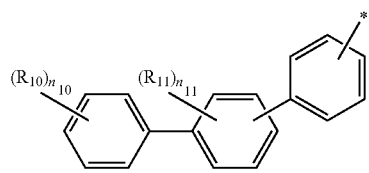

[Chemical Formula 8]

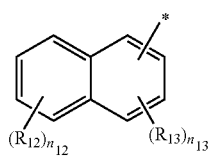

[Chemical Formula 9]

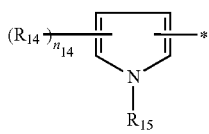

[Chemical Formula 10]
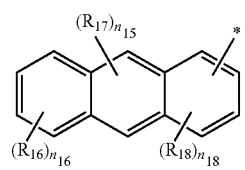
[Chemical Formula 11]
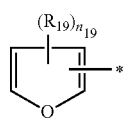
[Chemical Formula 12]
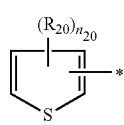
[Chemical Formula 13]
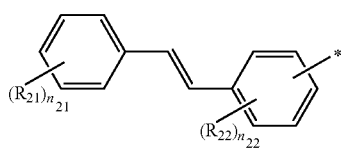
[Chemical Formula 14]
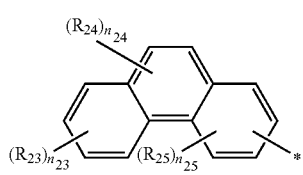
[Chemical Formula 15]
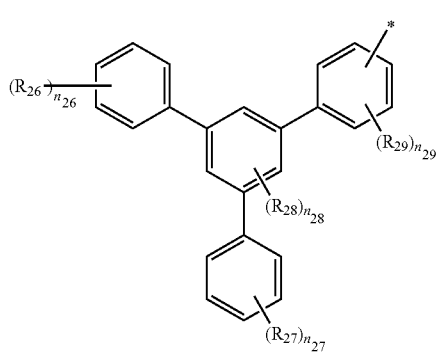
[Chemical Formula 16]
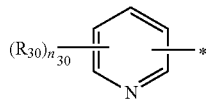
[Chemical Formula 17]
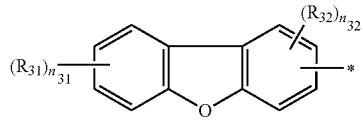
[Chemical Formula 18]
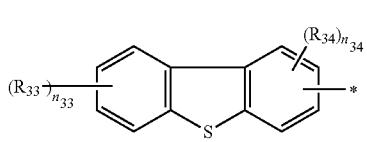
[Chemical Formula 19]
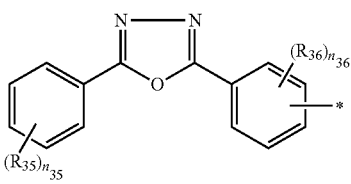
[Chemical Formula 20]
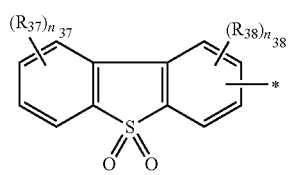
[Chemical Formula 21]
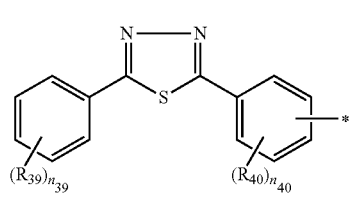
[Chemical Formula 22]
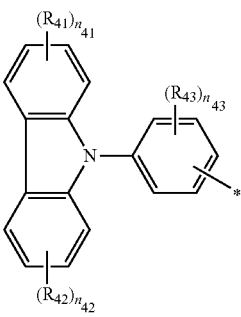
[Chemical Formula 23]
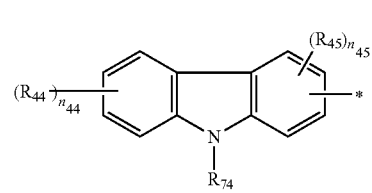
[Chemical Formula 24]
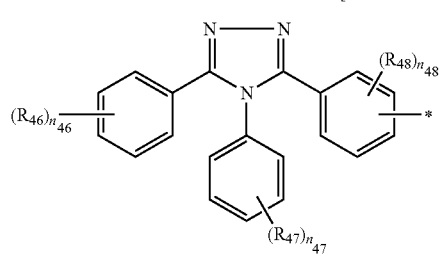
[Chemical Formula 25]
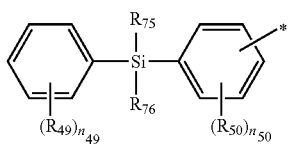

-continued

[Chemical Formula 26]

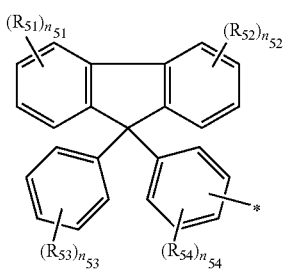

[Chemical Formula 27]

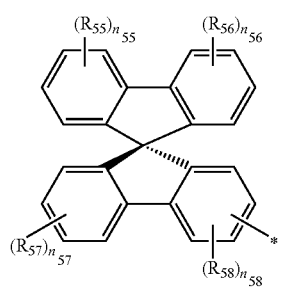

[Chemical Formula 28]

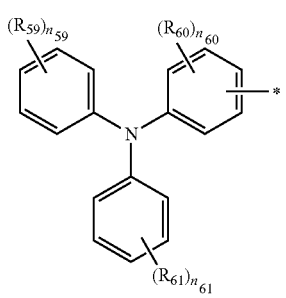

[Chemical Formula 29]

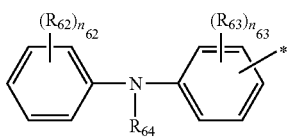

[Chemical Formula 30]

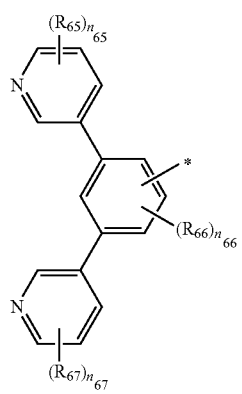

[Chemical Formula 31]

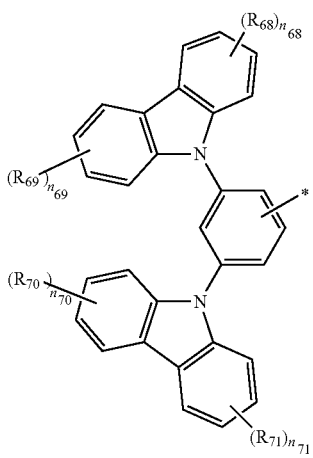

wherein, in the above Chemical Formulae 2 to 31, $R_1$ to $R_{76}$ are the same or different, and are independently selected from a halogen, a cyano group, a hydroxyl group, an amino group, a nitro group, a carboxyl group, a substituted or unsubstituted C1 to C20 alkyl group, a substituted or unsubstituted C2 to C20 alkenyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C2 to C20 heterooxy group, a substituted or unsubstituted C3 to C40 silyloxy group, a substituted or unsubstituted C1 to C20 acyl group, a substituted or unsubstituted C2 to C20 alkoxy carbonyl group, a substituted or unsubstituted C2 to C20 acyloxy group, a substituted or unsubstituted C2 to C20 acylamino group, a substituted or unsubstituted C2 to C20 alkoxy carbonyl amino group, a substituted or unsubstituted C7 to C20 acyloxy carbonyl amino group, a substituted or unsubstituted C1 to C20 sulfamoyl amino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 hetero cycloalkyl thiol group, a substituted or unsubstituted C1 to C20 ureide group, a substituted or unsubstituted C1 to C20 phosphoric acid amide group, and a substituted or unsubstituted C3 to C40 silyl group, $n_1$, $n_2$, $n_4$, $n_6$, $n_{10}$, $n_{21}$, $n_{26}$, $n_{27}$, $n_{35}$, $n_{39}$, $n_{46}$, $n_{47}$, $n_{49}$, $n_{53}$, $n_{59}$, $n_{61}$, and $n_{62}$ are the same or different, and are independently integers ranging from 0 to 5, $n_3$, $n_5$, $n_7$, $n_8$, $n_{11}$, $n_{12}$, $n_{16}$, $n_{22}$, $n_{23}$, $n_{29}$, $n_{30}$, $n_{31}$, $n_{33}$, $n_{36}$, $n_{37}$, $n_{40}$, $n_{41}$ to $n_{44}$, $n_{48}$, $n_{50}$ to $n_{52}$, $n_{54}$, $n_{55}$, $n_{57}$, $n_{56}$, $n_{60}$, $n_{63}$, $n_{65}$, $n_{67}$, $n_{68}$, $n_{69}$, $n_{70}$, and $n_{71}$ are the same or different, and are independently integers ranging from 0 to 4, $n_9$, $n_{13}$, $n_{14}$, $n_{18}$, $n_{19}$, $n_{20}$, $n_{25}$, $n_{28}$, $n_{32}$, $n_{34}$, $n_{38}$, $n_{45}$, $n_{58}$, and $n_{66}$ are the same or different, and are independently integers ranging from 0 to 3, and and $n_{15}$ and $n_{24}$ are the same or different, and are independently integers ranging from 0 to 2.

12. An organic photoelectric device comprising:
an organic layer between a pair of electrodes,
wherein the organic layer includes the organic compound according to claim 1.

13. The organic photoelectric device of claim 12, wherein the organic layer is an emission layer.

14. The organic photoelectric device of claim 12, wherein the organic layer is selected from a hole injection layer (HIL), a hole transport layer (HTL), a hole blocking layer, and combinations thereof.

15. The organic photoelectric device of claim 12, wherein the organic layer is selected from an electron injection layer (EIL), an electron transport layer (ETL), an electron blocking layer, and combinations thereof.

16. The organic photoelectric device as claimed in claim 12, wherein the organic layer includes compound CISH-2:

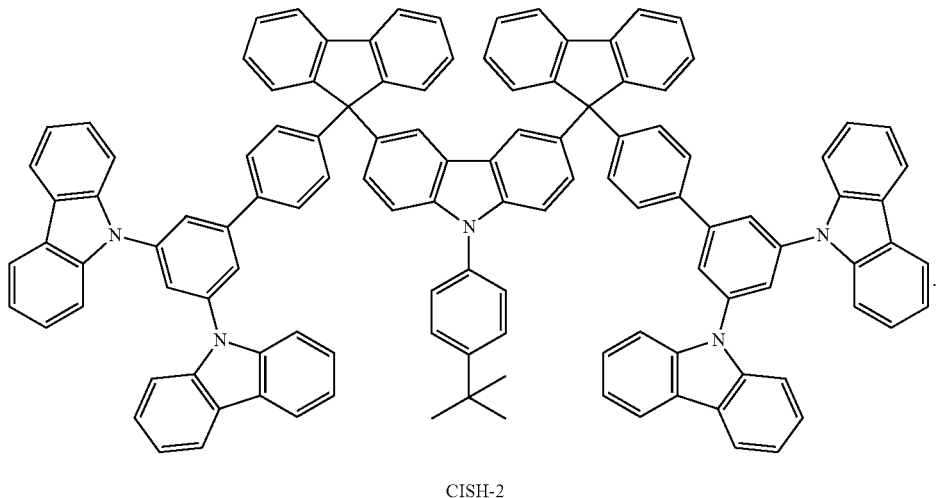 [SMILES: CC(C)(C)c1ccc(-n2c3ccc(C4(c5ccc(-c6cc(-n7c8ccccc8c8ccccc87)cc(-n7c8ccccc8c8ccccc87)c6)cc5)c5ccccc5-c5ccccc54)cc3c3cc(C4(c5ccc(-c6cc(-n7c8ccccc8c8ccccc87)cc(-n7c8ccccc8c8ccccc87)c6)cc5)c5ccccc5-c5ccccc54)ccc32)cc1 ; "CISH-2"]

CISH-2

* * * * *